(12) United States Patent
Mueller-Engel et al.

(10) Patent No.: US 9,018,416 B2
(45) Date of Patent: Apr. 28, 2015

(54) THERMAL SEPARATION PROCESS

(71) Applicant: BASF SE, Ludwigshafen (DE)

(72) Inventors: Klaus Joachim Mueller-Engel, Stutensee (DE); Thomas Walter, Hassloch (DE); Frank Huetten, Mannheim (DE); Markus Ottenbacher, Wilhelmsfeld (DE); Ulrich Hammon, Mannheim (DE)

(73) Assignee: BASF SE, Ludwigshafen (DE)

( * ) Notice: Subject to any disclaimer, the term of this patent is extended or adjusted under 35 U.S.C. 154(b) by 55 days.

(21) Appl. No.: 13/828,505

(22) Filed: Mar. 14, 2013

(65) Prior Publication Data

US 2013/0274519 A1    Oct. 17, 2013

Related U.S. Application Data

(60) Provisional application No. 61/613,024, filed on Mar. 20, 2012.

(30) Foreign Application Priority Data

Mar. 20, 2012    (DE) .................. 10 2012 204 436

(51) Int. Cl.
  *C07C 51/42*    (2006.01)
  *B01D 3/22*    (2006.01)
  *C07C 67/48*    (2006.01)
  *B01D 3/16*    (2006.01)

(52) U.S. Cl.
  CPC ............. *C07C 51/42* (2013.01); *B01D 3/225* (2013.01); *C07C 67/48* (2013.01); *B01D 3/16* (2013.01)

(58) Field of Classification Search
  CPC ........................................... C07C 51/42
  USPC ............................................. 562/600
  See application file for complete search history.

(56) References Cited

U.S. PATENT DOCUMENTS

| | | | |
|---|---|---|---|
| 3,988,213 A | 10/1976 | Yoshida et al. | |
| 7,164,039 B2 | 1/2007 | Petzoldt et al. | |
| 7,323,016 B2 | 1/2008 | Heilek et al. | |
| 7,393,436 B2 * | 7/2008 | Eck et al. ............ | 203/1 |
| 2003/0175159 A1 | 9/2003 | Heilek et al. | |
| 2004/0192965 A1 | 9/2004 | Petzoldt et al. | |

FOREIGN PATENT DOCUMENTS

| | | |
|---|---|---|
| DE | 216 633 A1 | 12/1984 |
| DE | 270 822 A3 | 8/1989 |
| DE | 279 822 A1 | 6/1990 |
| DE | 197 40 252 A1 | 3/1999 |
| DE | 197 40 253 A1 | 3/1999 |
| DE | 199 24 532 A1 | 11/2000 |
| DE | 199 24 533 A1 | 11/2000 |
| DE | 101 56 988 A1 | 5/2003 |
| DE | 101 56 016 A1 | 6/2003 |
| DE | 101 59 823 A1 | 6/2003 |
| DE | 102 57 915 A1 | 10/2003 |
| DE | 102 23 058 A1 | 12/2003 |
| DE | 102 30 219 A1 | 1/2004 |
| DE | 103 13 209 A1 | 3/2004 |
| DE | 103 36 386 A1 | 3/2004 |
| DE | 102 43 625 A1 | 4/2004 |
| DE | 103 32 758 A1 | 5/2004 |
| DE | 103 13 208 A1 | 10/2004 |
| DE | 10 2005 018 702 A1 | 10/2006 |
| DE | 10 2007 004 960 A1 | 7/2008 |
| DE | 10 2007 028 332 A1 | 12/2008 |
| DE | 10 2010 001 228 A1 | 2/2011 |
| DE | 10 2010 048 405 A1 | 5/2011 |
| EP | 0 700 714 A1 | 3/1996 |
| EP | 0 700 893 A1 | 3/1996 |
| EP | 0 882 481 A1 | 12/1998 |
| EP | 0 982 287 A1 | 3/2000 |
| EP | 0 982 289 A2 | 3/2000 |
| EP | 1 029 573 A2 | 8/2000 |
| EP | 1 272 453 | 1/2003 |
| EP | 1 279 429 A1 | 1/2003 |
| EP | 1 305 097 B1 | 6/2004 |
| EP | 1 448 283 | 8/2004 |
| EP | 1 704 906 A1 | 9/2006 |
| EP | 1 125 912 A2 | 8/2011 |
| WO | WO 01/77056 A1 | 10/2001 |
| WO | WO 03/041832 A1 | 5/2003 |
| WO | WO 03/041833 A1 | 5/2003 |
| WO | WO 2004/009525 A1 | 1/2004 |
| WO | WO 2004/035514 A1 | 4/2004 |
| WO | WO 2004/063138 A1 | 7/2004 |
| WO | WO 2004/085367 A1 | 10/2004 |
| WO | WO 2004/085369 A1 | 10/2004 |
| WO | WO 2006/111565 A2 | 10/2006 |
| WO | WO 2007/082827 A1 | 7/2007 |
| WO | WO 2008/090190 A1 | 7/2008 |

* cited by examiner

*Primary Examiner* — Yong Chu
*Assistant Examiner* — Sonya Wright
(74) *Attorney, Agent, or Firm* — Oblon, McClelland, Maier & Neustadt, L.L.P.

(57) ABSTRACT

A thermal separation process between a gas ascending in a separating column and a liquid descending in the separating column, which comprise (meth)acrylic monomers, wherein the separating column comprises a sequence of crossflow mass transfer trays, the crossflow mass transfer trays of which have passage orifices for the ascending gas in crossflow direction both in front of and beyond a downcomer for the descending liquid, and such crossflow mass transfer trays and one such crossflow mass transfer tray in a sequence of crossflow mass transfer trays present in a separating column.

27 Claims, 22 Drawing Sheets

THERMAL SEPARATION PROCESS

The present invention relates to a thermal separation process, conducted in a separation column comprising separating internals, between at least one gas ascending within the separation column and at least one liquid descending within the separation column, at least one of which comprises (meth) acrylic monomers, at least some of the separating internals being at least one sequence of at least two identical crossflow mass transfer trays having at least one downcomer through which liquid descends from the particular crossflow mass transfer tray, and the crossflow mass transfer trays being arranged one on top of another within the at least one sequence in the separation column such that two crossflow mass transfer trays in the separation column, one of which follows the other in the downward direction, are each mounted offset (turned) from one another by 180° about the longitudinal axis of the column, as a result of which their downcomers are on mutually opposite sides (in opposite halves) of the separation column, the at least one downcomer of the upper of two successive crossflow mass transfer trays constitutes at least one upcomer for the crossflow mass transfer tray below it, through which liquid descends from the upper crossflow mass transfer tray as at least one feed to the crossflow mass transfer tray below it, the liquid descending through the at least one upcomer from the upper to the lower crossflow mass transfer tray, viewed over the (entire) lower crossflow mass transfer tray, flows from the at least one feed to the lower crossflow mass transfer tray across the tray to the at least one downcomer of the lower crossflow mass transfer tray, and there are (separating) passage orifices between the at least one feed to the lower crossflow mass transfer tray and the at least one downcomer of the lower crossflow mass transfer tray, through which the at least one gas ascends through the lower crossflow mass transfer tray.

Figure 1:
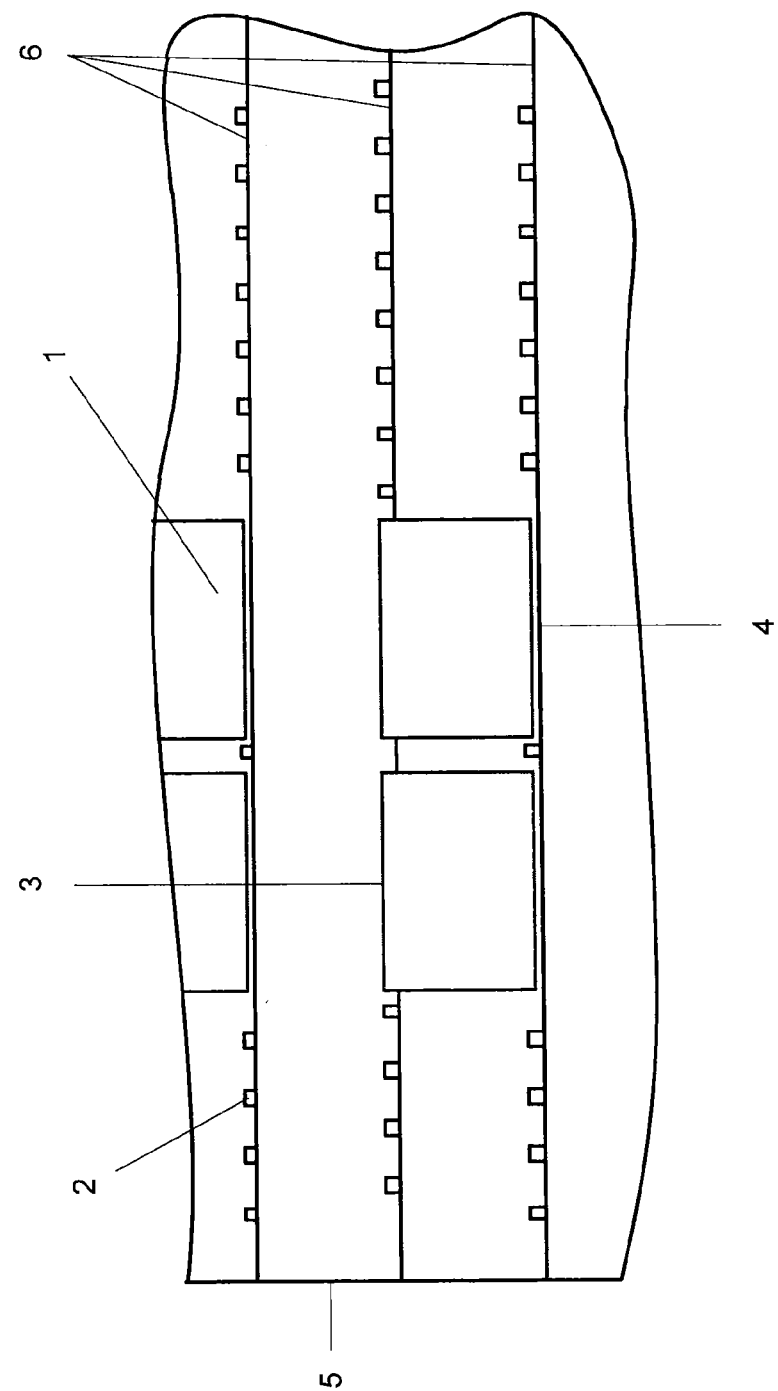
FIG. 1 shows a schematic longitudinal section of mass transfer trays.

The notation "(meth)acrylic monomers" in this document is an abbreviation of "acrylic monomers and/or methacrylic monomers".

The term "acrylic monomers" in this document is an abbreviation of "acrolein, acrylic acid and/or esters of acrylic acid".

The term "methacrylic monomers" in this document is an abbreviation of "methacrolein, methacrylic acid and/or esters of methacrylic acid".

In particular, the (meth)acrylic monomers addressed in this document shall comprise the following (meth)acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

(Meth)acrylic monomers are important starting compounds for preparation of polymers which find use, for example, as adhesives or as water-superabsorbent materials in hygiene articles.

On the industrial scale, (meth)acrolein and (meth)acrylic acid are prepared predominantly by catalytic gas phase oxidation of suitable $C_3/C_4$ precursor compounds (or of precursor compounds thereof). In the case of acrolein and acrylic acid, such precursor compounds used are preferably propene and propane. In the case of methacrylic acid and of methacrolein, isobutene and isobutane are the preferred precursor compounds.

As well as propene, propane, isobutene and isobutane, suitable starting materials, however, are also other compounds comprising 3 or 4 carbon atoms, for example isobutanol, n-propanol or precursor compounds thereof, for example the methyl ether of isobutanol. Acrylic acid can also be obtained by oxidation of acrolein under gas phase catalysis. Methacrylic acid can also be obtained by oxidation of methacrolein under gas phase catalysis.

In such preparation processes, product gas mixtures are normally obtained, from which the (meth)acrylic acid or the (meth)acrolein has to be removed.

Esters of (meth)acrylic acid are obtainable, for example, by direct reaction of (meth)acrylic acid and/or (meth)acrolein with the corresponding alcohols. However, product mixtures are obtained at first in this case too, from which the (meth) acrylic esters have to be removed.

For the above removals, separation processes which are conducted in separation columns comprising separating internals are frequently employed. In these separation columns, gaseous (ascending) and liquid (descending) streams are frequently conducted in countercurrent, at least one of the streams comprising at least one (meth)acrylic monomer.

As a result of the inequilibria which exist between the streams, heat and mass transfer takes place, which ultimately causes the removal (or separation) desired in the separation column. In this document, such separation processes shall be referred to as thermal separation processes.

Examples of, and hence an element of, the expression "thermal separation processes" used in this document are fractional condensation (cf., for example, DE 19924532 A1, DE 10243625 A1 and WO 2008/090190 A1) and rectification (in both, ascending vapor phase is conducted in countercurrent to descending liquid phase; the separating action is based on the fact that the vapor composition at equilibrium is different than the liquid composition), absorption (at least one ascending gas is conducted in countercurrent to at least one descending liquid; the separating action is based on the different solubility of the gas constituents in the liquid) and desorption (the reverse process of absorption; the gas dissolved in the liquid phase is removed by lowering the partial pressure; if the partial pressure of the material dissolved in the liquid phase is lowered at least partly by passing a carrier gas through the liquid phase, this thermal separation process is also referred to as stripping; alternatively or else additionally (at the same time as a combination), the lowering of the partial pressure can be brought about by lowering the working pressure).

For example, the removal of (meth)acrylic acid or (meth) acrolein from the product gas mixture of the catalytic gas phase oxidation can be performed by first conducting a basic removal of the (meth)acrylic acid or the (meth)acrolein by absorption into a solvent (for example water or an organic solvent) or by fractional condensation of the product gas mixture, and subsequently separating the absorbate or condensate obtained further to obtain more or less pure (meth) acrylic acid or (meth)acrolein (cf., for example, DE-10332758 A1, DE 10243625 A1, WO 2008/090190 A1, DE 10336386 A1, DE 19924532 A1, DE 19924533 A1, DE 102010001228 A1, WO 2004/035514 A1, EP 1125912 A2, EP 982289 A2, EP 982287 A1 and DE 10218419 A1).

The fractional condensation addressed above differs from conventional rectification particularly in that the mixture to be separated is supplied to the separation column in gaseous form (i.e. fully converted to vapor form).

The gaseous or liquid mixtures comprising (meth)acrylic monomers which have already been addressed may comprise the (meth)acrylic monomers either in more or less pure form or in dilution (for example with solvent or with diluent gases).

The solvent may either be aqueous or an organic solvent, the specific type of organic solvent being essentially unimportant. The diluent gas may, for example, be nitrogen, carbon oxide (CO and/or $CO_2$), oxygen, hydrocarbon or a mixture of these gases.

This means that, for the purpose of obtaining (meth)acrylic monomers among other purposes, thermal separation processes are applied in a wide variety of different ways to gaseous and/or liquid substance mixtures whose content of (meth)acrylic monomers may be ≥2% by weight, or ≥10% by weight, or ≥20% by weight, or ≥40% by weight, or ≥60% by weight, or ≥80% by weight, or ≥90% by weight, or ≥95% by weight, or ≥99% by weight, and are supplied to the corresponding separation columns.

The (meth)acrylic monomers can be enriched either at the top or in the bottom of the separation column. It will be appreciated, however, that it is also possible to withdraw fractions comprising enriched (meth)acrylic monomers in the upper, lower or middle part of the separation column.

The separating internals present in the separation columns pursue the purpose, in the thermal separation processes, of increasing the surface area for the heat and mass transfer which brings about the separation in the separation column ("the exchange surface").

Useful internals of this kind include, for example, structured packings, random packings and/or mass transfer trays. The separation columns used are frequently those which comprise at least one sequence of mass transfer trays at least as some of the separating internals.

Mass transfer trays pursue the purpose of providing areas with essentially velocity continuous liquid phases in the form of liquid layers which form thereon in the separation column. The surface of the vapor or gas stream which ascends in the liquid layer and is distributed in the liquid phase as it does so is then the crucial exchange surface.

A sequence of mass transfer trays is understood to mean a sequence of at least two generally identical mass transfer trays arranged one on top of another in the separation column. Advantageously in application terms, the clear distance between two immediately successive mass transfer trays in such a series of mass transfer trays is uniform (i.e. the mass transfer trays are arranged equidistantly one on top of another in the separation column).

The simplest embodiment of a mass transfer tray is what is called the dual-flow tray. This is a plate, or plate segments joined together to form a plate, which has essentially flat passage orifices, for example round holes and/or slots, distributed over the plate for the ascending gas or vapor phase (the terms "gaseous" and "vaporous" are used synonymously in this document) (cf., for example, DE 10230219 A1, EP 1279429 A1, U.S. Pat. No. 3,988,213 and EP 1029573 A1). Dual-flow trays do not have any further orifices (for example at least one downcomer (at least one downflow segment)). By virtue of this absence of downcomers, both the gas ascending within the separation column (the vapor ascending within the separation column) and the liquid descending in the separation column have to move flowing in opposite directions alternately through the (same) passage orifices (through the open cross sections of the passages). Reference is also made to the dual flow of ascending gas and descending liquid through the passage orifices, which is why the literature uses the term "dual-flow trays" for such mass transfer trays.

The cross section of the passage orifices of a dual-flow tray is matched to the loading thereof in a manner known per se. If it is too small, the ascending gas flows through the passage orifices at such a high rate that the liquid descending in the separation column is entrained essentially without separating action. If the cross section of the passage orifices is too great, ascending gas and descending liquid move past one another essentially without exchange and the mass transfer tray is at risk of running dry.

In other words, the separation-active working range of a dual-flow tray has two limits. There must be a minimum limiting velocity of the ascending gas in order that a certain liquid layer is maintained on the dual-flow tray in order to enable separating action of the dual-flow tray. The upper limit of the velocity of the ascending gas is fixed by the flood point, when the gas velocity leads to backup of the liquid on the dual-flow tray and prevents it from trickling through.

The longest dimension of the passage orifices of an industrial dual-flow tray (=longest direct line connecting two points on the outline of the cross section of the passage orifice) is typically 10 to 80 mm (cf., for example, DE 10156988 A1). The passage orifices within one dual-flow tray are normally identical (i.e. they all have the same geometric shape and the same cross section (the same cross-sectional area)). Appropriately in application terms, the cross-sectional areas thereof are circles. In other words, preferred passage orifices of dual-flow trays are circular holes. The relative arrangement of the passage orifices of a dual-flow tray advantageously follows a strict triangular pitch (cf., for example, DE 10230219 A1). It will be appreciated that the passage orifices within one and the same dual-flow tray may also be configured differently (vary over the dual-flow tray).

Advantageously in application terms, a sequence of dual-flow trays in a separation column comprises identical dual-flow trays which are preferably arranged equidistantly one on top of another.

According to DE 10156988 A1, however, sequences of dual-flow trays in separation columns can also be employed, the cross section of which (preferably circular) is configured homogeneously within one dual-flow tray but varies within the sequence (for example decreases from the bottom upward).

In general, each dual-flow tray of a corresponding tray sequence concludes flush with the wall of the separation column. However, there are also embodiments in which there is an intermediate space between column wall and tray which is interrupted only partly by bridges. Aside from the actual passage orifices, a dual-flow tray typically has no more than orifices which serve to secure the tray on support rings or the like (cf., for example, DE 10159823 A1).

In the normal working range of a sequence of dual-flow trays, the liquid descending in the separation column trickles in drops from dual-flow tray to dual-flow tray, i.e. the gas phase ascending between the dual-flow trays is permeated by a divided liquid phase. The droplets arriving at the lower dual-flow tray in each case are partly sprayed as they do so. The gas stream flowing through the passage orifices bubbles through the liquid layer formed on the surface of the tray, and intense heat and mass transfer takes place between the liquid and the gas.

The cross section of a separation column is generally circular. This applies correspondingly to the accompanying mass transfer trays.

Dual-flow trays usable for the purposes of this document are described, for example, in Technische Fortschrittsberichte [Technical Progress Reports], Vol. 61, Grundlagen der Dimensionierung von Kolonnenboden [Fundamentals of the dimensioning of column trays], pages 198 to 211, Verlag Theodor Steinkopf, Dresden (1967) and in DE 10230219 A1.

The above-described sequence of dual-flow trays which comprises mass transfer trays without forced flow of the liquid descending onto the tray on the tray is distinguished from sequences of mass transfer trays with such forced liquid flow.

These mass transfer trays have the feature that they additionally have, as well as the passage orifices already described, at least one downcomer. This is at least one downflow orifice present in the mass transfer tray, toward which the liquid which has descended onto the mass transfer tray (for example over an outlet weir (in the simplest embodiment, this may be an upward extension of the downflow orifice with a neck (a chimney; in the case of a circular downflow orifice, a tube))), and which runs into a shaft which feeds the mass transfer tray below in the sequence and which is generally configured with central symmetry with respect to an axis pointing in the longitudinal direction of the column. The cross section of the shaft may vary along this axis (for example narrow) or else be constant.

By virtue of the at least one downcomer of the mass transfer tray, within a sequence of such mass transfer trays, the liquid descending from a higher mass transfer tray can descend independently of the gas or vapor which still rises through the passage orifices of this mass transfer tray as at least one feed of liquid to the next lowest mass transfer tray of the sequence.

The essential basis for this separation of the flow paths of descending liquid and ascending gas is the hydraulic seal (the liquid seal or else shaft seal) of the respective downcomer for the ascending gas (a downcomer must not form a bypass past the passage orifices for the ascending gas; the gas stream (the vapor stream) must not ascend past the passage orifices through a downcomer).

Such a hydraulic seal can be achieved, for example, by drawing the downcomer downward (allowing it to run downward) to such an extent that it is immersed deeply enough into the liquid layer on the next lowest mass transfer tray of the sequence (such a seal is also referred to in this document as "static seal"). The liquid level needed for this purpose can be achieved on the lower mass transfer tray, for example, through the height of appropriate outlet weirs.

However, such a design has the disadvantage that the area of the lower mass transfer tray directly below the outflow cross section of a downcomer of the mass transfer tray above (called the feed area) cannot have any passage orifices for the ascending gas and is thus not available for heat and mass transfer between the liquid layer formed on the lower mass transfer tray and the ascending gas.

In an alternative embodiment, the lower outflow end of the downcomer is truncated to such an extent that it is no longer immersed into the liquid layer present on the mass transfer tray below. In this case, between the lower end of the at least one downcomer and the mass transfer tray onto which the downcomer runs, a sufficiently large intermediate space remains, in which a froth layer forms and heat and mass transfer can take place between a liquid layer which accumulates (on the lower mass transfer tray) and a gas ascending (through this tray). In other words, in this case, the "feed area" of the at least one downcomer on the mass transfer tray below may also have passage orifices and can thus increase the available exchange area of the mass transfer tray, and hence the separating action thereof.

A static liquid seal of the downcomer can be brought about in this case, for example, with the aid of a collecting cup mounted below the outflow end of the downcomer. Appropriately in application terms, in this case, the outer wall of the collecting cup is truncated to such an extent that the outflow end of the downcomer is immersed into the collecting cup (it is also possible to allow the lower edge of the downcomer to end at the upper edge of the collecting cup). In the course of operation of the column, the liquid flowing downward through the downcomer collects in the collecting cup until it flows over the upper edge of the outer wall of the collecting cup. The lower edge of the downcomer is immersed into the liquid present in the collecting cup, and the collecting cup forms a siphon-like liquid seal of the downcomer.

Alternatively, a truncated downcomer can also be sealed dynamically. For this purpose, the downcomer can be sealed, for example, at the lower end thereof with a tray provided with exit orifices of such dimensions that the liquid is backed up in the downcomer and prevents the penetration of gas (cf., for example, EP 0882481A1 and DE 10257915 A1). The shaft seal is established in this case dynamically through the pressure drop which arises at the exit orifices. In other words, in the case of static sealing, the downcomer is sealed by virtue of the outflow end thereof being immersed into backed-up liquid, and, in the case of dynamic sealing, construction features at the outflow end of the downcomer have the effect that the exiting liquid suffers a pressure drop which brings about backup of the liquid descending in the downcomer, which causes the seal. In the simplest case, such a pressure drop can be caused by virtue of a small cross section of the exit orifice of the downcomer being selected compared to the mean cross section of the shaft.

For separation-active operation of a sequence of such mass transfer trays, the design of the at least one downcomer is relevant. Firstly, the cross section of the at least one downcomer selected must be sufficiently large (in general, the corresponding cross-sectional area is greater than the cross-sectional area of a passage orifice), in order that the liquid, even at maximum loading of the separation column, can still descend reliably through the at least one downcomer therewith, and does not back up on the tray above. On the other hand, it has to be ensured that, even in the case of minimal liquid loading, the hydraulic seal of the at least one downcomer still exists.

At a low gas velocity, there is likewise the risk of liquid trickling through the passage orifices. In addition, the liquid has to be able to back up in a downcomer to such an extent that the weight of the backed-up liquid column is sufficient to convey the liquid into the gas space below the mass transfer tray to which the downcomer is connected. This backup height determines the required minimum length of the downcomer and thus partly determines the tray separation required in a sequence of corresponding mass transfer trays.

A significant partial determining factor for the above backup height (backup length) is the pressure drop $\Delta P$ of a mass transfer tray. This pressure drop is suffered by the ascending gas as it flows through the passage orifices, and the "hydrostatic" head of the froth layer on the mass transfer tray. It is responsible for the fact that the pressure in the gas phase of a sequence of such mass transfer trays increases from the top downward. For the "hydrostatic" pressure $h_p$ of the liquid backed up in the downcomer of a mass transfer tray, it is therefore necessary for at least the condition $h_p > \Delta P$ of the mass transfer tray to be met. These connections are known to the person skilled in the art, for example, from EP 1704906 A1, as is the possibility of ensuring that, with an inflow weir on the lower mass transfer tray, in the case of static sealing of the downcomer of the upper mass transfer tray in the liquid layer on the lower mass transfer tray, the shaft seal still exists even in the case of low loading with descending liquid. However, the use of an inflow weir increases the backup height required in the downcomer to force the liquid backed up therein onto the lower mass transfer tray. Overall, the element of the downcomer enables a broadening of the separation-active working range compared to the dual-flow tray. A favorable outflow velocity of the liquid backed up in the downcomer from the downcomer in the process according to the invention is, for example, 1.2 m/s.

In addition, it enables forced circulation of the liquid descending onto a mass transfer tray on this tray.

If, for example, only half of a (preferably circular) mass transfer tray has at least one downcomer (which means that all downflow orifices are present with their full extent within the corresponding circle segment), and, in a sequence of at least two identical mass transfer trays of this kind, the mass transfer trays in a separation column are arranged one on top of another such that two mass transfer trays in the separation column, one of which follows the other in the downward direction, are each mounted offset (turned) by 180° relative to one another about the longitudinal axis of the column, such that the downcomers thereof are on opposite sides (in opposite halves) of the separation column, the liquid which descends from an upper mass transfer tray through the at least one downcomer thereof to the mass transfer tray mounted below must necessarily (i.e. of necessity) flow on this lower mass transfer tray, viewed over the lower mass transfer tray, from the at least one feed area of the at least one downcomer of the upper mass transfer tray (that mounted above) (from the at least one feed through the at least one downcomer of the upper mass transfer tray) to the at least one downcomer of this lower mass transfer tray. In other words, the liquid descending from the upper to the lower mass transfer tray is inevitably conducted across the tray from the at least one feed to the at least one outlet.

Such a liquid flow on a mass transfer tray within a sequence of identical mass transfer trays shall be referred to in this document as a crossflow, the sequence of such identical mass transfer trays as a sequence of identical crossflow mass transfer trays, and the individual mass transfer trays within the sequence as crossflow mass transfer trays.

In the simplest case, the crossflow mass transfer tray is a crossflow sieve tray. Apart from the at least one downcomer, it has passage orifices for the gas ascending in a separation column, and useful embodiments for the configuration thereof are in principle all of those addressed for the dual-flow tray. A crossflow sieve tray preferably likewise has circular holes as passage orifices, and these likewise, advantageously for application purposes, have a uniform radius. As already mentioned, the at least one downcomer enables the liquid descending in a separation column, in a sequence of crossflow sieve trays, irrespective of the flow path of the vapor ascending in the sequence, to descend (through the passage orifices) from a higher crossflow sieve tray to the next lowest crossflow sieve tray. On the lower tray, the liquid flows in crosscurrent from the at least one feed of the lower tray, which is formed by the at least one outlet of the higher crossflow sieve tray, to the at least one downcomer (to the at least one outlet) of the lower tray, the desired liquid height on the lower crossflow sieve tray being partly ensured, for example, by the height of at least one outlet weir over which the liquid can flow to the at least one downcomer. In addition, the liquid is retained on the crossflow sieve tray by the backup pressure of the vapor ascending in the separation column. If the vapor loading of a crossflow sieve tray, however, falls below a minimum value, the result may be trickling of the liquid through the passage orifices, which reduces the separating action of the crossflow sieve tray and/or leads to the crossflow sieve tray running dry.

This risk of running dry can be counteracted by providing the downflow orifice of the at least one downcomer with an outlet weir and extending the respective passage orifice in the upward direction with a neck (a chimney; in the case of a circular passage orifice, a tube).

Normally mounted over the end of the neck are vapour-deflecting hoods (bubble caps, inverted cups) (these may in the simplest case be placed on with screw connections to the neck (for example at the front and back) and are effectively pulled over the neck), which are immersed into the liquid backed up on the tray. The vapor ascending through the respective passage orifice at first flows through the neck thereof into the accompanying hood, in which it is deflected, in order then, in contrast to the crossflow sieve tray, to flow in parallel to the tray surface from the hood into the liquid backed up thereon (such a "parallel outflow" is generally favorable in processes according to the invention in that it is able to "blow away" undesirably formed polymer particles and thus to bring about a self-cleaning effect). The gas streams (vapor streams) exiting from adjacent hoods, preferably distributed equidistantly over the trays, agitate the liquid backed up on the tray and form a froth layer therein, in which the heat and mass transfer takes place. Such crossflow mass transfer trays are also referred to as crossflow bubble-cap trays or crossflow hood trays. Since they have backed-up liquid even in the case of low loading with ascending gas (vapor) and thus are at no risk of running dry, they are also referred to as hydraulically sealed crossflow trays. Compared to crossflow sieve trays, they typically require higher capital costs and cause higher pressure drops of the gas ascending through them. The passage orifice of these trays designed (configured) as described is also referred to as bubble-cap passage orifice or hood passage orifice, in contrast to the simple sieve passage orifice of a sieve tray.

The most important component of the crossflow bubble-cap tray is the bubble cap (cf., for example, DE 10243625 A1 and Chemie-Ing.-Techn. Volume 45, 1973/No. 9+10, p. 617 to 620). According to the configuration and arrangement of the bubble caps (vapor deflecting hoods, hoods), crossflow bubble-cap trays are divided, for example, into crossflow round bubble-cap trays (the cross sections of passage orifice, chimney (neck) and bubble cap (vapor deflecting hood) are round (for example the cylinder bubble-cap tray or the flat bubble-cap tray), tunnel crossflow trays (the cross sections of passage orifice, chimney and bubble cap (hood) are rectangular; the passages with their bubble caps are arranged one after another within rows arranged alongside one another, with the longer rectangular edge aligned parallel to the crossflow direction of the liquid) and crossflow Thormann® trays (the cross sections of passage orifice, chimney and bubble cap (hood) are rectangular; the passages with their bubble caps are arranged one after another within rows arranged alongside one another, with the longer rectangular edge aligned at right angles to the crossflow direction of the liquid). Crossflow Thormann trays are described, for example, in DE 19924532 A1 and in DE 10243625 A1, and the prior art acknowledged in these two documents.

Figure 3:
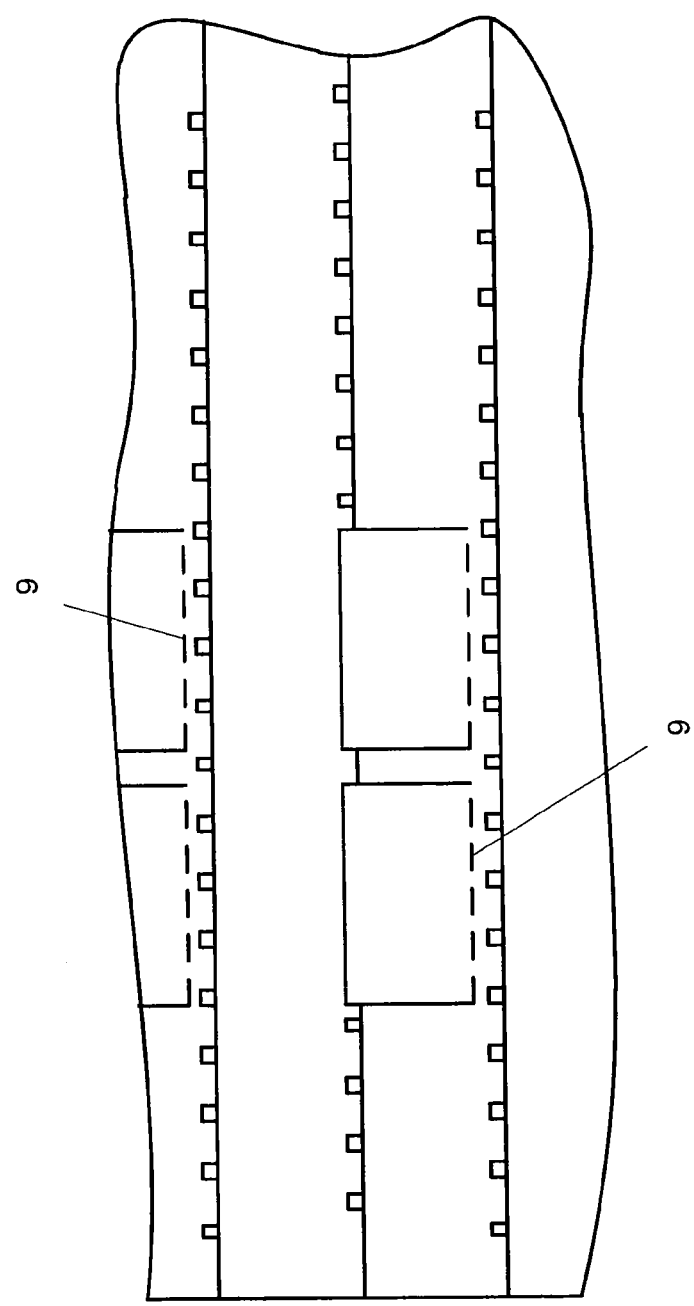

The bubble-cap edge in crossflow bubble-cap trays may have very different forms (cf. DE 10243625 A1 and Chemie-Ing. Techn. Volume 45, 1973/No. 9+10, p. 617 to 620). FIG. 3 from Chemie-Ing. Techn. Volume 45, 1973/No. 9+10, p. 618 shows some examples of the serrated and slotted edge. The serrations and slots are typically shaped such that the vapor emerging from the bubble cap into the liquid backed up on the mass transfer tray dissolves very easily into a large number of bubbles or vapor jets. The above FIG. 3 and various figures in DE 10243625 A1 also show illustrative embodiments of bubble-cap edges having a sawtooth-like structure, the teeth of which are additionally equipped with guide fins (guide surfaces) ("slots bent open"). The guide fins are intended to impose a tangential exit direction on the gas stream (vapor stream) exiting from the sawtooth-like slots bent open (direct the gas exit into the liquid in an oblique direction), as a result of which the surrounding liquid receives a directed movement pulse which, in cooperation with the arrangement of the bubble caps (vapor deflecting hoods), can lead to a directed liquid flow on the crossflow bubble-cap tray, which is superimposed on the crossflow which is established, viewed over the mass transfer tray (frequently, such slots bent open are also referred to as forcing slots). For example, in a sequence of crossflow Thormann trays, the liquid on a lower crossflow Thormann tray does not flow directly across the tray, but rather, in the manner described above, is driven in a meandering manner from the at least one feed to the at least one outlet. The space between two hoods of a crossflow Thormann tray arranged one after the other in crossflow direction forms a channel in each case, in which the liquid flows. The detailed configuration of a crossflow Thormann tray is additionally normally in such a manner that the liquid flows in countercurrent in two channels which are successive in each case in crossflow direction (cf., for example, FIG. 3 of DE 10243625 A1). The meandering crossflow which results in this manner prolongs the flow path of the liquid from the at least one feed to the at least one outlet, which promotes the separating action of a crossflow Thormann tray.

As already stated, in a crossflow bubble-cap tray, the gas emerging from the bubble cap, in contrast to the crossflow sieve tray, is introduced parallel to the tray surface into the liquid backed up on the crossflow bubble cap tray. Frictional and buoyancy forces ensure that, with increasing distance of the emerging gas stream from the bubble-cap edge, more and more substreams thereof are deflected in a direction at right angles to the crossflow bubble-cap tray and ultimately escape from the liquid layer. With increasing gas loading of a bubble cap, the velocity of the gas stream emerging from it grows, which increases the distance from the edge of the bubble cap ("the effective range of the bubble cap") up to which the above-described deflection occurs.

This dependence of the effective range of a rigid bubble cap on the gas loading can be counteracted by configuring (designing) the passage orifice of a crossflow mass transfer tray as a valve (as a valve passage orifice). The resulting crossflow mass transfer trays are referred to as crossflow valve trays (cf., for example, DD 270822 A1, DD 216633 A1 and DE 102010001228 A1).

The term "crossflow valve trays" in this document thus covers crossflow mass transfer trays which have passage orifices (tray holes) with limited-stroke plate, ballast or lifting valves (floating flaps) which adjust the size of the vapor passage orifice to the respective column loading.

In a simple configuration, the passage orifices of the tray are covered for the aforementioned purpose with covers or plates (disks) movable in the upward direction. In the course of passage of the ascending gas, the lids (plates, disks) are raised by the gas stream in a corresponding guide structure (guide cage) additionally mounted over the respective passage orifice (which is normally firmly anchored on the tray) and finally reach a stroke height corresponding to the gas loading (instead of a guide cage, the disk may also possess upwardly movable valve legs anchored to the tray, the upward mobility of which has an upper limit). The gas stream ascending through the passage orifice is deflected at the underside of the raised lid (plate, disk) in a similar manner to that in the bubble cap (in the case of a bubble-cap passage orifice) and exits from the exit region formed under the raised plate (lid, disk) and, as is the case for the bubble-cap tray, enters the liquid backed up on the tray parallel thereto. The plate stroke thus controls the size of the gas exit region and automatically adjusts to the column loading until the upper end of the guide cage limits the maximum possible stroke height. The plates may have spacers directed downward, such that, at low gas loading, the valve closes only to such an extent that the space provided by the spacers still permits vigorous mixing of the horizontal gas outflow with the crossflowing liquid. Spacers also counteract sticking of the valve disk on the tray. Through suitable configuration of the valve elements of a crossflow valve tray, the blowing direction of the valve element can be adjusted, and hence the forced liquid flow on the crossflow valve tray can additionally be influenced (cf., for example, DD 216 633 A1). The principle of crossflow valve trays, and valve trays usable for the purposes of the present document, can be found, for example, in Technische Fortschrittsberichte, volume 61, Grundlagen der Dimensionierung von Kolonnenboden, pages 96 to 138. As well as the above-described moving valves, the person skilled in the art is also aware of fixed valves. These are normally disk-shaped, or trapezoidal, or rectangular units which are punched out of the tray plate and are connected thereto via fixed legs directed upward.

Especially in the case of relatively large diameters of a separation column, on crossflow mass transfer trays, a notable liquid gradient naturally forms proceeding from the at least one feed until attainment of the outlet weir of the at least one outlet (the gradient of the backup height of the liquid feeds the crossflow (to a limited degree)). The result of this is that, in regions with a relatively low liquid height, due to the resulting lower resistances, the ascending vapor (the ascending gas) can pass through the liquid layer more easily in comparative terms. This can ultimately give rise to an inhomogeneous gas loading of the crossflow mass transfer tray (there is preferential flow through the regions with a lower liquid height (a lower flow resistance)), which impairs the separating action thereof. A compensating effect is possible in this respect through the use of, for example, bubble caps of adjustable height (alternatively, the bubble-cap size can also be altered) in the case of crossflow bubble-cap trays, or by use of, for example, plates (lids) with different weight in the case of crossflow valve trays, such that the mass transfer tray produces gas essentially homogeneously over its cross section (where the liquid height on the crossflow mass transfer tray is lower, the height of the bubble cap is, appropriately in application terms, selected at a correspondingly lower level, or the weight of the stroke plate (stroke lid) is selected at a correspondingly higher level; the height of the bubble cap can, for example, also be lowered by controlled shortening of the length of the corresponding chimney, at the end of which the bubble cap is optionally screwed on; alternatively or additionally, for example, the serration/slot structure of the bubble-cap edge can also be varied in order to bring about the desired flow resistance compensation; ideally, the adjustment is made over the crossflow mass transfer tray such that, in operation of the separation column, every bubble cap present on a crossflow bubble-cap tray causes the same flow resistance for the ascending gas). Otherwise, the passages (the passage orifices) of a crossflow mass transfer tray are generally advantageously configured uniformly.

Orifices running (from the top downward) through a crossflow mass transfer tray, the cross-sectional area of which is typically more than 200 times smaller than the overall cross-sectional area of all other orifices of the crossflow mass transfer tray (not including the cross section of the at least one downcomer), do not constitute (separating) passage orifices for the gas ascending through the crossflow mass transfer tray and are therefore not counted as part thereof. For example, such orifices may be tiny emptying holes through which hydraulically sealed crossflow trays can empty when the separation column is shut down. It is also possible for such orifices to serve for screw connection purposes.

Sequences of mass transfer trays having at least one downcomer, in which the at least one feed and the at least one outlet are present, for example, in the same half of the (circular) mass transfer tray, or in which the at least one feed is in the middle of the tray and the at least one outlet is at the edge of the tray, do not constitute a sequence of crossflow mass transfer trays in the sense of the application (of the invention).

The efficacy of crossflow mass transfer trays designed as described is typically less than that of one theoretical plate (one theoretical separation stage). A theoretical plate (or theoretical separation stage) shall be understood in this document quite generally to mean that spatial unit of a separation column which comprises separating internals and is used for a thermal separation process which brings about enrichment of a substance in accordance with the thermodynamic equilibrium. In other words, the term "theoretical plate" is applicable both to separation columns with mass transfer trays and to separation columns with structured packings and/or random packings.

The prior art recommends the use of sequences of at least two identical crossflow mass transfer trays, in separation columns including those comprising separating internals, which are employed for performance of thermal separation processes between at least one gas stream ascending in the separation column and at least one liquid stream descending in the separation column, and wherein at least one of the streams comprises at least one (meth)acrylic monomer. For example, documents DE 19924532 A1, DE 10243625 A1 and WO 2008/090190 A1 recommend the additional use of a sequence of identical hydraulically sealed crossflow mass transfer trays in a separation column for performance of a process for fractional condensation of a product gas mixture comprising acrylic acid from a heterogeneously catalyzed gas phase partial oxidation of $C_3$ precursors of acrylic acid with molecular oxygen, which comprises, from the bottom upward, at first dual-flow trays and subsequently hydraulically sealed crossflow mass transfer trays.

Figure 4:
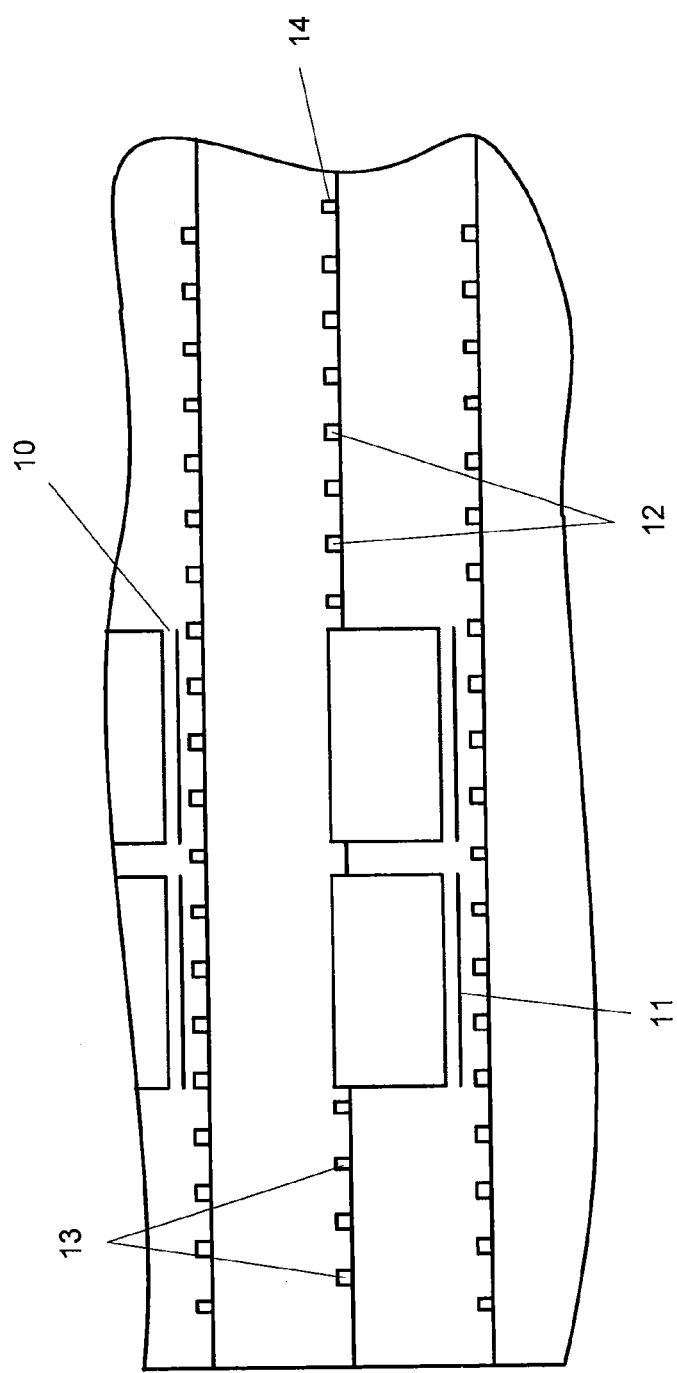

A characteristic feature of the sequences of crossflow mass transfer trays recommended in the prior art is that the lower of two successive crossflow mass transfer trays in the sequence in each case, in the direction of crossflow from the at least one feed thereof to the at least one downcomer thereof, has passage orifices only in the region between the at least one feed and the at least one downcomer (the at least one downflow orifice) (cf., for example, FIGS. 3 and 4 of DE 10243625 A1, FIG. 1 of DD 279822 A1, FIG. 1 of DD 216633 A1, and FIG. 1 from Chemie-Ing.-Techn. Volume 45, 1973/No. 9+10, pages 617 to 620).

A problematic property of (meth)acrylic monomers is the tendency thereof to unwanted polymerization, which cannot completely be suppressed even by the addition of polymerization inhibitors, particularly in the liquid phase.

A disadvantage of the recommendations of the prior art is that, in the case of continuous performance of the thermal separation process, over prolonged periods of operation within the sequence of crossflow mass transfer trays, there is comparatively frequently formation of unwanted polymer. This is particularly disadvantageous because the operator of the thermal separation process, due to the unwanted polymer formation, has to interrupt the thermal separation process time and again in order to remove the polymer formed (this can partly or completely block the passage orifices of the crossflow mass transfer tray).

It was therefore an object of the present invention to at least partly remedy the described disadvantage of the recommendation of the prior art without significantly impairing the separating action.

Accordingly, a thermal separation process, conducted in a separation column comprising separating internals, between at least one gas ascending within the separation column and at least one liquid descending within the separation column, at least one of which comprises (meth)acrylic monomers (i.e. at least one gas stream ascending in the separation column and/or at least one liquid stream descending in the separation column comprises at least one (meth)acrylic monomer), at least some of the separating internals being at least one sequence of at least two identical crossflow mass transfer trays having at least one downcomer through which liquid descends from the particular crossflow mass transfer tray, and the crossflow mass transfer trays being arranged one on top of another within the at least one sequence in the separation column such that two crossflow mass transfer trays in the separation column, one of which follows the other in the downward direction, are each mounted offset (turned) from one another by 180° about the longitudinal axis of the column, as a result of which (such that) their downcomers are on mutually opposite sides (in opposite halves) of the separation column, the at least one downcomer of the upper of two successive crossflow mass transfer trays constitutes at least one upcomer for the crossflow mass transfer tray below it, through which liquid descends from the upper crossflow mass transfer tray as at least one feed to the crossflow mass transfer tray below it, the liquid descending through the at least one upcomer from the upper to the lower crossflow mass transfer tray, viewed over the (entire) lower crossflow mass transfer tray, flows from the at least one feed to the lower crossflow mass transfer tray across the tray to the at least one downcomer of the lower crossflow mass transfer tray, and there are (separation-active) passage orifices between the at least one feed to the lower crossflow mass transfer tray and the at least one downcomer of the lower crossflow mass transfer tray, through which the at least one gas ascends through the lower crossflow mass transfer tray, is provided, wherein at least within one of the at least one sequence of identical crossflow mass transfer trays, the lower of two successive crossflow mass transfer trays in each case, (looking) in the direction of the crossflow from the at least one feed thereof to the at least one downcomer thereof, additionally has at least one (separation-active) passage orifice for the at least one ascending gas beyond at least one downcomer (and the uppermost crossflow mass transfer tray in this sequence is identical to the crossflow mass transfer tray below it).

It will be appreciated that, in the process according to the invention, in the at least one inventive sequence of crossflow mass transfer trays, the liquid descending through the at least one upcomer from the upper to the lower crossflow mass transfer tray must not flow directly from the at least one feed to the at least one downcomer. Instead, this flow from the at least one feed to the at least one outlet may be similarly meandering, for example, to that in a conventional crossflow Thormann tray.

An inventive sequence of at least two identical crossflow mass transfer trays may, in the process according to the invention, be a sequence of crossflow sieve trays, or crossflow bubble-cap trays, or a sequence of crossflow valve trays. It will advantageously comprise at least three identical, preferably at least four identical and more preferably at least five or at least ten identical crossflow mass transfer trays.

In general, (the at least) one inventive sequence of at least two identical crossflow mass transfer trays in the process according to the invention comprises not more than fifty, frequently not more than forty and in some cases not more than thirty identical crossflow mass transfer trays.

Advantageously in accordance with the invention, the crossflow mass transfer trays in an inventive sequence of at least two identical crossflow mass transfer trays are arranged equidistantly one above another.

It will be appreciated that the separation column used for a thermal separation process according to the invention may comprise, as well as at least one inventive sequence of at least two identical crossflow mass transfer trays, also one or more conventional, i.e. noninventive, sequences of identical crossflow mass transfer trays and/or other customary separating internals (for example (structured and/or unstructured) packings, random packings, sequences of dual-flow trays etc.).

Advantageously in accordance with the invention, all sequences of identical crossflow mass transfer trays present in a separation column used for a thermal separation process according to the invention are inventive sequences of crossflow mass transfer trays.

Normally, the crossflow mass transfer trays of an inventive sequence of crossflow mass transfer trays have a circular cross section.

Appropriately in application terms, the crossflow mass transfer trays of an inventive sequence of crossflow mass transfer trays conclude flush with the column walls. However, there are also possible embodiments in which an intermediate space exists between column wall and tray, which is only partly interrupted by bridges.

The passage orifices of a crossflow mass transfer tray used for an inventive sequence of crossflow mass transfer trays are, apart from the edge region of the tray, appropriately in application terms, configured homogeneously (identically). In other words, normally (as far as permitted by the size ratio of passage orifice and cross section of the tray) at least 20%, preferably at least 30%, more preferably at least 40% or at least 50%, and most preferably at least 60% or at least 70%, or at least 80%, of all passage orifices of such a crossflow mass transfer tray have a uniform cross section (the high percentages generally exist in separation columns with large cross section (diameter of, for example, >2 m), and the lower percentages in separation columns with a small cross section (diameter of, for example, <2 m), since the edge regions in the latter are of greater weight and may not permit a higher percentage). This (such uniformity) likewise applies to corresponding necks, bubble caps, valves, etc., apart from any measures which are taken in order to counteract a liquid gradient from the at least one feed to the at least one outlet on the crossflow mass transfer tray in the operating state.

The cross section of a passage orifice of a crossflow mass transfer tray used for an inventive sequence of crossflow mass transfer trays may be circular, polygonal (for example triangular, square or rectangular) or take the form of the cross section of an elongated hole (the geometry of an elongated hole with box length L (box side L) derives from that of a rectangle with side lengths L and C in that the sides with the length C are each replaced by a semicircle with the diameter C (the hole width), the semicircle curve pointing out of the rectangular area, and the side length L being greater than the side length C; cf. DE 10 2007028332 A1). In principle, the cross section of such a passage orifice may, however, be of any geometric shape.

Advantageously in application terms, the passage orifices of a crossflow mass transfer tray for an inventive sequence of crossflow mass transfer trays are arranged regularly on the crossflow mass transfer tray (this statement relates more particularly to the passage orifices A defined later in this document). Such a regular arrangement may, in the case of circular passage orifices, for example, be a regular triangular pitch (cf., for example, DE 10230219 A1). In the case of rectangular passage orifices, such a regular arrangement may be a succession of rows, the rectangles being arranged one behind another within a row.

Crossflow mass transfer trays of an inventive sequence of crossflow mass transfer trays must have at least one downcomer. Advantageously in accordance with the invention, they have more than one downcomer. For example, the number of downcomers may be two, or three, or four, or five, or six, or seven, or eight, or nine, or ten. In general, the aforementioned number of downcomers will not be more than twenty, typically not more than fifteen.

If the crossflow mass transfer tray of an inventive sequence of crossflow mass transfer trays has more than one downcomer, all of these (to their full extent) are in one half of the crossflow mass transfer tray which preferably has a circular cross section.

Preferably in accordance with the invention, the at least one downcomer (all downcomers or downflow orifices thereof) of a circular crossflow mass transfer tray suitable for an inventive sequence of crossflow mass transfer trays is/are within a circle segment (a circle segment refers to the geometry of part of a circle surface which is defined by a circle arc and a circle chord) of the crossflow mass transfer tray, the area of which is not more than five sixths, advantageously not more than four fifths, and particularly advantageously not more than three quarters or not more than two thirds of half of the circle area of the crossflow mass transfer tray. In general, the area of this circle segment is, however, at least one fifth or at least one quarter of half of the circle area of the crossflow mass transfer tray.

Quite generally, it is advantageous for the process according to the invention when the distance between the center of the downflow orifice of the at least one downcomer of a circular crossflow mass transfer tray of an inventive sequence of crossflow mass transfer trays and the geometric center of the circular crossflow mass transfer tray is at least as long as one third of the radius, preferably at least as long as two fifths of the radius, and more preferably at least as long as half the radius or at least as long as three fifths of the radius of the crossflow mass transfer tray. The shortest distance between the outline (circumference line) of the at least one downcomer and the outline of the aforementioned crossflow mass transfer tray is, advantageously in accordance with the invention, such that it satisfies the space required by at least one passage orifice, preferably at least two passage orifices.

Within an abovementioned circle segment, the downcomers or the downflow orifices thereof are advantageously arranged such that, on that straight line which connects the center of one downflow orifice to the center of the opposite feed area (the feed area of the opposite feed), there is no further downflow orifice (i.e. the straight line does not intersect or come into tangential contact with any further downflow orifice).

In addition, the distribution (arrangement) of the downflow orifices within the circle segment is additionally undertaken advantageously such that the shortest direct connecting line from the center of a downflow orifice to a point on the circumference (on the circumference line, on the outline) of the crossflow mass transfer tray is not longer than two thirds of the radius, preferably not longer than three fifths of the radius, more preferably not longer than half the radius or than two fifths of the radius of the crossflow mass transfer tray.

Appropriately in accordance with the invention, the downflow orifices of the downcomers of a crossflow mass transfer tray which is relevant in accordance with the invention have a uniform cross section (including the cross-sectional area). This may be, for example, circular, rectangular, square or that of an elongated hole. With regard to the other features of a downcomer too, the downcomers of a crossflow mass transfer tray suitable for an inventive sequence of crossflow mass transfer trays, advantageously in accordance with the invention, are uniform.

Normally, the cross-sectional area $F_A$ of the downflow orifice belonging to a downcomer in a crossflow mass transfer tray suitable for an inventive sequence of crossflow mass transfer trays is at least twice as large as the cross-sectional area $F_B$ of the largest (in terms of the cross-sectional area thereof) passage orifice of the crossflow mass transfer tray. Frequently, $F_A$ will be more than 10 times, or more than 100 times, or more than 1000 times, or more than 10000 times or in some cases even more than $10^6$ times $F_B$ (for example in the case of crossflow sieve trays). In crossflow hood trays among others, $F_A$ will frequently not be more than $20 \times F_B$ or not more than $15 \times F_B$ or not more than $10 \times F_B$.

The total area of the cross-sectional areas of the downflow orifices of the at least one downcomer of a crossflow mass transfer tray within an inventive sequence of crossflow mass transfer trays is, appropriately in application terms, such that it is normally not more than 20% (but at least 0.2% or preferably at least 0.5%), preferably 0.5 to 10% and more preferably 1 to 5% of the cross-sectional area (preferably circle area) of the crossflow mass transfer tray.

It is essential to the invention that, within an inventive sequence of crossflow mass transfer trays, the lower of two successive crossflow mass transfer trays in each case, in the direction of crossflow from the at least one feed thereof to the at least one downcomer thereof, has passage orifices not only in the region between the at least one feed and the at least one downcomer (these passage orifices shall be referred to in this document as passage orifices A), but also additionally at least one (or more than one) passage orifice beyond at least one downcomer (these passage orifices shall be referred to in this document as passage orifices B).

Advantageously in accordance with the invention, the aforementioned lower crossflow mass transfer tray additionally also has, beyond more than one of the downcomers present, at least one passage orifice (B) or more than one passage orifice (B) for the at least one ascending gas.

Particularly advantageously in accordance with the invention, the aforementioned lower crossflow mass transfer tray additionally also has, beyond at least one third of the downcomers present, at least one passage orifice (B) or more than one passage orifice (B) for the at least one ascending gas.

Very particularly advantageously in accordance with the invention, the aforementioned lower crossflow mass transfer tray additionally also has, beyond at least half or beyond each of the downcomers present, at least one passage orifice (B) or more than one passage orifice (B) for the at least one ascending gas.

Advantageously in accordance with the invention, the passage orifices B correspond to the passage orifices A (in terms of shape and cross-sectional area (together=cross section), apart from edge regions of the crossflow mass transfer tray), including the configuration thereof as a mere sieve passage orifice, or as a valve passage orifice, or as a bubble-cap passage orifice. In principle, in the process according to the invention, the passage orifices B may, however, also be different and/or of different configuration than the passage orifices A (which are preferably identical in terms of shape, cross-sectional area and configuration, apart from passage orifices A in edge regions of the crossflow mass transfer tray).

In the case that the at least one passage orifice B differs from at least a portion of the passage orifices A in terms of shape (geometry) and/or cross-sectional area, it is advantageous in accordance with the invention when at least one of the following relationships applies between the greatest dimension $G_B$ of a passage orifice B at right angles to the longest dimension $L_B$ of this passage orifice B, and the arithmetic mean $G_A$ formed over all passage orifices A for the greatest dimension $G_A$ of a passage orifice A at right angles to the longest dimension $L_A$ of this passage orifice A:

$$0.25\overline{G}_A \leq G_B \leq 4\overline{G}_A,$$

preferably $$0.33\overline{G}_A \leq G_B \leq 3\overline{G}_A,$$

and more preferably $$0.50\overline{G}_A \leq G_B \leq 2\overline{G}_A.$$

The longest dimension of a passage orifice is the longest direct line connecting two points on the outline of the cross section of the passage orifice, and the greatest dimension of the same passage orifice at right angles thereto is the longest direct line connecting two points on the outline of the cross section of the passage orifice which is at right angles to the longest dimension of this passage orifice.

Any different configuration of the at least one passage orifice B and of the passage orifices A tends to be the exception.

More preferably in accordance with the invention, each downcomer of a crossflow mass transfer tray used for an inventive sequence of crossflow mass transfer trays is surrounded on all sides by passage orifices (i.e. any straight line running from the center of the downflow orifice of a downcomer in any direction intersects or comes into tangential contact with at least one passage orifice).

In a crossflow mass transfer tray used in an inventive sequence of crossflow mass transfer trays, in this document, the direction of crossflow from the at least one feed onto this crossflow mass transfer tray to the at least one downcomer on this crossflow mass transfer tray is understood to mean the direction of that vector (of the "crossflow vector") which leads from the center of the entirety of all feed areas to the center of the entirety of the cross-sectional areas of all downflow orifices of the downcomers.

It is essential to the invention that crossflow mass transfer trays suitable for an inventive sequence of crossflow mass transfer trays have, viewed looking from the center of the downflow orifice of the at least one downcomer thereof in the direction of the aforementioned crossflow, passage orifices not just in the direction of this crossflow (in the direction of the crossflow vector), i.e. "in front of" the at least one downcomer, but also in the opposite direction, i.e. "beyond" the at least one downcomer.

Advantageously in accordance with the invention, the orifice ratio "in front of" the at least one downcomer corresponds essentially to that "beyond" this downcomer. This orifice ratio is understood to mean the ratio $V=G_D:G_S$ of the total cross-sectional area $G_D$ of the passage orifices present in a tray segment and the total (surface) area $G_S$ of the tray segment (in contrast to cross-sectional areas of passage orifices, cross-sectional areas of downflow orifices (and of any feed areas free of passage orifices present) are not considered to form part of a tray segment). Frequently, instead of V, the product V×100[%] is also reported.

The (surface) area of the tray or of a tray segment is understood to mean the area of that plane which prevents the liquid flowing transversely over the tray from flowing directly downward.

The spatial terms "upward" and "downward" relate, unless explicitly stated otherwise, to the orientation of the column during operation.

Otherwise, the quite general statements made in this document for crossflow mass transfer trays also apply correspondingly to crossflow mass transfer trays used in an inventive sequence of crossflow mass transfer trays.

In other words, the hydraulic seal of the at least one downcomer of a crossflow mass transfer tray used in an inventive sequence of crossflow mass transfer trays may, for example, be designed such that the downcomer is extended downward to such an extent (runs downward to such an extent) that it is immersed deep enough into the liquid present on the next lowest mass transfer tray of the sequence. The liquid level needed for this purpose is ensured on the lower crossflow mass transfer tray, for example, by the height of the outlet weirs thereof. Such a static seal is shown in FIG. 1 of this document in a schematic longitudinal section. This longitudinal section is essentially restricted to one half (one side) of the separation column, and extends over three crossflow mass transfer trays arranged one above another in an inventive sequence of crossflow mass transfer trays. As evident from FIG. 1, in this sequence, the region of the lower crossflow mass transfer tray directly below the outflow cross section of a downcomer of the crossflow mass transfer tray above (called the feed area) does not have any passage orifices for the ascending gas, and this is why this form of the hydraulic static seal is an embodiment which is less preferred in accordance with the invention.

Crossflow mass transfer trays of the embodiment just described, which are usable in accordance with the invention, are thus circular mass transfer trays which have, in one half of the circular mass transfer tray, at least one downcomer and, in the other half of the circular mass transfer tray, opposite the at least one downcomer (for example the effective mirror image of the cross-sectional area of the corresponding downflow orifice at a straight line running through the geometric center of the circular mass transfer tray), at least one feed area free of downflow orifices (onto which liquid descends in the operating state from the corresponding upper mass transfer tray).

Advantageously in accordance with the invention, mass transfer trays of such a design have at least one (or more than one) passage orifice (for the at least one ascending gas in the operating state) not only (looking) in the direction of crossflow from the at least one feed area to the at least one downcomer "beyond" at least one downcomer, but also in the opposite direction to the crossflow (viewed from the at least one downcomer) "beyond" at least one feed area (in addition to the passage orifices A in the region between the at least one feed area and the at least one downcomer).

Passage orifices "beyond" a feed area shall be referred to in this document as passage orifices B*.

Advantageously in accordance with the invention, the mass transfer tray designed as described above additionally also has, "beyond" more than one of the feed areas present, at least one passage orifice (B*) or more than one passage orifice (B*) for the at least one ascending gas.

Advantageously in accordance with the invention, the mass transfer tray designed as described above additionally also has, "beyond" at least one third of the feed areas present, at least one passage orifice (B*) or more than one passage orifice (B*) for the at least one ascending gas.

Very particularly advantageously in accordance with the invention, the mass transfer tray designed as described above additionally also has, "beyond" at least half or "beyond" each of the feed areas present, at least one passage orifice (B*) or more than one passage orifice (B*) for the at least one ascending gas.

Advantageously in accordance with the invention, the passage orifices B* (and also the passage orifices B) correspond to the passage orifices A (in terms of shape and cross-sectional area, apart from the edge regions of the mass transfer tray), including the configuration thereof as a mere sieve passage orifice, or as a valve passage orifice, or as a bubble-cap passage orifice. In principle, in the process according to the invention, the passage orifices B* may, however, also be different and/or differently configured than the passage orifices A (which are preferably identical in terms of shape, cross-sectional area and configuration, apart from passage orifices A in edge regions of the mass transfer tray) and/or than the passage orifices B.

In the case that the at least one passage orifice B* differs in terms of shape (geometry) and/or cross-sectional area from at least a portion of the passage orifices A, it is advantageous in accordance with the invention when at least one of the following relationships applies between the greatest dimension $G_B^*$ of a passage orifice B* at right angles to the longest dimension $L_B^*$ of this passage orifice B*, and the arithmetic mean $\overline{G}_A$ of the greatest dimension $G_A$ of a passage orifice A at right angles to the longest dimension $L_A$ of this passage orifice A, formed over all passage orifices:

$$0.25\overline{G}_A \leq G_B^* \leq 4\overline{G}_A,$$

preferably $$0.33\overline{G}_A \leq G_B \leq 3\overline{G}_A,$$

and more preferably $$0.50\overline{G}_A \leq G_B \leq 2\overline{G}_A.$$

Any different configuration of the at least one passage orifice B* and of the passage orifices A tends to be the exception.

Appropriately in accordance with the invention, passage orifices B, A and B* of a mass transfer tray configured as described have a homogeneous design (apart from edge regions).

More preferably in accordance with the invention, each feed area of a mass transfer tray as described above is surrounded on all sides by passage orifices.

Preferably in accordance with the invention, the orifice ratio in the region between the at least one downcomer and the at least one feed area of a mass transfer tray designed as described above corresponds to that "beyond" the at least one feed area.

For the rest, the reference numerals of FIG. 1 are defined as follows:
1: downcomer;
2: passage orifice;
3: downflow orifice of a downcomer;
4: feed area;
5: wall of the separation column; and
6: mass transfer tray.

In the embodiment preferred in accordance with the invention of the hydraulic seal of the at least one downcomer of a crossflow mass transfer tray used in an inventive sequence of crossflow mass transfer trays, the lower outflow end of the downcomer is truncated to such an extent (ends such that) it is not immersed into the liquid on the crossflow mass transfer tray below.

In this case, a sufficiently large intermediate space remains between the lower end of the at least one downcomer and the crossflow mass transfer tray onto which the downcomer leads, in which a froth layer can form and heat and mass transfer can take place between a liquid layer which accumulates on the feed area and a gas ascending through passage orifices present in the feed area. In the embodiment preferred in accordance with the invention of the configuration of a truncated at least one downcomer, the "feed area" of the at least one downcomer therefore also has passage orifices on the crossflow mass transfer tray below.

A static liquid seal of the at least one downcomer with the aid of a collecting cup mounted below the outflow end of the downcomer is preferred in accordance with the invention. Appropriately in application terms, in this case, the outer wall of the collecting cup is truncated to such an extent that the outflow end of the downcomer is immersed into (projects into) the collecting cup. In the course of operation of the column, the liquid flowing downward through the downcomer collects in the collecting cup until it flows over the upper edge of the outer wall of the collecting cup. The lower edge of the downcomer is immersed into the liquid present in the collecting cup, and the collecting cup forms a siphon-like liquid seal of the downcomer.

Figure 2:
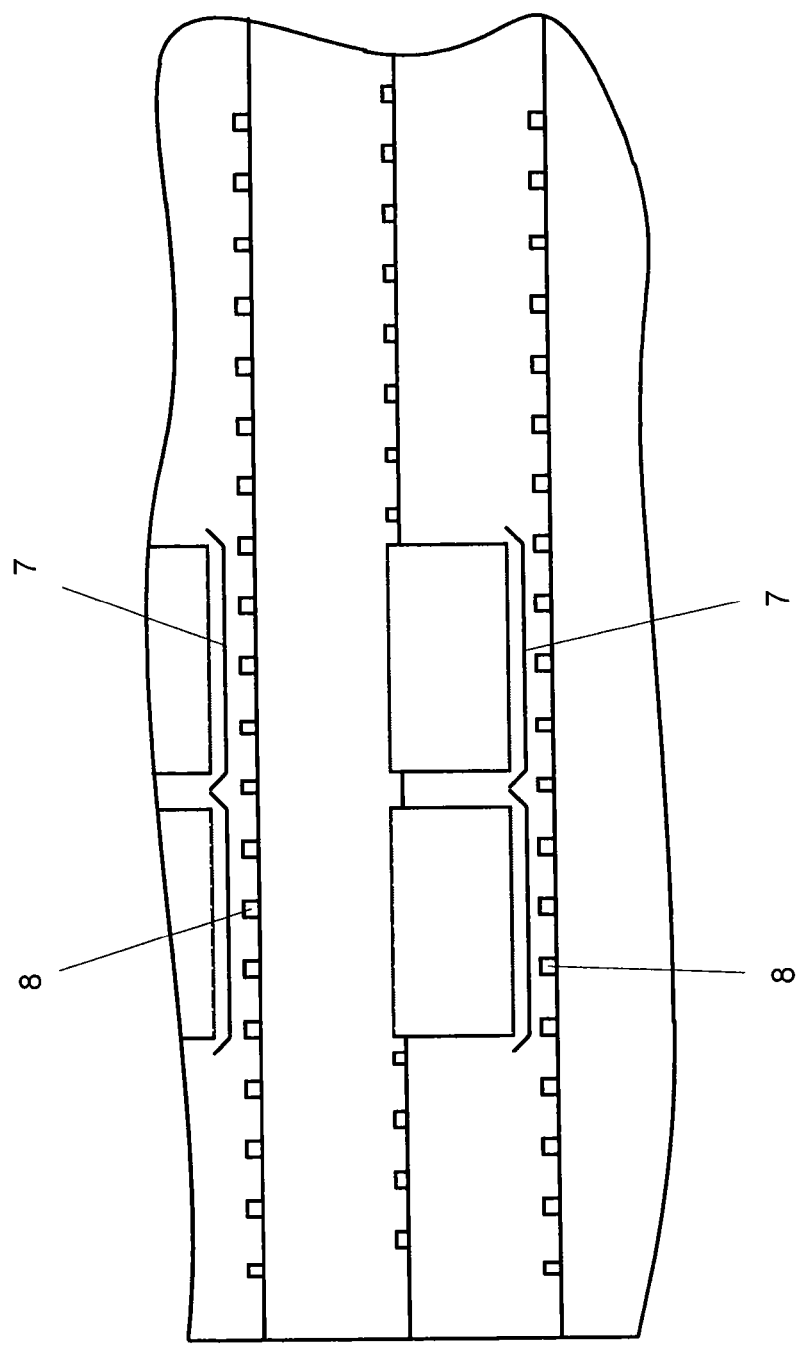
FIGS. 2-4 show alternative views of a schematic longitudinal section of an inventive sequence of inventive crossflow mass transfer trays.

FIG. 2 of this document shows a schematic longitudinal section of a section from an inventive sequence of inventive crossflow mass transfer trays, in which the at least one downcomer is truncated and is hydraulically sealed in each case by means of a collecting cup mounted below the outflow end thereof. Reference numeral 7 (the numeric address 7) in FIG. 2 shows a collecting cup in schematic longitudinal section. The numeric address 8 in FIG. 2 shows a passage orifice present in a feed area. The longitudinal section of FIG. 2 is essentially restricted again to one half (to one side) of the separation column and extends again over three crossflow mass transfer trays arranged one above another in an inventive sequence of crossflow mass transfer trays.

As an alternative to the static seal of the at least one truncated downcomer according to FIG. 2 in this document by means of a collecting cup, FIG. 3 of this document shows the corresponding schematic longitudinal section of a section from an inventive sequence of inventive crossflow mass transfer trays, except that the at least one truncated downcomer has a simple embodiment of a dynamic seal. For this purpose, the particular downcomer is provided at its lower end with a plate provided with exit orifices (one useful plate of this kind is, for example, a perforated sheet (sieve)), the dimensions of which are such that, in the operating state, liquid descending in the downcomer is backed up therein and the penetration of (ascending) gas is prevented. The shaft seal in this case is brought about by the pressure drop that the liquid backed up in the downcomer experiences (suffers) in the course of exit thereof through the exit orifices. The reference numeral 9 (the numeric address 9) in FIG. 3 shows a schematic view of such a sieve.

Another possible configuration for the dynamic sealing of a truncated downcomer of an inventive crossflow mass transfer tray suitable for an inventive sequence of crossflow mass transfer trays is shown by FIG. 4 of this document in a longitudinal section corresponding to FIGS. 1 to 3. In this configuration, the particular (truncated) downcomer has, at its lower end, a plate which does not have any exit orifices, but is mounted an exit gap width below the outlet of the downcomer. The pressure drop associated with the exit of the liquid backed up in the downcomer through the exit gap brings about the hydraulic seal here. The reference numeral 10 of FIG. 4 shows the exit gap in schematic form. The reference numeral 11 of FIG. 4 shows the plate not having any exit orifice of a truncated downcomer in schematic form.

The numeric address 12 of FIG. 4 shows, for the middle of the three crossflow mass transfer trays shown schematically, in the direction of crossflow, passage orifices present "in front of" the at least one downcomer, and numeric address 13 of FIG. 4 shows, for the same crossflow mass transfer tray, in the direction of crossflow, passage orifices present "beyond" the at least one downcomer (in each case for gas ascending in working operation).

The at least one feed onto this middle of the three inventive crossflow mass transfer trays shown schematically in FIG. 4 is in the right-hand half of the separation column, which is not shown in the schematic diagram in FIG. 4.

FIGS. 1 to 4 do not show separate outlet weirs. This function is instead fulfilled by the neck (for example, in schematic terms, the numeric address 14 in FIG. 4) of the downflow orifice extended in the upward direction. If the passage orifices are designed as bubble-cap passage orifices, the neck lengths selected for downflow and passage orifices, appropriately in application terms, are substantially the same (disregarding measures for compensating for the gradient of the level of the liquid backed up which exists over the tray).

The present invention thus comprises, more particularly, (crossflow) mass transfer trays which have circular passage orifices (having a circular cross section) and which have at least one downcomer with a downflow orifice only in one half and do not have any feed area free of passage orifices in the half opposite this half, and which are characterized in that they have passage orifices for gas ascending in working operation, proceeding from the center of the downflow orifice of the at least one downcomer, not only in the tray area in front of the at least one downcomer in the direction of the opposite half, but also in the tray area beyond the at least one downcomer in the opposite direction.

More preferably in accordance with the invention, the at least one downcomer of the above (crossflow) mass transfer tray is surrounded on all sides by passage orifices. In other words, in the embodiment particularly preferred in accordance with the invention, the above (crossflow) mass transfer tray has at least one or more than one passage orifice in all directions proceeding from the center of the downflow orifice of the at least one downcomer in the tray area surrounding it.

Advantageously, the at least one downcomer (all downcomers or downflow orifices thereof) of such a preferably circular (crossflow) mass transfer tray is/are in a circle segment of the (crossflow) mass transfer tray, the area of which is not more than five sixths, preferably not more than four fifths and particularly advantageously not more than three quarters or not more than two thirds of half of the circle area of the (crossflow) mass transfer tray. In general, the area of this circle segment is, however, at least one fifth or at least one quarter of half of the circle area of the (crossflow) mass transfer tray.

Normally, the (crossflow) mass transfer tray which has been detailed above and is preferred in accordance with the invention has more than one downcomer. For example, the number of downcomers may be two, or three, or four, or five, or six, or seven, or eight, or nine, or ten.

In general, the aforementioned number of downcomers will not be more than twenty, typically not more than fifteen.

It is advantageous when the distance between the center of the downflow orifice of the at least one downcomer (of each of the downcomers) and the geometric center of the circular, above-detailed (crossflow) mass transfer tray is at least as long as one third of the radius, preferably at least as long as two fifths of the radius and more preferably at least as long as half the radius or at least as long as three fifths of the radius of the (crossflow) mass transfer tray. The shortest distance between the outline of the at least one downcomer and the outline of the aforementioned (crossflow) mass transfer tray is, advantageously in accordance with the invention, such that it satisfies the space required by at least one passage orifice, preferably at least two passage orifices.

Within an abovementioned circle segment, the downcomers or the downflow orifices thereof in such a (crossflow) mass transfer tray are advantageously arranged such that there is no further downflow orifice on a straight line which leads from the center of a downflow orifice to the geometric center of the (crossflow) mass transfer tray (i.e. the straight line does not intersect or have any tangential contact with a further downflow orifice).

In addition, the distribution of the downflow orifices within the circle segment of such an inventive (crossflow) mass transfer tray is advantageously undertaken such that the shortest direct connecting line from the center of any downflow orifice to a point on the circumference (on the circumference line, on the outline) of the (crossflow) mass transfer tray is not longer than two thirds of the radius, preferably not longer than three fifths of the radius, more preferably not longer than half the radius or than two fifths of the radius of the (crossflow) mass transfer tray.

Appropriately in accordance with the invention, the downflow orifices of the downcomers of an above-detailed (crossflow) mass transfer tray have a uniform cross section (including the cross-sectional area). This may, for example, be circular, rectangular, square, or that of an elongated hole. With regard to the other features of a downcomer too, the downcomers of an above-detailed (crossflow) mass transfer tray are designed in a uniform manner, advantageously in accordance with the invention.

It is also the case for the above-detailed inventive (crossflow) mass transfer trays that the cross-sectional area $F_A$ of the downflow orifice belonging to a downcomer is normally at least twice as great as the cross-sectional area $F_B$ of the largest passage orifice of the (crossflow) mass transfer tray. Frequently, $F_A$ here too will be more than 10 times, or more than 100 times, or more than 1000 times, or more than 10000 times or in some cases even more than $10^6$ times $F_B$ (for example in the cases of crossflow sieve trays). In the case of crossflow hood trays among others, $F_A$ here too will frequently be not more than $20 \times F_B$ or not more than $15 \times F_B$ or not more than $10 \times F_B$.

The total area of the cross-sectional areas of the downflow orifices of the at least one downcomer of a (crossflow) mass transfer tray as detailed above is, appropriately in application terms, normally also such that it is not more than 20% (but at least 0.2% or preferably at least 0.5%), preferably 0.5 to 10% and more preferably 1 to 5% of the circle area of the (crossflow) mass transfer tray.

Equally, the passage orifices of an inventive (crossflow) mass transfer tray as detailed above, apart from edge regions of the tray, are, appropriately in application terms, configured uniformly (identically). In other words, normally (as far as permitted by the size ratio of passage orifice and cross section of the tray) at least 20%, preferably at least 30%, more preferably at least 40% or at least 50%, and most preferably at least 60% or at least 70%, or at least 80% of all passage orifices of such a crossflow mass transfer tray have a uniform cross section (the high percentages generally exist in separation columns with large cross section (diameter of, for example, >2 m) and the lower percentages in separation columns with small cross section (diameter of, for example, <2 m), since, in the case of the latter, the edge regions are of greater weight and may not permit a higher percentage). This (such uniformity) likewise applies to corresponding necks, bubble caps, valves, etc., apart from any measures which are taken to counteract a liquid gradient on the crossflow mass transfer tray in the operating state.

The cross section of a passage orifice of an inventive (crossflow) mass transfer tray as detailed above may, as is also the case for other (crossflow) mass transfer trays suitable in accordance with the invention, be circular, polygonal (e.g. triangular, square or rectangular) or correspond to the cross section of an elongated hole.

Advantageously in application terms, the passage orifices of an inventive (crossflow) mass transfer tray as detailed above are regularly arranged as already detailed in this document for crossflow mass transfer trays suitable in accordance with the invention.

Useful configurations of passage orifices of an inventive (crossflow) mass transfer tray as detailed above include all sieve passage orifices, bubble-cap passage orifices and/or valve passage orifices detailed in this document.

In principle, in the case of inventive circular (crossflow) mass transfer trays which have at least one downcomer only in one half and have no feed area free of passage orifices in the half opposite this half, the passage orifices, present in front of the at least one downcomer in the direction of the opposite half proceeding from the center of the downflow orifice of the at least one downcomer, may also be different at least than a portion of the passage orifices present beyond the at least one downcomer in the opposite direction in terms of cross section (including the cross-sectional area) and/or configuration. If the former are again referred to by the letter A and the latter by the letter B, it is also the case here that the statements made elsewhere in this document for passage orifices A, B apply correspondingly.

The at least one downcomer of an inventive (crossflow) mass transfer tray as detailed above may have construction features of a dynamic or static seal, as already described in this document for a truncated downcomer. Preferably in accordance with the invention, the at least one downcomer ends in a collecting cup mounted below the lower end thereof, which, in the context of an inventive use of the (crossflow) mass transfer tray, results in (causes) the static seal thereof.

Quite generally, useful passage orifices for (crossflow) mass transfer trays suitable in accordance with the invention are especially the bubble-cap passage orifices (hood passage orifices) having forcing slots of DE 10243625 A1. Within an inventive sequence of identical crossflow mass transfer trays, the arrangement and configuration of the aforementioned passage orifices in the region between the at least one feed and the at least one downcomer of a crossflow mass transfer tray, appropriately in application terms, follows the recommendations of DE 10243625 A1.

The details given so far are to be illustrated hereinafter, without any restriction of their generality, by specific embodiments.

Figure 5:
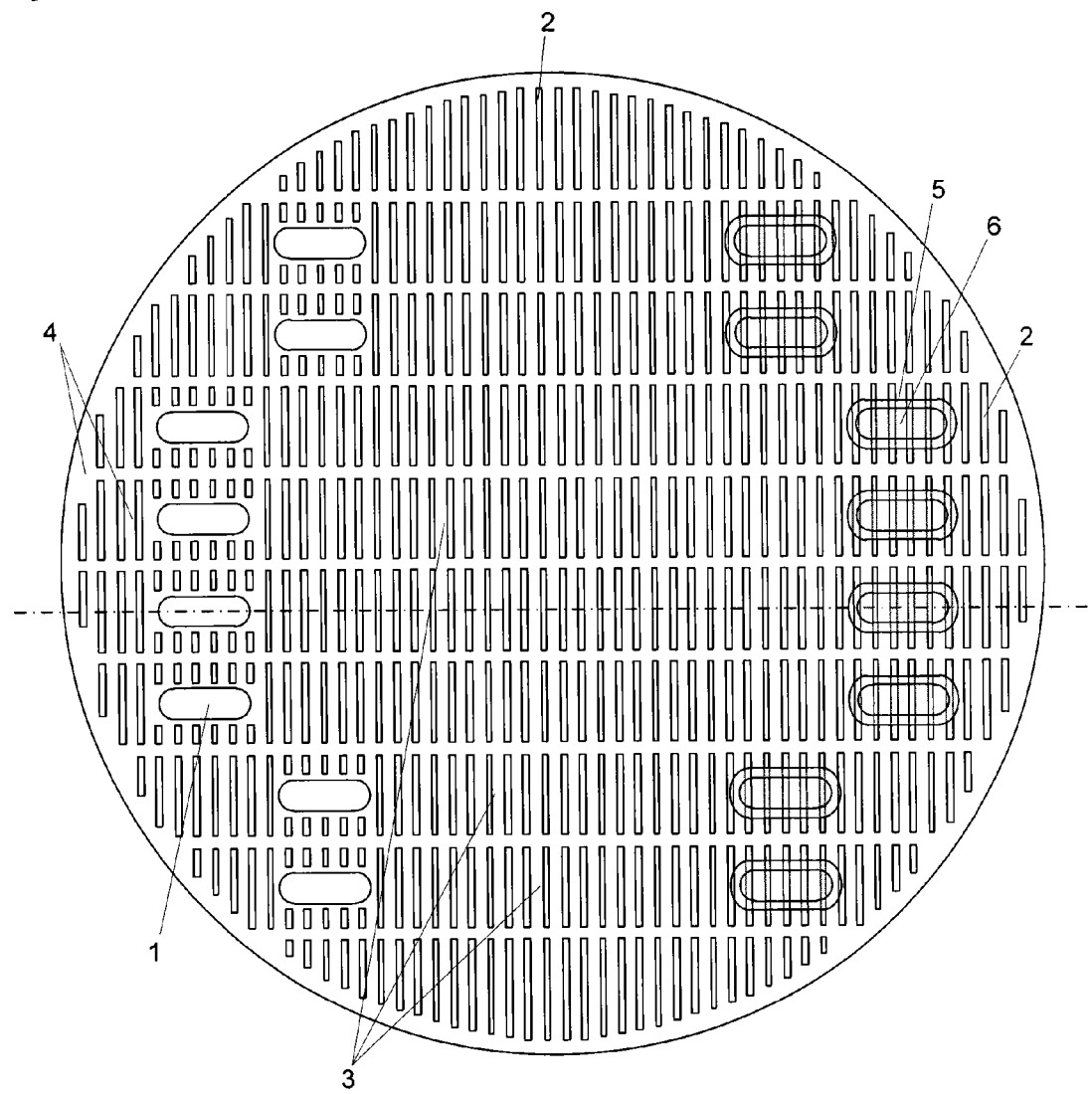
FIG. 5 is a top view of a next lowest inventive crossflow mass transfer tray arranged in an inventive sequence of crossflow mass transfer trays.

FIG. 5 of this document shows, for this purpose, the top view (from the top) of a "next lowest" inventive crossflow mass transfer tray arranged in an inventive sequence of (identical) crossflow mass transfer trays (the numeric addresses used hereinafter relate to FIG. 5).

The sequence is within a separation column, the relevant internal diameter of which is 7.40 m. This is also the diameter of the crossflow mass transfer tray shown. FIG. 5 does not show the subject depicted to scale, but merely schematically. However, the number of elements shown in FIG. 5 and the pattern of their relative arrangement is true to reality. The dimensions of the elements reported hereinafter can therefore be used to discern the quantitative configuration, the quantitative structure of what is shown in FIG. 5.

The inventive crossflow mass transfer tray shown schematically in FIG. 5 is a hydraulically sealed crossflow hood tray. It has eight identical downcomers (1). The cross section of the individual downcomer and of the accompanying downflow orifice has the geometry of an elongated hole. The elongated hole width (the diameter C) is 200 mm. The box length (the length L) of the elongated hole is 280 mm. The length in the middle of the elongated hole is thus 480 mm. The sum of the cross-sectional areas of all downflow orifices is, based on the circle area of the circular crossflow mass transfer tray, 1.8%. The function of the outlet weir is fulfilled by the neck, of length 40 mm in each case, of the correspondingly extended (with constant cross section) downflow orifice directed upward in each case. The necks of the passage orifices likewise have a length of 40 mm.

The crossflow mass transfer tray has all downcomers (downflow orifices) in one half of its circular cross-sectional area, and the other half, opposite this half, of the circular cross-sectional area thereof does not have any (corresponding) feed areas free of passage orifices (2). Each downcomer is surrounded by passage orifices in all directions proceeding from the center of the downflow orifice thereof. In other words, proceeding from the center of the downflow orifice of a downcomer, for example, both the tray area (3) "in front of" the downcomer in the direction of the opposite half and the tray area (4) "beyond" the same downcomer in the opposite direction are equipped with passage orifices (2) for gas ascending in working operation.

The orifice ratio of the crossflow mass transfer tray is, determined over the entire tray, 14%. Viewed over the various area segments of the crossflow mass transfer tray, it varies only insignificantly.

The distance between the center of a downflow orifice of a downcomer and the geometric center of the circular crossflow mass transfer tray for each downcomer is longer than three fifths of the radius of the crossflow mass transfer tray.

The downflow orifices (the downcomers) overall are within a circle segment of the crossflow mass transfer tray, the area of which is not more than two thirds of half the circle area of the crossflow mass transfer tray.

Within the circle segment, the downcomers or the downflow orifices thereof in the crossflow mass transfer tray are arranged such that there is no further downflow orifice on a straight line which leads from the center of a downflow orifice to the geometric center of the crossflow mass transfer tray (i.e. the straight line does not intersect or come into tangential contact with any further downflow orifice).

The distribution of the downflow orifices within the circle segment is additionally undertaken such that the shortest connecting line from the center of a downflow orifice to a point on the circumference (on the circumference line) of the crossflow mass transfer tray is not longer than two fifths of the radius of the crossflow mass transfer tray.

The (run) length of the downcomers is (not including the length of the neck in which the downflow orifice ends in the upward direction) a uniform 490 mm. The cross section of a downcomer does not change over its length.

The lower end (the outlet) of each of the downcomers opens into a collecting cup mounted below. The cross section of the tray of a collecting cup likewise approximates to the cross section of an elongated hole. The corresponding elongated hole width (the diameter C) is 300 mm. The box length (the length L) of the elongated hole is 280 mm. The length in the middle of the elongated hole is thus 580 mm. The particular downcomer runs into the particular collecting cup below with its cross section "congruent" to the cross-sectional area of the tray thereof. The outer wall of the particular collecting cup runs away at an angle of 45° obliquely upward (outward) from the cup base with respect to a vertical on the cup base. Each collecting cup has a depth of 100 mm. The immersion depth of a downcomer into the corresponding collecting cup is 60 mm. In other words, the distance from the lower end of a downcomer to the base of the collecting cup which receives the downcomer is 40 mm.

A projection of the downcomers and collecting cups of the crossflow mass transfer tray arranged immediately above the "next lowest" inventive crossflow mass transfer tray shown in FIG. 5 in the inventive sequence of (identical) crossflow mass transfer trays onto the crossflow mass transfer tray shown in FIG. 5 shows, in schematic form, the numeric addresses 5 (projection of a collecting cup) and 6 (projection of a downcomer) of FIG. 5.

The passage orifices are, apart from edge regions of the crossflow mass transfer tray or of the downcomers, of uniform (normal) geometry. The cross section thereof is that of a rectangle. The longer rectangle side (the long edge, the long side) is 580 mm in length, and the shorter rectangle side (the transverse side, the end side) is 56 mm in length. In the edge region of the separation column (of the circular crossflow mass transfer tray), the length of the longer rectangle side decreases down to 178 mm. Viewed over the crossflow mass transfer tray, the passage orifices within ten rows (columns) arranged regularly alongside one another are arranged in equidistant succession, with the long edge thereof aligned at right angles to the crossflow direction. Various columns (rows) of passage orifices present at one level form a line of passage orifices (the length of one line (the number of passage orifices present in one line) varies over the crossflow mass transfer tray). In total, the crossflow mass transfer tray has 52 lines. The shortest line comprises two and the longest line comprises, in accordance with the number of columns on the crossflow mass transfer tray, ten passage orifices.

The separation of the mutually opposite long edges of two immediately successive passage orifices within such a row (column) is 64 mm.

The distance between two mutually opposite end sides of two rectangular passage orifices present at the same level (in the same line) in adjacent rows is 90 mm.

The vapor deflecting hoods pulled over the necks of the rectangular passage orifices are not shown in FIG. 5. They likewise have a rectangular cross section (in simplified terms, they are upturned troughs). The wall thickness of the vapor deflecting hoods is 1.5 mm. Apart from edge regions of the crossflow mass transfer tray, where, for example, the hood length is altered to compensate for the roundness of the crossflow mass transfer tray (in principle, it can be reduced or extended compared to the normal length, following the long edge of the passage orifices, for such comparative purposes), the hoods have a uniform cross section.

The longer rectangle side ("the length") of a normal (i.e. not shortened or extended for one of the aforementioned reasons) hood (measured on the outside) is 592 mm (long edge or else long side). The shorter rectangle side ("the width") of such a hood (the transverse side, the end side) is 74 mm in length (measured on the outside). The height of the hoods (the "trough depth") is 42 mm (measured on the inside).

The hood edge (the bubble-cap edge) along both long edges of a hood is slotted in a sawtooth-like manner. The height of the essentially u-shaped slots is 15 mm. Each slot has (as a forcing slot) a guide fin (a guide surface) ("bent-open slot" or "exposed slot"). The angle between the long edge of the hood and the respective guide surface is 30 degrees.

The ratio $V_F$ formed from the cross-sectional area $F_Q$ of a normal passage orifice and the sum $F_S$ of all slot exit surfaces of the corresponding vapor deflecting hood is 0.8 ($=V_F=F_Q/F_S$).

The hoods are each mounted (pulled over) the accompanying chimneys (necks) of the passage orifices such that the tray separation of the hoods (the respective distance from the hood roof to the tray (to the tray surface); measured in the hood) decreases stepwise in the direction of the downcomers (in the direction of crossflow) (for this purpose, the simplest method is to also use flat washers in the screw attachment of the hoods). Within a line of passage orifices, the tray separation of the hoods is always uniform (equal, constant).

Beginning with that line of passage orifices which has the greatest distance from the downcomers as the first line ("line 1"), the tray separation of the hoods over the crossflow mass transfer tray, in the direction of the downcomers, is structured as follows:

in lines 1 to 9 the tray separation of the hoods is 70 mm;
in lines 10 to 14 the tray separation of the hoods is 61 mm;
in lines 15 to 34 the tray separation of the hoods is 58 mm;
in lines 35 to 43 the tray separation of the hoods is 55 mm; and
in lines 43 to 52 the tray separation of the hoods is 52 mm.

The space between two successive lines (in crossflow direction) of hooded passage orifices forms a flow channel on the crossflow mass transfer tray. Overall, the crossflow mass transfer tray described has 51 flow channels.

That flow channel which has the greatest distance from the downcomers is the first flow channel, and the last flow channel proceeding therefrom in crossflow direction is the fifty-first flow channel.

In this flow channel pattern, the passage orifices of the crossflow mass transfer tray are equipped (hooded) with the described vapor deflecting hoods having forcing slots such that the guide surfaces of the hood slots in four successive flow channels (in crossflow direction) in each case are aligned such that the liquid which flows within these channels in inventive operation (in the course of execution of the thermal separation process according to the invention) flows in the same direction (and in the opposite direction in the four subsequent flow channels etc.), such that the liquid is conveyed (supplied) in a meandering manner from the feed thereof onto the tray to the downcomers over the entirety of the flow channels.

Vapor deflecting hoods equipped with forcing slots as described are disclosed, for example, by DE 102 43 625 A1. The advantageous possible configurations described therein can also be employed in the crossflow mass transfer tray described. For example, guide plates which project beyond the hood can be secured on the top side of at least some hoods. It is advantageous when the guide elements (guide plates) are mounted at least on those hoods which separate tray regions wherein the liquid flows in opposite directions in the flow channels in the course of inventive operation. Appropriately in application terms, the surface of the guide elements forms a right angle with the hood roof. The mounting of such vertical, usually flat guide elements on the hoods counteracts flow of the liquid over them. In addition, in the case of high gas velocities, the lower width of the hood can be increased compared to the width thereof at the roof. In other words, the lower width of the hood is, appropriately in application terms, adapted to the gas velocity contemplated in inventive operation.

The lines of the crossflow mass transfer tray suitable in accordance with the invention shown in schematic top view in FIG. 5 of this document are interrupted by channels which are at right angles to the flow channels present between two successive lines. These channels shall be referred to here as cross channels. Advantageously in accordance with the invention, the cross channels have constrictions where two tray regions adjoin one another, wherein the liquid flows in opposite directions in the flow channels in inventive operation. In the extreme case, the constriction may form an occlusion. In the simplest case, these constrictions may be formed by passage orifices and/or hoods arranged closer to one another at the end side within a line. In the aforementioned extreme case, in this variant, two such passage orifices and hoods are combined at the ends to form a single ("prolonged") gas passage orifice and hood.

In order to improve liquid feed in the cross channels between the end sides of two hoods, the upper sides of the hoods may be flattened toward their ends in the form of oblique flattened areas falling away toward the ends.

Incidentally, FIG. 5 shows that it is generally advantageous in a crossflow mass transfer tray suitable in accordance with the invention to distribute the liquid output of such a tray over more than one downcomer. The spaces created between the downcomers facilitate, in inventive operation, penetration of the liquid running onto a next lowest crossflow mass transfer tray also into the region of the passage orifices beyond the at least one downcomer in the direction of crossflow from the at least one feed thereof to the at least one downcomer thereof.

In this context, it is also advantageous when, as shown in the configuration according to FIG. 5, the longest dimension of the downflow orifice of a downcomer is aligned parallel to the crossflow direction from the at least one feed to the at least one outlet.

Figure 6:
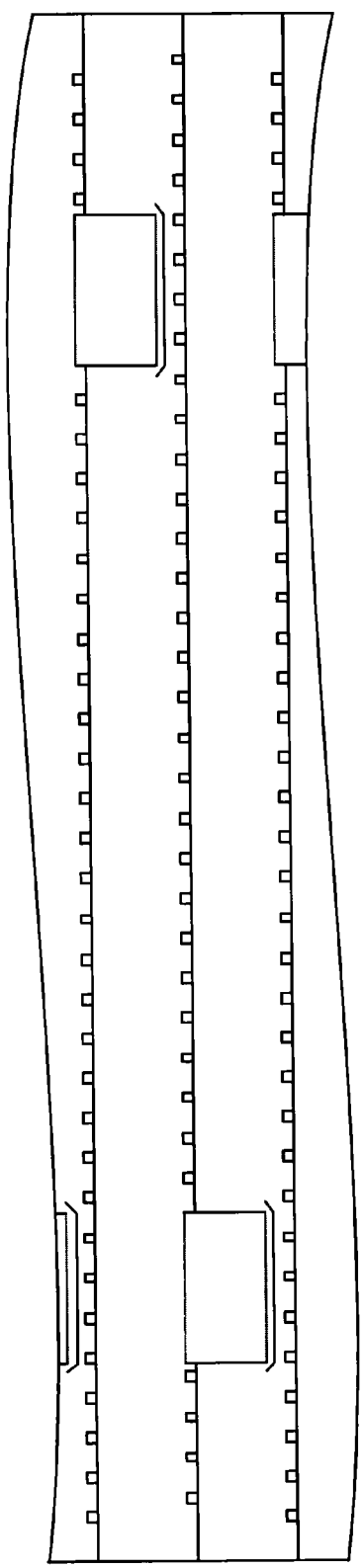
FIG. 6 is a longitudinal section running through the dotted line shown in FIG. 5.

FIG. 6 of this document shows (in analogy to FIGS. 1 to 4), in schematic form, a longitudinal section (a section) of that inventive sequence of identical crossflow mass transfer trays of which FIG. 5 shows the top view of a "next lowest" inventive crossflow mass transfer tray. The section (the longitudinal section) comprises three crossflow mass transfer trays arranged one above another. The middle of the three trays is the tray shown in top view in FIG. 5. The longitudinal section shown in FIG. 6 runs through the dotted line shown in FIG. 5.

Figure 7:
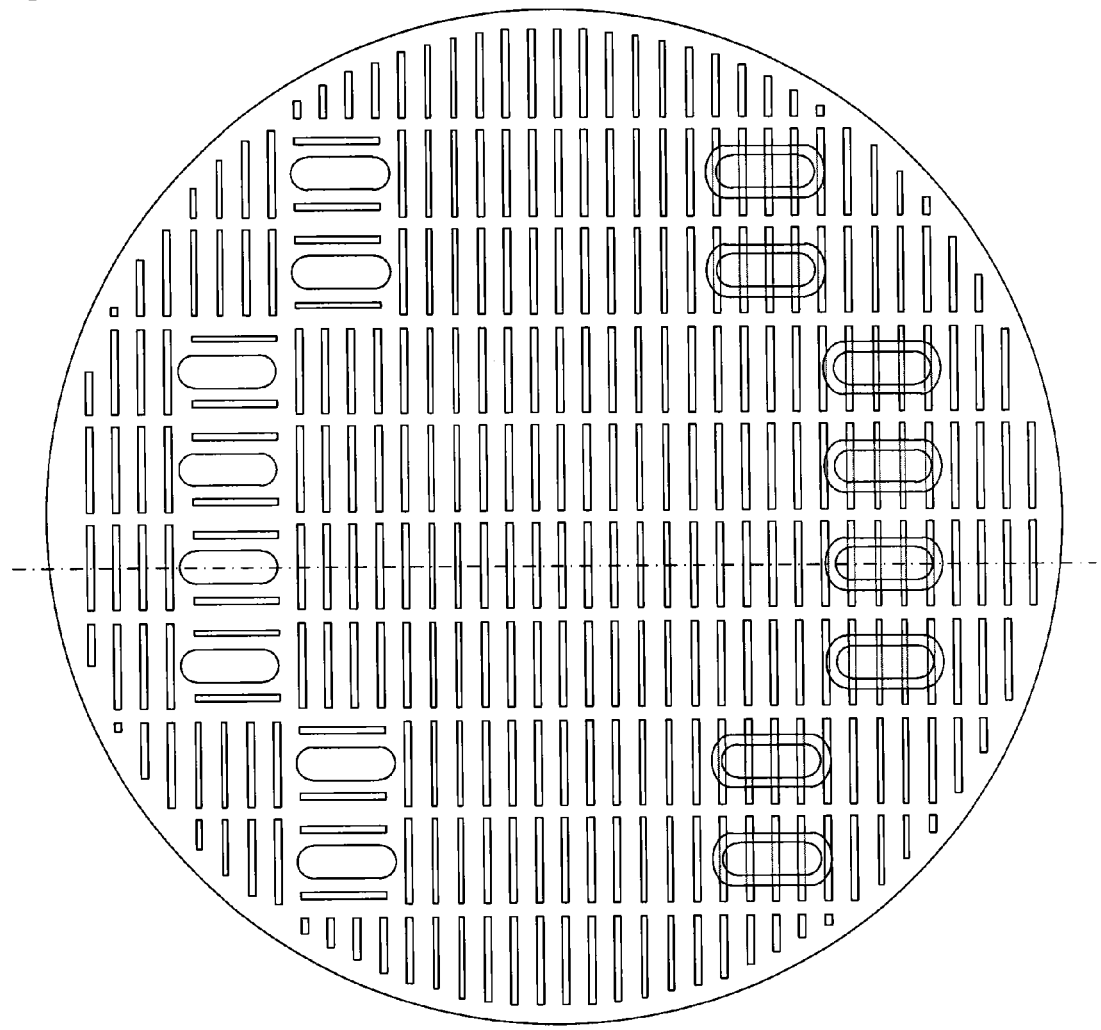
FIG. 7 is a top view of a next lowest inventive crossflow mass transfer tray arranged in another inventive sequence of crossflow mass transfer trays.

FIG. 7 of this document shows, in schematic form, the corresponding top view of a "next lowest" inventive crossflow mass transfer tray arranged in another inventive sequence of (identical) crossflow mass transfer trays. The elements shown correspond in qualitative terms to those of FIG. 5 (hoods having hood passage orifices with rectangular cross section and forcing slots, and elongated hole downcomers). The tray separations of the hoods decrease stepwise proceeding in crossflow direction from the line furthest removed from the at least one downcomer. In the lines running in crossflow direction beyond the at least one downcomer, they have a uniform, comparatively low magnitude. The passage orifices of the crossflow mass transfer tray are thus equipped (hooded) with the described vapor deflecting hoods having forcing slots such that, in four successive flow channels (in crossflow direction) in each case, the hood slots are aligned such that the liquid flowing in these channels in inventive operation (in the execution of the process according to the invention) flows in the same direction (and in the opposite direction in the four subsequent flow channels, etc.).

The crossflow mass transfer tray shown in FIG. 7 is advantageously modified compared to the crossflow mass transfer tray shown in FIG. 5, inter alia, in that a hood passage orifice mounted on both box sides in each downcomer has its long side (long edge) running parallel to the longest dimension of the downflow orifice belonging to the downcomer, and its forcing slots aligned such that, in inventive operation, the liquid is driven in crossflow direction from the at least one feed thereof to the at least one downcomer past the long side of the respective downcomer to an increased extent into the region of the passage orifices beyond the at least one downcomer (in crossflow direction).

As an alternative or additional measure to this measure, the neck length of the downflow orifices can be configured such that it is higher at the front in crossflow direction than at the back. In this way, the liquid is virtually forced, on its way from the at least one feed to the at least one downcomer, first to flow around the downcomer, and then to run into the downcomer from the back.

Figure 8:
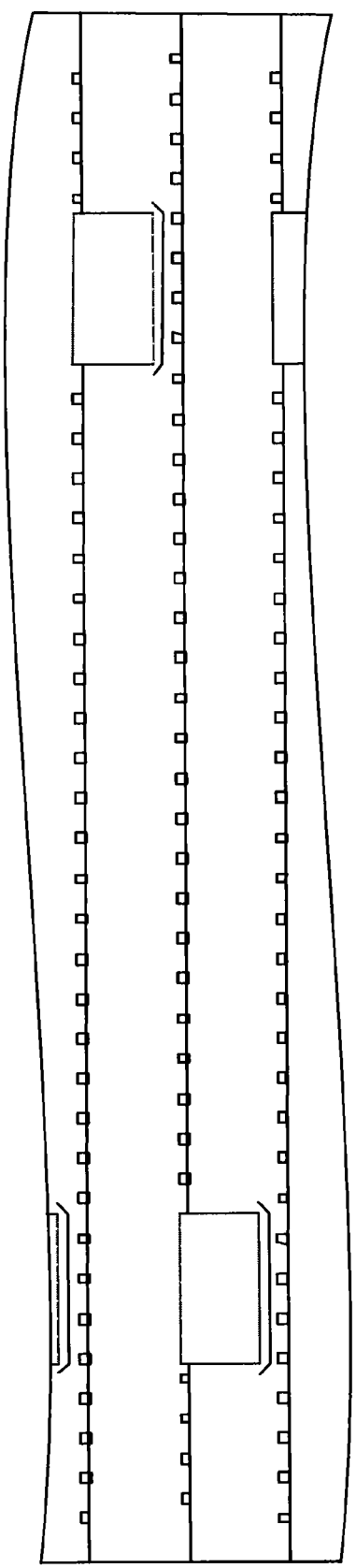
FIG. 8 is a longitudinal section running through the dotted line shown in FIG. 7.

FIG. 8 of this document shows, in schematic form, a longitudinal section (a section) of that inventive sequence of identical crossflow mass transfer trays of which FIG. 7 shows the top view of a "next lowest" inventive crossflow mass transfer tray. The section (longitudinal section) comprises three crossflow mass transfer trays arranged one above another. The middle of the three trays is the tray shown in top view in FIG. 7. The longitudinal section shown in FIG. 8 runs through the dotted line drawn in FIG. 7.

Figure 9:
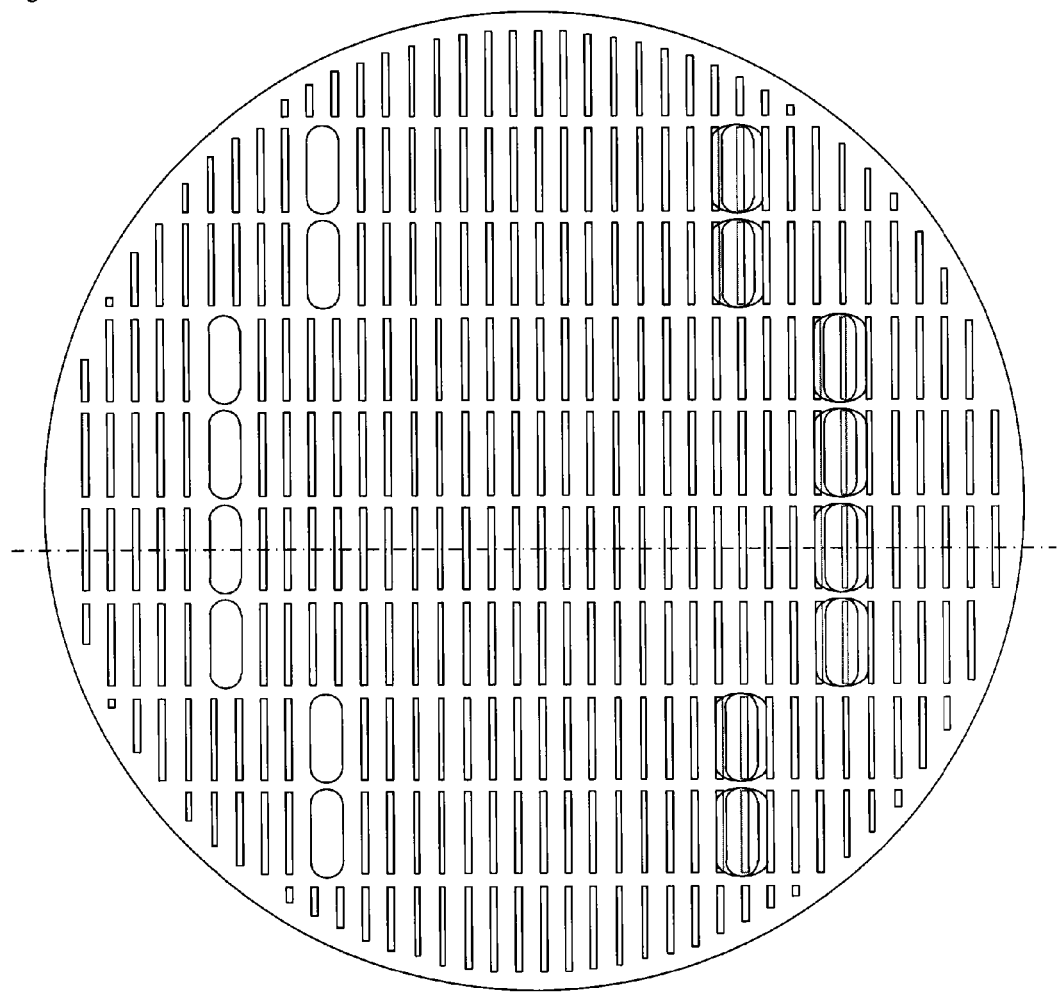
FIG. 9 is a top view of a next lowest inventive crossflow mass transfer tray arranged in another inventive sequence of crossflow mass transfer trays.

FIG. 9 of this document shows, in schematic form, the corresponding top view of a "next lowest" inventive crossflow mass transfer tray arranged in a further inventive sequence of (identical) crossflow mass transfer trays. The elements shown correspond in qualitative terms to those of FIG. 5 (hoods having hood passage orifices with rectangular cross section and forcing slots, and elongated hole downcomers). The tray separations of the hoods decrease stepwise proceeding in crossflow direction from the line furthest removed from the at least one downcomer. In the lines running in crossflow direction beyond the at least one downcomer, they have a uniform, comparatively low magnitude. The passage orifices of the crossflow mass transfer tray are thus equipped (hooded) with the described vapor deflecting hoods having forcing slots such that, in four successive flow channels (in crossflow direction) in each case, the hood slots are aligned such that the liquid flowing in these channels in inventive operation (in the execution of the process according to the invention) flows in the same direction (and in the opposite direction in the four subsequent flow channels, etc.).

As a difference from the crossflow mass transfer tray shown in FIG. 5, the downcomers of the crossflow mass transfer tray shown in FIG. 9, however, are aligned such that the longest dimension of the downflow orifice belonging to a downcomer runs parallel to the long sides (long edges) of the hood passage orifices. Inventive crossflow mass transfer trays of such a configuration are generally less preferred in accordance with the invention, since, in the course of inventive operation of a sequence of such crossflow mass transfer trays, the flow of the liquid from the at least one feed to the at least one downcomer is driven only to a comparatively reduced degree into the region of the passage orifices beyond the at least one downcomer (in crossflow direction).

Figure 10:
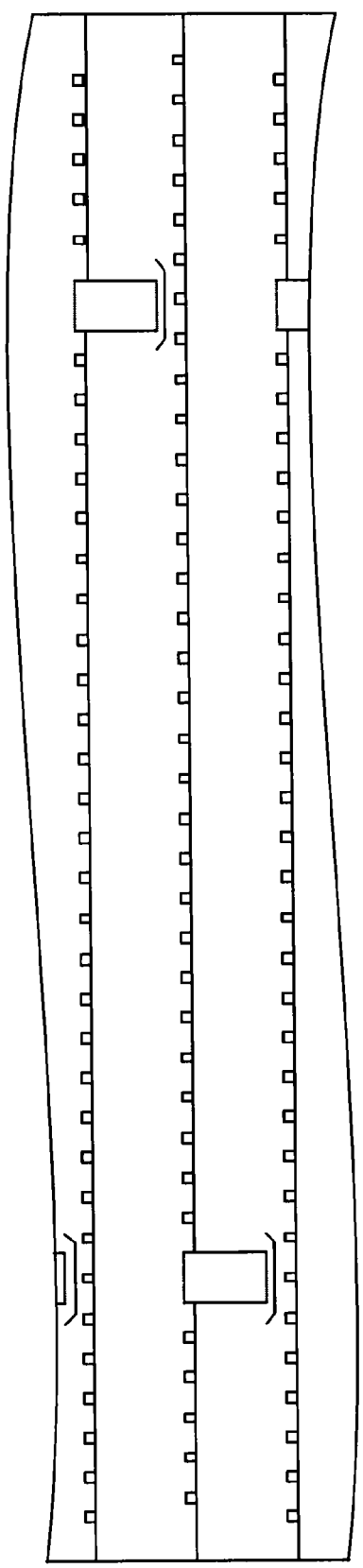
FIG. 10 is a longitudinal section running through the dotted line shown in FIG. 9.

FIG. 10 of this document shows, in schematic form, a longitudinal section (a section) of that inventive sequence of identical crossflow mass transfer trays of which FIG. 9 shows the top view of a "next lowest" inventive crossflow mass transfer tray. The section (longitudinal section) comprises three crossflow mass transfer trays arranged one above another. The middle of the three trays is the tray shown in top view in FIG. 9. The longitudinal section shown in FIG. 10 runs through the dotted line drawn in FIG. 9.

Figure 11:
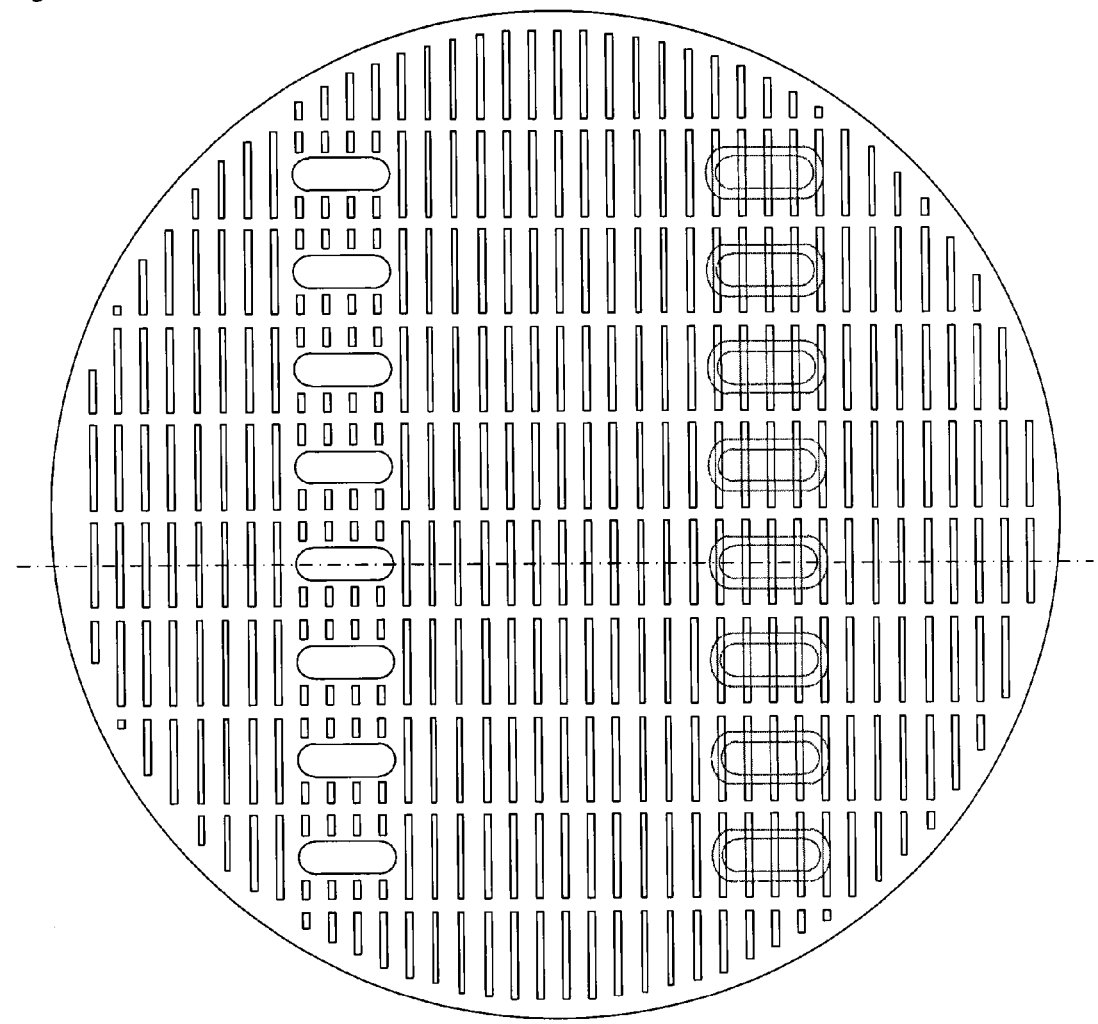
FIG. 11 is a top view of a next lowest inventive crossflow mass transfer tray arranged in another inventive sequence of crossflow mass transfer trays.

FIG. 11 of this document shows, in schematic form, the corresponding top view of a "next lowest" inventive crossflow mass transfer tray arranged in another inventive sequence of (identical) crossflow mass transfer trays. The elements shown correspond in qualitative terms to those of FIG. 5 (hoods having hood passage orifices with rectangular cross section and forcing slots, and elongated hole downcomers). The tray separations of the hoods decrease stepwise proceeding in crossflow direction from the line furthest removed from the at least one downcomer. In the lines running in crossflow direction beyond the at least one downcomer, they have a uniform, comparatively low magnitude. The passage orifices of the crossflow mass transfer tray are thus equipped (hooded) with the described vapor deflecting hoods having forcing slots such that, in four successive flow channels (in crossflow direction) in each case, the hood slots are aligned such that the liquid flowing in these channels in inventive operation (in the execution of the process according to the invention) flows in the same direction (and in the opposite direction in the four subsequent flow channels, etc.).

As a difference from the crossflow mass transfer tray shown in FIG. 5, the downcomers of the crossflow mass transfer tray shown in FIG. 11 are, however, not arranged in the manner of a half-moon (in the shape of a half-moon), but rather such that the centers of the corresponding downflow orifices are on a line running parallel to a line of passage orifices.

Figure 12:
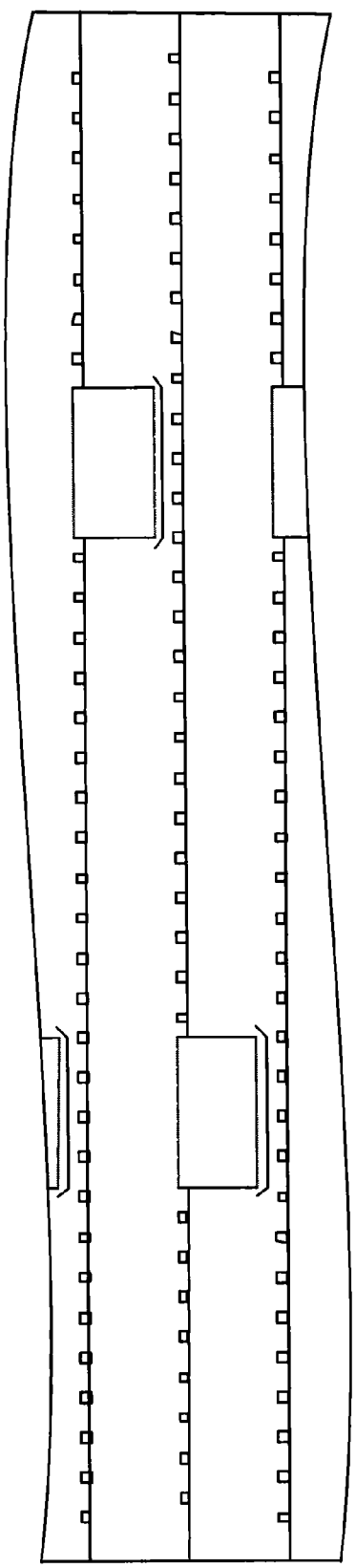
FIG. 12 is a longitudinal section running through the dotted line shown in FIG. 11.

FIG. 12 of this document shows, in schematic form, a longitudinal section (a section) of that inventive sequence of identical crossflow mass transfer trays of which FIG. 11 shows the top view of a "next lowest" inventive crossflow mass transfer tray. The section (longitudinal section) comprises three crossflow mass transfer trays arranged one above another. The middle of the three trays is the tray shown in top view in FIG. 11. The longitudinal section shown in FIG. 12 runs through the dotted line drawn in FIG. 11.

Figure 13:
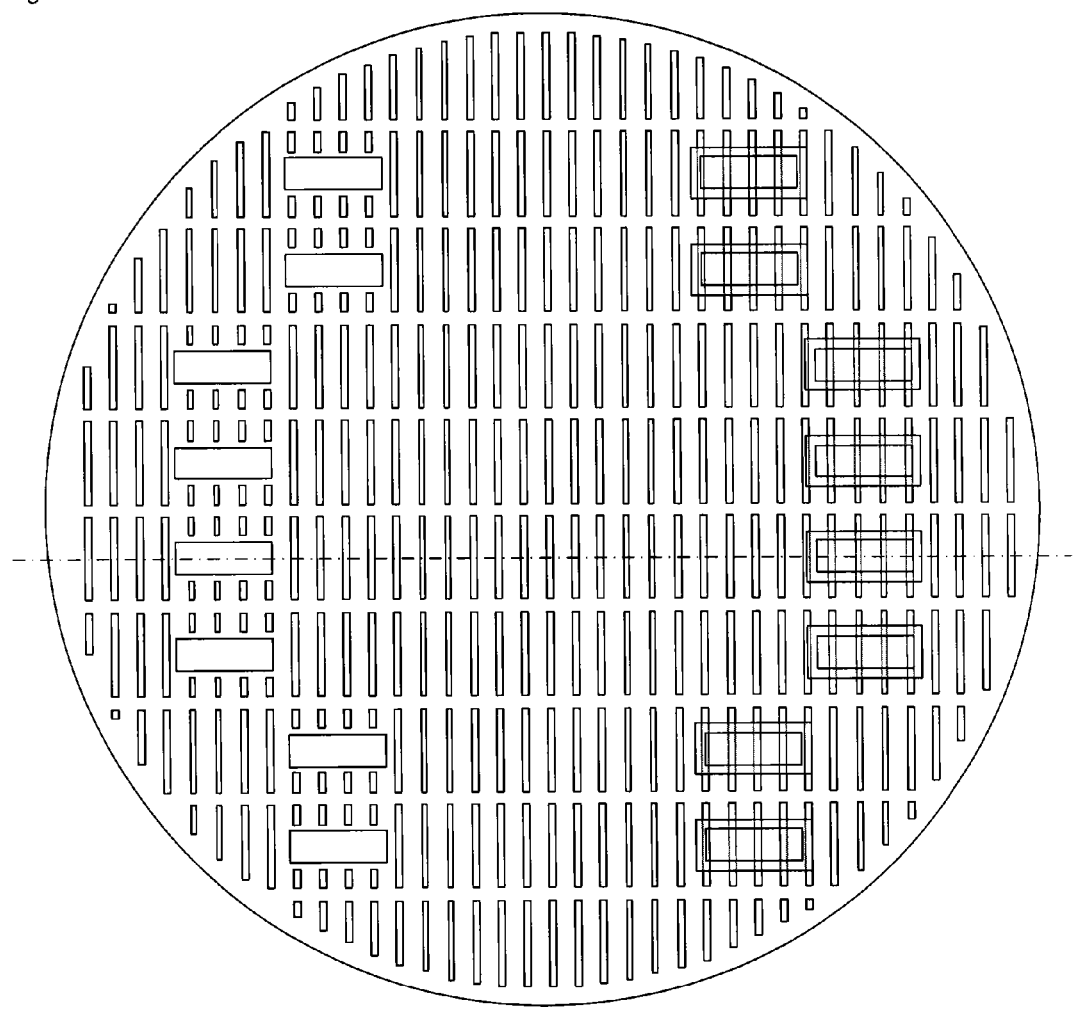
FIG. 13 is a top view of a next lowest inventive crossflow mass transfer tray arranged in another inventive sequence of crossflow mass transfer trays.

FIG. 13 of this document shows, in schematic form, the corresponding top view of a "next lowest" inventive crossflow mass transfer tray arranged in another inventive sequence of (identical) crossflow mass transfer trays. The corresponding hood passage orifices correspond in qualitative terms to those of FIG. 5 (hoods having rectangular cross section and forcing slots). The tray separations of the hoods decrease stepwise proceeding in crossflow direction from the line furthest removed from the at least one downcomer. In the lines running in crossflow direction beyond the at least one downcomer, they have a uniform, comparatively low magnitude. The passage orifices of the crossflow mass transfer tray are thus equipped (hooded) with the described vapor deflecting hoods having forcing slots such that, in four successive flow channels (in crossflow direction) in each case, the hood slots are aligned such that the liquid flowing in these channels in inventive operation (in the execution of the process according to the invention) flows in the same direction (and in the opposite direction in the four subsequent flow channels, etc.).

As a difference from the crossflow mass transfer tray shown in FIG. 5, both the downcomers of the crossflow mass transfer tray shown in FIG. 13 and the bases of the corresponding collecting cups, however, have a rectangular cross section.

Figure 14:
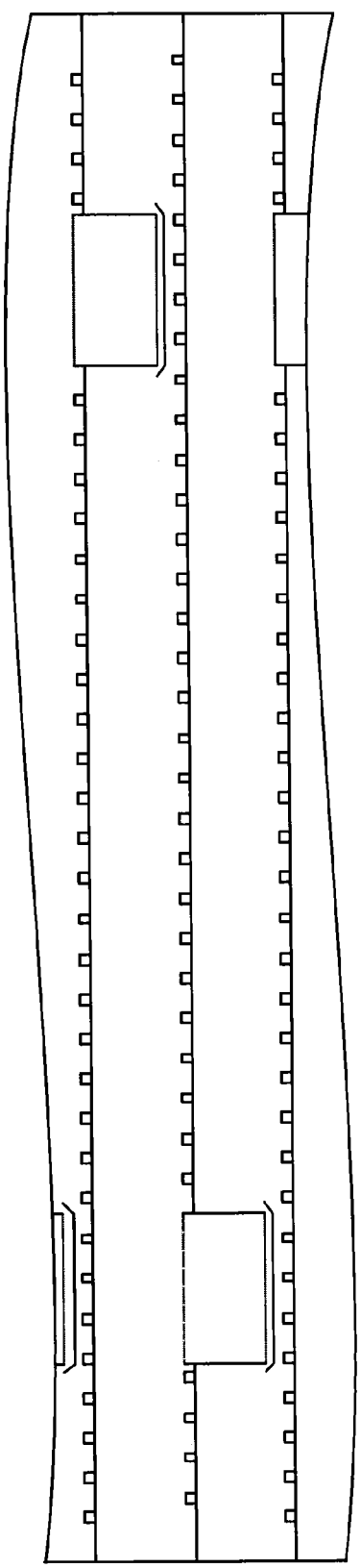
FIG. 14 is a longitudinal section running through the dotted line shown in FIG. 13.
Figure 15:
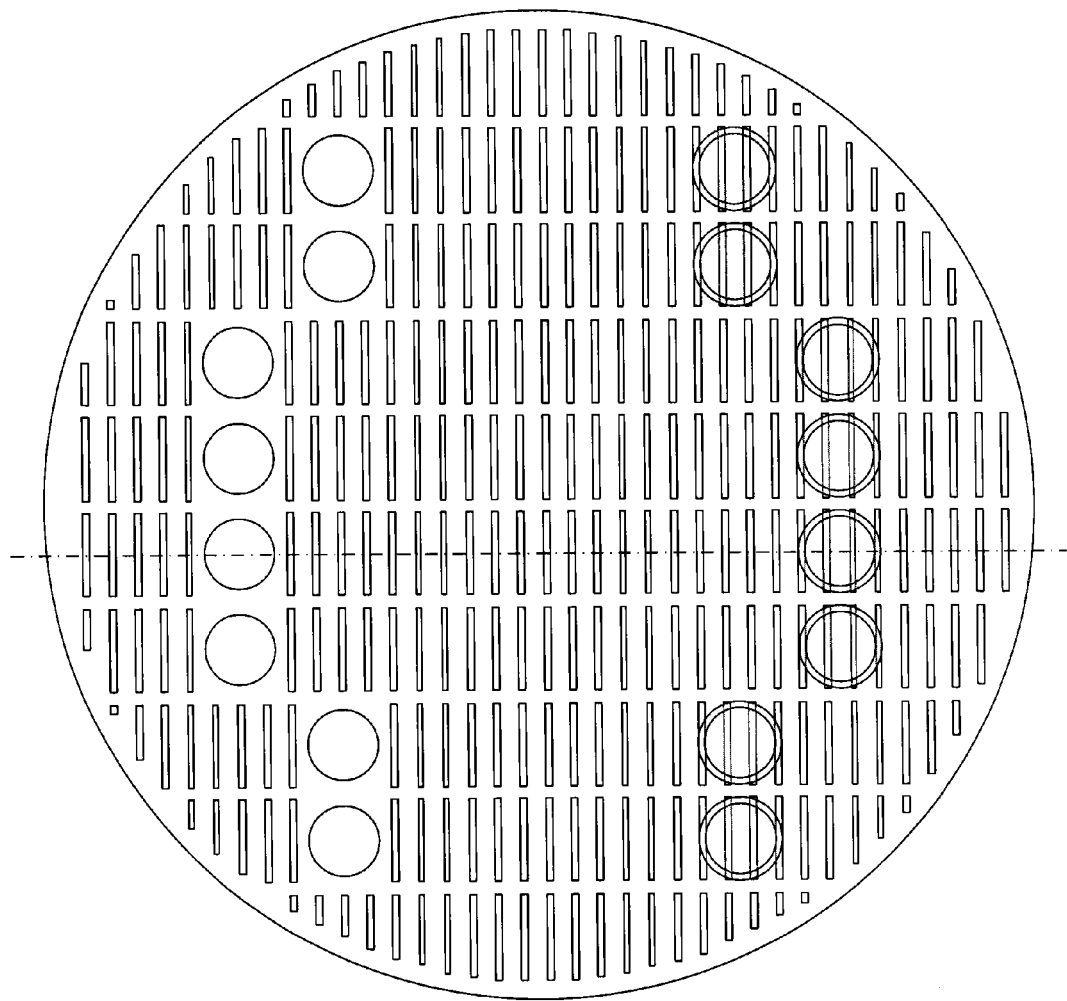
FIG. 15 is a top view of a next lowest inventive crossflow mass transfer tray arranged in another inventive sequence of crossflow mass transfer trays.

FIG. 14 of this document shows, in schematic form, a longitudinal section (a section) of that inventive sequence of identical crossflow mass transfer trays of which FIG. 13 shows the top view of a "next lowest" inventive crossflow mass transfer tray. The section (longitudinal section) comprises three crossflow mass transfer trays arranged one above another. The middle of the three trays is the tray shown in top view in FIG. 13. The longitudinal section shown in FIG. 14 runs through the dotted line drawn in FIG. 13. FIG. 15 of this document shows, in schematic form, the corresponding top view of a "next lowest" inventive crossflow mass transfer tray arranged in another inventive sequence of (identical) crossflow mass transfer trays. The corresponding hood passage orifices correspond in qualitative terms to those of FIG. 5 (hoods having rectangular cross section and forcing slots). The tray separations of the hoods decrease stepwise proceeding in crossflow direction from the line furthest removed from the at least one downcomer. In the lines running in crossflow direction beyond the at least one downcomer, they have a uniform, comparatively low magnitude. The passage orifices of the crossflow mass transfer tray are thus equipped (hooded) with the described vapor deflecting hoods having forcing slots such that, in four successive flow channels (in crossflow direction) in each case, the hood slots are aligned such that the liquid flowing in these channels in inventive operation (in the execution of the process according to the invention) flows in the same direction (and in the opposite direction in the four subsequent flow channels, etc.).

As a difference from the crossflow mass transfer tray shown in FIG. 5, both the downcomers of the crossflow mass transfer tray shown in FIG. 15 and the bases of the corresponding collecting cups, however, have a circular cross section.

Figure 16:
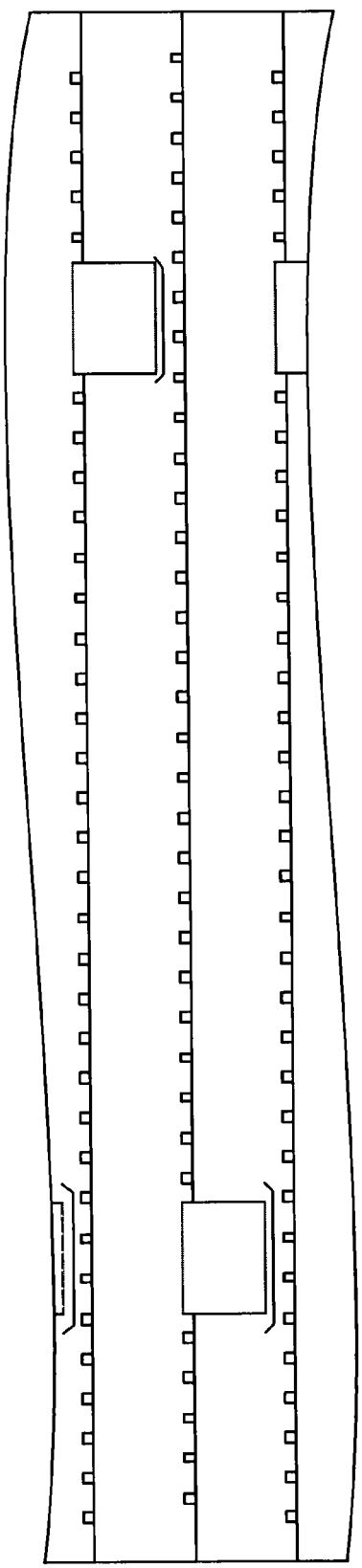
FIG. 16 is a longitudinal section running through the dotted line shown in FIG. 15.

FIG. 16 of this document shows, in schematic form, a longitudinal section (a section) of that inventive sequence of identical crossflow mass transfer trays of which FIG. 15 shows the top view of a "next lowest" inventive crossflow mass transfer tray. The section (longitudinal section) comprises three crossflow mass transfer trays arranged one above another. The middle of the three trays is the tray shown in top view in FIG. 15. The longitudinal section shown in FIG. 16 runs through the dotted line drawn in FIG. 15.

The crossflow mass transfer trays shown in FIGS. 5 to 16 have, appropriately in application terms, a tray thickness of 2 mm.

According to the statements made so far, the crossflow mass transfer trays suitable in accordance with the invention include especially hydraulically sealed crossflow mass transfer trays with circular cross section, which have at least one downcomer and flow channels which are arranged spaced apart and parallel from one another and are capable, in the course of inventive operation of a sequence of such trays, of conducting liquid which accumulates on the tray, and (gas) passage orifices which are arranged between the flow channels and are covered by longer hoods, the two lower long edges of a hood in the course of inventive operation of a sequence of such trays being immersed into liquid conducted in the flow channels and having gas exit slots with guide surfaces which, in said inventive operation, conduct the gas exit into the liquid in an oblique direction in order to produce the direction of the liquid flows in the flow channels, with the proviso that the longer side of the hood is aligned at right angles to the crossflow direction of the liquid and, in each case in at least two (preferably in at least three, or in at least four, or in at least five, or in at least six) successive flow channels in crossflow direction, the guide surfaces of the hoods are aligned such that the liquid flows in the same direction in these channels, and the liquid is otherwise conducted in a meandering manner over the entirety of the flow channels, and wherein, in accordance with the invention, the at least one downcomer is in one half of the crossflow mass transfer tray and they have, in the direction of the crossflow of liquid which is established in the course of said inventive operation from the at least one feed to the at least one downcomer, in contrast to the teaching of DE 102 43 625 A1, at least one hooded (gas) passage orifice not just "in front of" the at least one downcomer but also "beyond" at least one downcomer. For the rest, the recommendations of DE 102 43 625 A1 for such cross flow mass transfer trays apply correspondingly in accordance with the present invention. They preferably also do not have any feed areas free of passage orifices.

The long sides of their preferably rectangular passage orifices and/or hoods are, appropriately in application terms, generally 5 to 200 cm, frequently 10 to 100 cm, and the corresponding broad side is generally 2 to 30 cm, or 2 to 20 cm, frequently 4 to 8 cm. By adjusting the angle α (>0 and ≤90 degrees) between the guide surface and long side of the hood, it is possible to counteract excessively high gas velocities and, resulting from this, excessively high liquid flows. The smaller this angle (i.e. the greater the adjustment of the gas exit slots), the greater the liquid flow.

Quite generally, in the case of dynamic sealing of the at least one downcomer of a crossflow mass transfer tray suitable in accordance with the invention, it has to be ensured that the dimensions of the individual exit orifices through which the descending liquid can leave the downcomer are not too small with regard to the cross-sectional areas thereof. Otherwise, there is a growing risk that undesirably formed polymer particles which are flushed into them block an exit orifice.

Useful materials for crossflow mass transfer trays suitable in accordance with the invention include stainless steels (e.g. 1.4301, 1.4541, 1.4401, 1.4404, 1.4571, 1.4000, 1.4435 inter alia), Hasteloy C4, aluminum, copper, titanium, Monel, and polymers, for example KERA, Diabon, PVC inter alia.

The reason for the success of the inventive procedure is probably that it ensures comparatively homogeneous all-round wetting of the tray surfaces within a sequence of crossflow mass transfer trays with descending liquid comprising polymerization inhibitor. This is the case especially when, in the course of inventive operation thereof, following the teaching of WO 2004/063138 A1, the streams are preferably adjusted so as to result in an increased proportion of entrainment.

Against this background, it is also found to be favorable when the clear distance between two immediately successive trays within an inventive sequence of crossflow mass transfer trays is not more than 700 mm, preferably not more than 600 mm or not more than 500 mm.

Inventive sequences of crossflow mass transfer trays described in this document are suitable, for example, for gas loading factors (=superficial gas velocity·root of the gas density) in the range from 0.1 $(Pa)^{0.5}$ to 3 $(Pa)^{0.5}$, and for liquid hourly space velocities in the range from 0.001 to 10 $m^3/(m^2 \cdot h)$. They can be operated under standard pressure, under reduced pressure and under elevated pressure.

The thermal separation process according to the invention may, for example, be a process for fractional condensation for removal of acrylic acid from a product gas mixture comprising acrylic acid from a heterogeneously catalyzed gas phase partial oxidation of a $C_3$ precursor compound (especially propene and/or propane) of acrylic acid with molecular oxygen to give acrylic acid.

The thermal separation process according to the invention is suitable, inter alia, for improved performance of a process for fractional condensation for removal of acrylic acid from a product gas mixture comprising acrylic acid from a heterogeneously catalyzed gas phase partial oxidation of a $C_3$ precursor compound (especially propene and/or propane) of acrylic acid with molecular oxygen to give acrylic acid in a separation column which comprises separating internals and comprises, from the bottom upward, at first dual-flow trays and then crossflow hood trays, and which is described in noninventive embodiments, for example, in documents DE 19924532 A1, DE 10243625 A1 and WO 2008/090190 A1.

The improvement in the procedures recommended in the aforementioned documents is essentially that the sequence of crossflow hood trays recommended therein is replaced by a corresponding inventive sequence of crossflow hood trays (preferably in accordance with the invention by a sequence of crossflow mass transfer trays as shown in FIGS. 5 to 16 in this document).

The term "$C_3$ precursor" of acrylic acid encompasses those chemical compounds which are obtainable in a formal sense by reduction of acrylic acid. Known $C_3$ precursors of acrylic acid are, for example, propane, propene and acrolein. However, compounds such as glycerol, propionaldehyde or propionic acid should also be counted among these $C_3$ precursors. Proceeding from these, the heterogeneously catalyzed gas phase partial oxidation with molecular oxygen is at least partly an oxidative dehydrogenation. In the relevant heterogeneously catalyzed gas phase partial oxidations, the $C_3$ precursors of acrylic acid mentioned, generally diluted with inert gases, for example molecular nitrogen, CO, $CO_2$, inert hydrocarbons and/or water vapor, are passed in a mixture with molecular oxygen at elevated temperatures and optionally elevated pressure over transition metal mixed oxide catalysts, and converted oxidatively to a product gas mixture comprising acrylic acid.

Typically, the product gas mixture comprising acrylic acid from a heterogeneously catalyzed gas phase partial oxidation of $C_3$ precursors (e.g. propene) of acrylic acid with molecular oxygen over catalysts in the solid state, based on the total amount of the specified constituents present (therein), has the following contents:

1 to 30% by weight of acrylic acid,
0.05 to 10% by weight of molecular oxygen,
1 to 30% by weight of water,
0 to 5% by weight of acetic acid,
0 to 3% by weight of propionic acid,
0 to 1% by weight of maleic acid and/or maleic anhydride,
0 to 2% by weight of acrolein,
0 to 1% by weight of formaldehyde,
0 to 1% by weight of furfural,
0 to 0.5% by weight of benzaldehyde,
0 to 1% by weight of propene, and
  as the remainder, inert gases, for example nitrogen, carbon monoxide, carbon dioxide, methane and/or propane.

The partial gas phase oxidation itself can be performed as described in the prior art. Proceeding from propene, the partial gas phase oxidation can be performed, for example, in two successive oxidation stages, as described, for example, in EP 700 714 A1 and in EP 700 893 A1. It will be appreciated, however, that it is also possible to employ the gas phase partial oxidations cited in DE 19740253 A1 and in DE 19740252 A1.

In general, the temperature of the product gas mixture leaving the partial gas phase oxidation is 150 to 350° C., frequently 200 to 300° C.

Direct cooling (for example with cooled bottoms liquid withdrawn from the condensation column described hereinafter) and/or indirect cooling cools the hot product gas mixture appropriately at first to a temperature of 100 to 180° C., before it is conducted, for the purpose of fractional condensation, into the lowermost section (the bottom) of the separation column comprising the separating internals. The operating pressure which exists in the separation column is generally 0.5 to 5 bar, frequently 0.5 to 3 bar and in many cases 1 to 2 bar.

The separation column (condensation column) can be designed as described in documents DE 10243625 A1 and WO 2008/090190 A1, apart from the fact that the separation-active sequence of crossflow hood trays used therein is replaced in accordance with the invention by an inventive sequence of crossflow hood trays (preferably in accordance with the invention by a sequence of crossflow mass transfer trays as shown in FIGS. 5 to 16 of this document).

In other words, from the bottom upward, the separation column (condensation column), appropriately in application terms, at first has at least one sequence of dual-flow trays separated from the bottom space of the separation column by a first chimney tray (designed as a collecting tray) (from this first chimney tray, for example, high-boiling condensate can be withdrawn continuously and conducted into the bottom space). The at least one sequence of dual-flow trays is interrupted by a second chimney tray (collecting tray), from which crude acrylic acid is withdrawn continuously in the side draw as a medium boiler fraction, and this normally has a purity of ≥95% by weight. Appropriately, this crude acrylic acid will be sent to further distillative (rectificative) and/or crystallizative further purification stages, and at least a portion of the bottoms liquids and/or mother liquors obtained in the course of these distillations (rectifications) and/or crystallizations will be recycled into the separation column.

The dual-flow trays are then followed by at least one inventive sequence of inventive crossflow hood trays, which are appropriately concluded by a third chimney tray (collecting tray). Above the third collecting tray are appropriately valve trays (the valves of which may either be fixed or mobile). In the space of the separation column equipped with valve trays, there condense essentially water and constituents less volatile than water and at least partly acidic constituents (e.g. residual acrylic acid, acetic acid and/or propionic acid). The condensate obtained is referred to as acid water. Acid water is withdrawn continuously from the third chimney tray.

A portion of the acid water withdrawn is recycled into the separation column at the uppermost of the inventive crossflow hood trays. A further portion of the acid water withdrawn is sent to incineration. Another portion of acid water withdrawn is, appropriately in application terms, cooled by indirect heat exchange and recycled into the separation column split between the uppermost valve tray and a valve tray positioned in about the middle between the third chimney tray and the uppermost valve tray. If crude acrylic acid withdrawn continuously from the second chimney tray is purified further by crystallization, a portion of acid water withdrawn is likewise advantageously added thereto beforehand. The acrylic acid present can be removed by extraction from the predominant amount of acid water which has been withdrawn from the separation column and not recycled into it as described in WO 2008/090190 A1, to obtain an organic extract comprising the acrylic acid in dissolved form.

Constituents more volatile than water are drawn off in gaseous form as residual gas at the top of the separation column (of the condensation column). A portion of residual gas can be recycled into the partial gas phase oxidation of the at least one $C_3$ precursor compound for dilution of the reaction gas mixture supplied to the gas phase partial oxidation. Another portion of the residual gas stream can be sent to incineration. Another substream of the residual gas can, following the teaching of WO 2008/090190 A1, be used to strip the acrylic acid out of the organic extract comprising it. The resulting acrylic acid-laden gas (and/or a residual gas substream) can in turn, following the teaching of WO 2008/090190 A1, subsequently be used for the purpose of absorbing monomeric acrylic acid formed additionally in the course of redissociation of bottoms liquid which has been conducted out of the bottom of the separation column and comprises Michael adducts of acrylic acid itself, before it can be recycled into the bottom space of the separation column (condensation column), for example together with the product gas mixture of the partial oxidation of the $C_3$ precursor compound (e.g. propene) to acrylic acid via the direct cooling thereof, in order to recycle the acrylic acid present therein back to the condensation process.

Appropriately in application terms, the number of dual-flow trays in the separation column (condensation column) will normally correspond to 5 to 15 and preferably 5 to 10 theoretical plates. The number of inventive crossflow hood trays which follow the dual-flow trays in the upward direction in the separation column for the contemplated fractional condensation will typically be such that it corresponds to about 10 to 30 theoretical plates. In addition, the dual-flow trays in the separation column appropriately extend up to the cross section of the separation column from which the acrylic acid contents of the reflux liquid, viewed toward the top of the column, are ≤60% by weight, or ≤40% by weight, based on the weight of the reflux liquid.

DE 10243625 A1 recommends equipping the uppermost dual-flow tray as a distributor tray in order to ensure very homogeneous operation within the at least one sequence of dual-flow trays over the cross section thereof. WO 2008/090190 A1, in contrast, recommends transferring the task of the distribution, which is very substantially homogeneous over the cross section of the separation column, of the liquid descending out of the sequence of crossflow hood trays to the lowermost crossflow mass transfer tray, and correspondingly configuring it in a modified manner.

Figure 17:
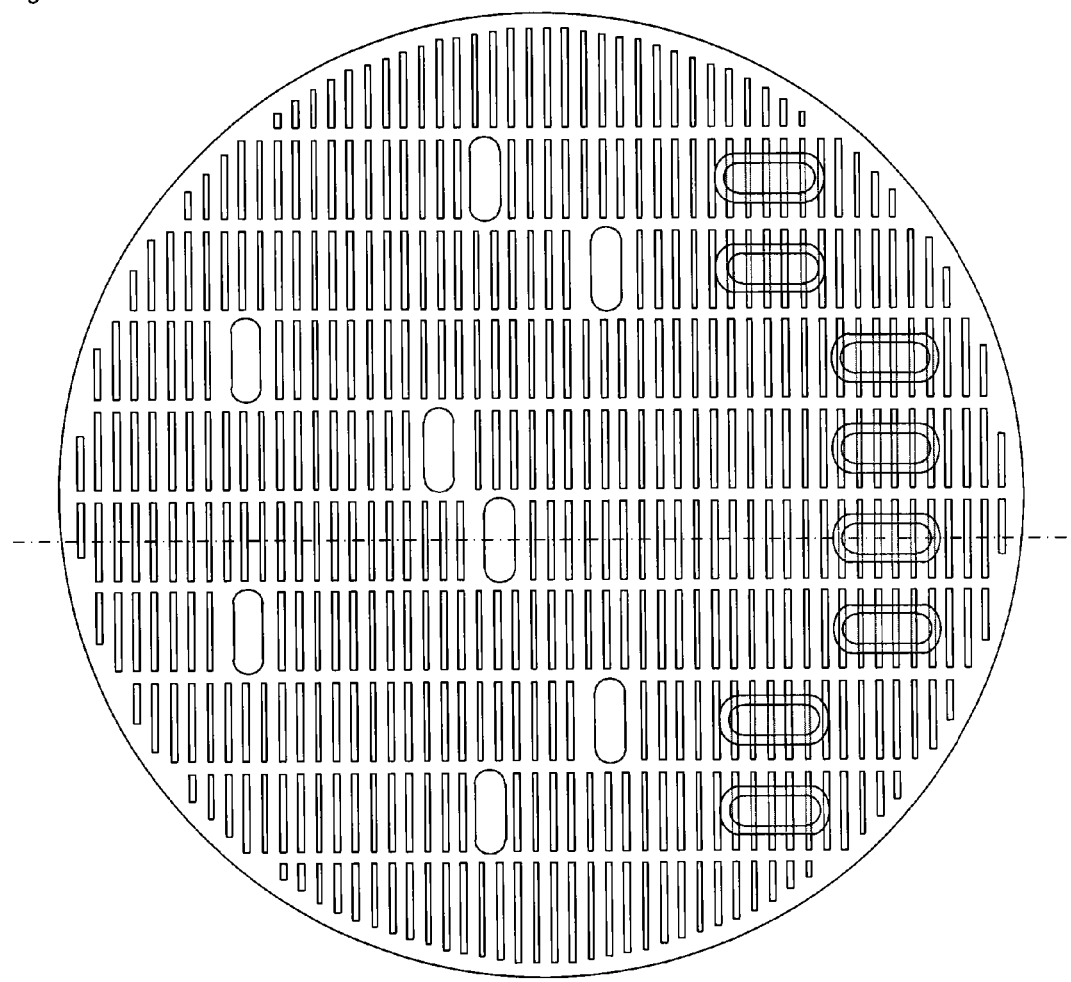
FIG. 17 is a top view of the lowermost tray arranged in an inventive sequence of mass transfer trays of crossflow mass transfer trays.

Following the latter recommendation, especially in the context of the object to be achieved which underlies this application, for the above-detailed fractional condensation of the product gas mixture of a heterogeneously catalyzed partial gas phase oxidation of a $C_3$ precursor compound (e.g. propene) to acrylic acid, in the case of additional use of a sequence of inventive crossflow hood trays according to FIGS. 5 and 6 of this document in the relevant separation column, for example, a hydraulically sealed mass transfer tray (hood tray) as shown in top view in FIG. 17 of this document as the lowermost tray of a sequence of mass transfer trays otherwise consisting of crossflow mass transfer trays according to FIGS. 5 and 6 is suitable as a "distributor tray" for the transition from the at least one sequence of dual-flow trays to the inventive sequence of crossflow hood trays arranged above it.

The elements shown in FIG. 17, the dimensions thereof, the dimensions of the tray itself, and the hoods, downcomers, necks and collecting cups and the dimensions thereof, correspond to those of the crossflow mass transfer tray (crossflow hood tray) shown in FIG. 5. In addition, the tray separations of the hoods present in the different lines of FIG. 17 are configured and structured like those of the hoods present in the different lines of FIG. 5. The essential difference in the two mass transfer trays (hood trays) according to FIGS. 5 and 17 is firstly, more particularly, that the downcomers (and corresponding downflow orifices) of the transition tray shown in FIG. 17 are not entirely accommodated in one half of the mass transfer tray, but rather are deliberately scattered more broadly over the tray for the purpose of a more uniform distribution of the liquid which flows downward from this mass transfer tray over the column cross section. Furthermore, for similar reasons, the longest dimension of the downflow orifice belonging to a downcomer in the mass transfer tray shown in plan view in FIG. 17 is aligned parallel in each case to the long edges of the hood passage orifices thereof.

Otherwise, the passage orifices of the mass transfer tray shown in FIG. 17 are, as in the case of the mass transfer tray shown in FIG. 5, equipped (hooded) with the vapor deflecting hoods which have forcing slots and are described in connection with FIG. 5 such that (proceeding from the line furthest removed from all downcomers) the guide surfaces of the hood slots in four successive flow channels positioned between two adjacent lines are aligned such that the liquid flowing in these channels in inventive operation (in the course of execution of the thermal separation process according to the invention, for example of the relevant fractional condensation of the product gas mixture comprising acrylic acid) flows in the same direction (and in the opposite direction in the four subsequent flow channels, etc.), such that the liquid is conveyed from the feed thereof onto the tray to the downcomers through the entirety of the flow channels in a meandering manner to the opposite side of the tray to the feed side.

Figure 18:
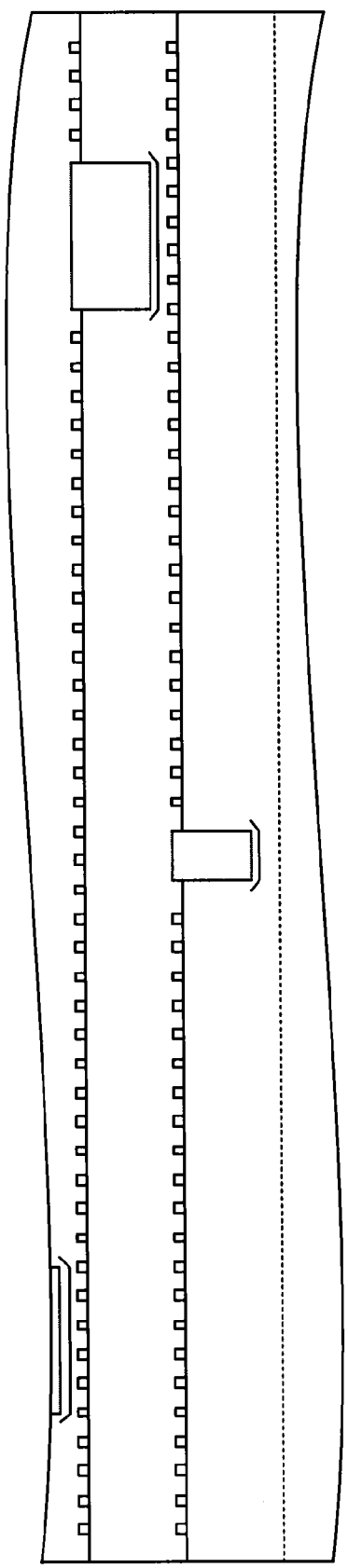
FIG. 18 is a longitudinal section running through the dotted line shown in FIG. 17.

FIG. 18 of this document shows, in schematic form, a longitudinal section of that sequence of mass transfer trays of which FIG. 17 shows the top view of the tray, which forms the transition from the at least one sequence of dual-flow trays to the sequence of inventive crossflow hood trays. The section (the longitudinal section) comprises three mass transfer trays arranged one above another. The middle of the three trays is the tray shown in top view in FIG. 17. Above this is an inventive crossflow mass transfer tray as shown in top view in FIG. 5. Below this, FIG. 18 shows the uppermost dual-flow tray. The longitudinal section shown in FIG. 18 runs through the dotted line shown in FIG. 17.

Both in the illustrative embodiment of DE 10243625 A1 and of WO 2008/090190 A1, the distance between the uppermost dual-flow tray and the lowermost tray of the sequence of crossflow hood trays which follows the at least one sequence of dual-flow trays in the upward direction is 1.50 m. This is due to the fact that the condensation columns in question are equipped with a manhole in this intermediate region. This is an orifice in the outer wall of the separation column which, outside of operation, enables access for persons of normal build into the condensation column (separation column) (for example in order to remove polymer of acrylic acid formed undesirably in the column in the course of the condensation process). Customary cross sections for a manhole are round, oval or less commonly also rectangular cross sections with a clear width of 400 to 800 mm. Only when there are plans to carry large tools or other large parts through the manhole is it larger. During the operation of the condensation column, the manhole, appropriately in application terms, is sealed pressure- and liquid-tight by means of screws with a manhole cover or a manhole door. Additional use of pivot devices facilitates the opening and movement of manhole covers. In general, the manhole ends in a short stub.

Typically, a separation column (for example a condensation column) does not have any separating internals in the manhole region. With a view to minimum unwanted polymer formation, however, for example in the relevant condensation process, this has not been found to be a fully satisfactory approach to a solution.

In order to remedy this defect, the present application proposes, for example, also mounting separating internals in the manhole region of the relevant condensation column, and in this way reducing the distance to the transition tray.

Figure 19:
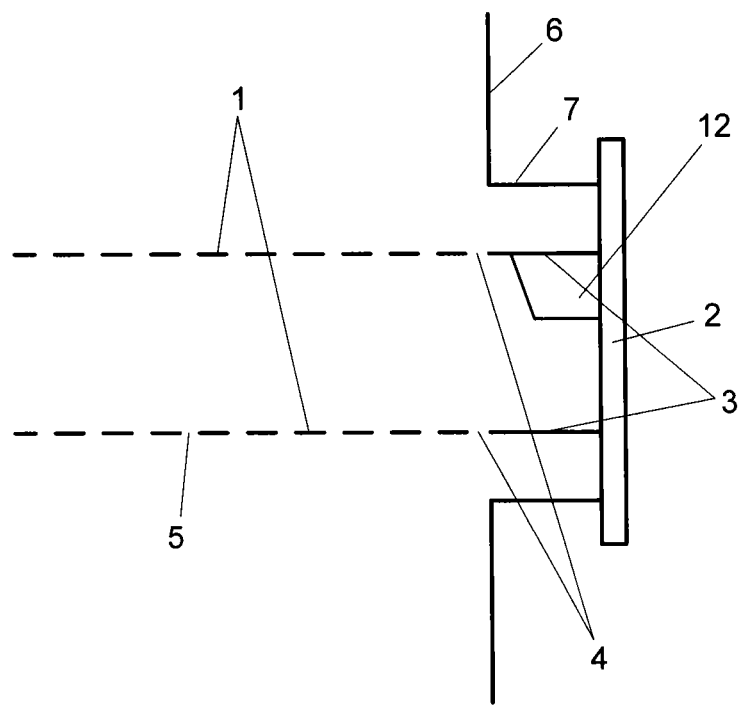
FIG. 19 is a schematic longitudinal section of the condensation column.

A possible embodiment in this regard for the relevant condensation column is shown, in schematic form, by FIG. 19 of this document in a schematic longitudinal section.

The numeric addresses have the following meanings:
1=dual-flow trays, the cross section of which does not correspond to a complete circle but only to a circle segment thereof, the center angle α of which is normally more than 300° but less than 355° (the area A of the circle segment is calculated as $A = 0.5 \cdot r^2 (\alpha - \sin \alpha)$, where r is the radius of the corresponding full circle and α is used in the arc measurement); the passage orifices and the arrangement thereof over the tray appropriately correspond to those of the uppermost dual-flow tray of the at least one sequence of circular dual-flow trays;
2=manhole cover;
3=plates (fins) which are welded onto the manhole cover and project into the column, which are perforated in a manner corresponding to the accompanying dual-flow trays (the holes in the fin are not shown); if required, they are supported by a support 12;
4=gap between dual-flow tray and fin welded onto the manhole cover at the same height, the width of which may normally be ≥0 mm and ≤2 mm;
5=passage orifice (hole) of the dual-flow tray;
6=outer wall of the separation column (condensation column);
7=stub.

Figure 20:
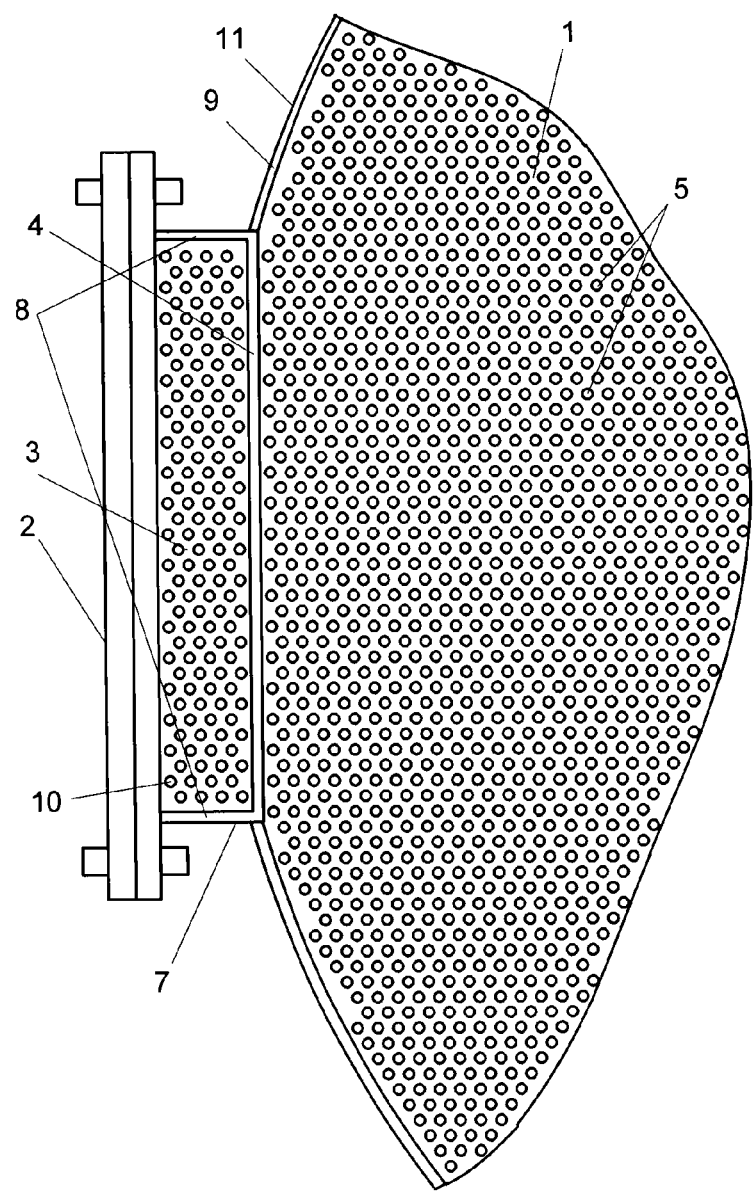
FIG. 20 is a top view of the condensation column.

FIG. 20 of this document shows, in schematic form, a corresponding top view; the same numeric addresses as in FIG. 19 have the same meaning. In addition, the numeric addresses in FIG. 20 are continued as follows:
8=gap between fin and stub;
9=support ring;
10=passage orifice in fin; and
11=outer wall of the separation column.

In an alternative embodiment, the dual-flow trays mounted in the region of the manhole may be assembled from individual plate segments, in which case the segments, appropriately in application terms, are configured such that the relevant portion thereof projects into the manhole stub and only ends just in front of (≤2 mm) the manhole cover.

Figure 21:
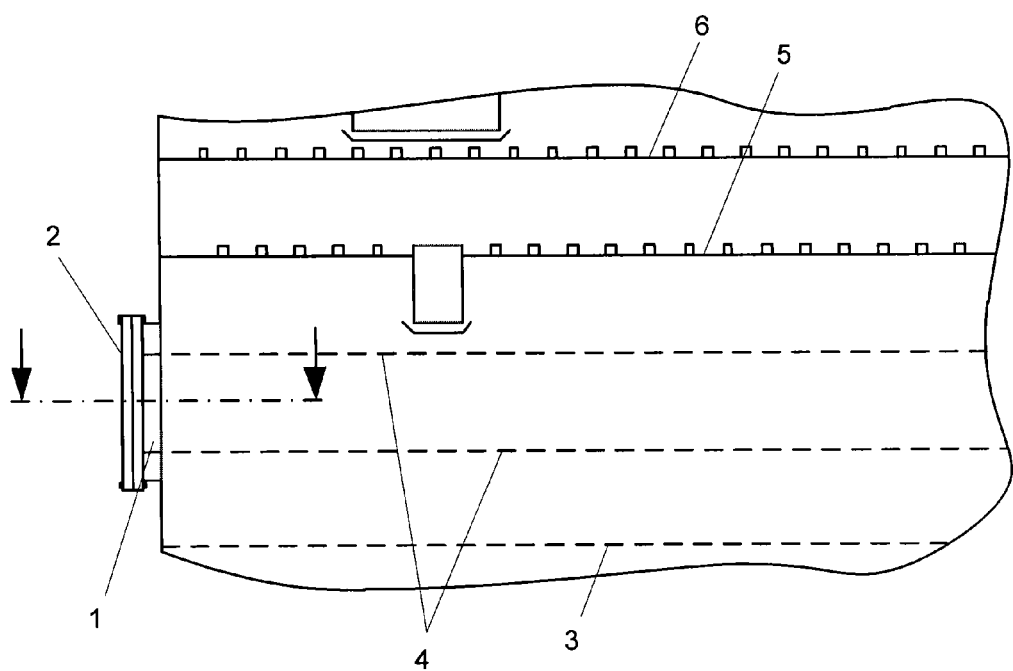
FIG. 21 is a longitudinal section of the condensation column in the manhole region.

FIG. 21 of this document shows, in a longitudinal section, the significant section from a condensation column configured according to the teaching of this document in the manhole region.

The numeric addresses have the following meanings:
1=manhole;
2=manhole cover;
3=uppermost dual-flow tray of the at least one sequence of dual-flow trays;
4=dual-flow trays projecting up to the manhole cover;
5=crossflow hood tray altered to become the transition tray according to FIG. 17; and
6=lowermost tray of the sequence of crossflow hood trays according to FIG. 5.

Figure 22:
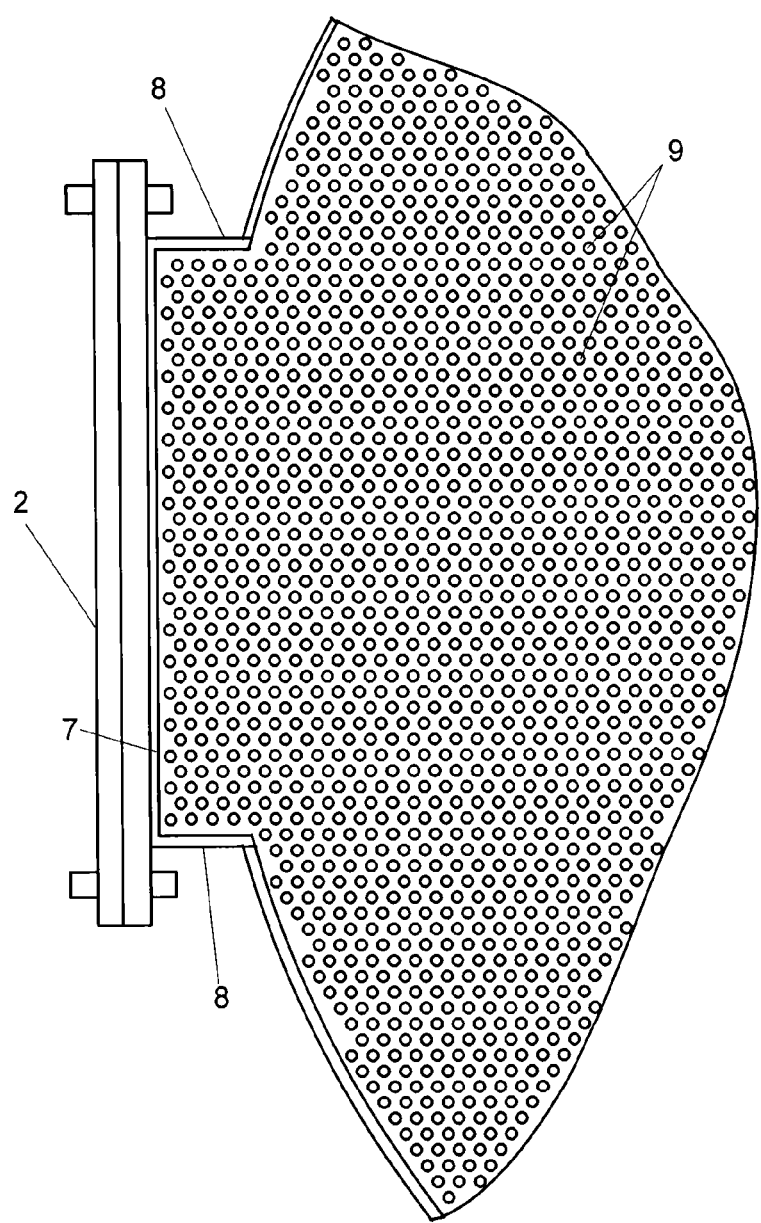
FIG. 22 is a top view of the condensation column along the line between the two arrows in FIG. 21.

FIG. 22 shows, in the top view along the line between the two arrows in FIG. 21, the lower of the two dual-flow trays which are assembled from plate segments and project into the manhole in schematic form. The columns (supports) bearing the plate segments stand on the tray directly below.

The same numeric addresses as in FIG. 21 have the same meaning. In addition, the numeric addresses are continued in FIG. 22 as follows:
7=gap with a width of ≤2 mm;
8=column wall; and
9=passage orifice.

The clear distances from the dual-flow tray 3 to the lower dual-flow tray 4, from the upper dual-flow tray 4 to the transition tray 5, from the transition tray 5 to the lowermost inventive crossflow hood tray, and between the two dual-flow trays 4, are appropriately similar (within the range from 400 mm to 600 mm). The dual-flow trays 4 additionally mounted in the manhole region not only reduce the tendency to unwanted polymerization in the operation of the condensation process, but also improve the separating action of the column.

A further advantageous development of the fractional condensation detailed in documents DE 10243625 A1 and WO 2008/090190 A1 relates to the further use of mother liquor, which remains in the case of crystallizative further purification of crude acrylic acid withdrawn from the second chimney tray (collecting tray) in the condensation column. Both DE 10243625 A1 and WO 2008/090190 A1 recommend recycling the entire flow rate of such remaining mother liquor still comprising significant amounts of acrylic acid into the condensation column at the uppermost dual-flow tray below the second chimney tray.

A disadvantage of such a procedure is the comparatively low temperature of the mother liquor that it generally still has in spite of heat integration elements employed (normally, this temperature is not above 95° C.). Overall, a comparatively marked cooling effect arises in this manner below the second chimney tray, and as a result a comparatively intense condensative action, which necessarily reduces the flow rate of the liquid descending above the second chimney tray in the condensation column and has a limiting effect on the desired separating action in this column section.

In an advantageous development of the procedure recommended in WO 2008/090190 A1, such a mother liquor stream is therefore divided into at least two substreams. The first substream of mother liquor, which normally accounts for at least 80% by weight of the overall mother liquor stream, is recycled into the condensation column in a manner known per se, following the recommendations of WO 2008/090190 A1 and of DE 102436 25 A1. The at least second substream of mother liquor, which generally accounts for not more than 20% by weight of the overall mother liquor stream, is, in contrast, advantageously in application terms, used as part of the reflux liquid for the (countercurrent) rectification to which the acrylic acid-laden stripping gas is advantageously subjected in application terms, with which acrylic acid present dissolved in the bottoms liquid withdrawn from the bottom of the condensation column has been stripped out therefrom beforehand, preferably under conditions which promote the redissociation of Michael adducts of acrylic acid itself likewise present dissolved in the bottoms liquid, before it is recycled into the bottom space of the condensation column, for example together with the product gas mixture of the partial oxidation of the $C_3$ precursor compound (e.g. propene) to give acrylic acid via the direct cooling thereof. The (countercurrent) rectification counteracts recycling of secondary components unwanted in the condensation column, for example low molecular weight aldehydes, into said condensation column (in this regard, see also documents WO 2004/035514 A1 and DE 10332758 A1).

It will be appreciated that the different separation steps to be employed in the course of removal of acrylic acid from the respective product gas mixture of the partial oxidation which produces it are each executed with inhibition of polymerization. Following the recommendations of DE 102007004960 A1 and of WO 2008/090190 A1, the polymerization inhibitors used for this purpose are especially phenothiazine (PTZ) and the monomethyl ether of hydroquinone (MEHQ) and molecular oxygen.

The pure product obtainable in the procedure described is a glacial acrylic acid melt which has been freed of phenothiazine and, in line with the particular subsequent use, is storage-stablizable with $MEHQ/O_2$ within wide content ranges. Typically (for example for a subsequent use for production of water-superabsorbent polymer), the MEHQ content of such stored glacial acrylic acid may be 50 ppm by weight (based on the amount of acrylic acid present).

Finally, it should be emphasized that the thermal separation process according to the invention can advantageously be employed in a completely corresponding manner when, instead of at least one (meth)acrylic monomer, other mono- and/or polyunsaturated compounds, for example acrylonitrile, styrene and/or butadiene, are involved.

Thus, the present application encompasses, more particularly, the following inventive embodiments:

1. A thermal separation process, conducted in a separation column comprising separating internals, between at least one gas ascending within the separation column and at least one liquid descending within the separation column, at least one of which comprises (meth)acrylic monomers, at least some of the separating internals being at least one sequence of at least two identical crossflow mass transfer trays having at least one downcomer through which liquid descends from the particular crossflow mass transfer tray, and the crossflow mass transfer trays being arranged one on top of another within the at least one sequence in the separation column such that two crossflow mass transfer trays in the separation column, one of which follows the other in the downward direction, are each mounted offset (turned) from one another by 180° about the longitudinal axis of the column, as a result of which their downcomers are on mutually opposite sides of the separation column, the at least one downcomer of the upper of two successive crossflow mass transfer trays constitutes at least one upcomer for the crossflow mass transfer tray below it, through which liquid descends from the upper crossflow mass transfer tray as at least one feed to the crossflow mass transfer tray below it, the liquid descending through the at least one upcomer from the upper to the lower crossflow mass transfer tray, viewed over the (entire) lower crossflow mass transfer tray, flows from the at least one feed to the lower crossflow mass transfer tray across the tray to the at least one downcomer of the lower crossflow mass transfer tray, and there are passage orifices between the at least one feed to the lower crossflow mass transfer tray and the at least one downcomer of the lower crossflow mass transfer tray, through which the at least one gas ascends through the lower crossflow mass transfer tray, wherein
    at least within one of the at least one sequence of identical crossflow mass transfer trays, the lower of two successive crossflow mass transfer trays in each case, in the direction of the crossflow from the at least one feed thereof to the at least one downcomer thereof, additionally has at least one passage orifice for the at least one ascending gas beyond at least one downcomer (and the uppermost crossflow mass transfer tray in this sequence is identical to the crossflow mass transfer tray below it).

2. The thermal separation process according to embodiment 1, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is a sequence of crossflow sieve trays, or of crossflow bubble-cap trays, or of crossflow valve trays.

3. The thermal separation process according to embodiment 1 or 2, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer comprises at least three identical crossflow mass transfer trays.
4. The thermal separation process according to embodiment 1 or 2, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer comprises at least four identical crossflow mass transfer trays.
5. The thermal separation process according to embodiment 1 or 2, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer comprises at least five identical crossflow mass transfer trays.
6. The thermal separation process according to embodiment 1 or 2, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer comprises at least ten identical crossflow mass transfer trays.
7. The thermal separation process according to any of embodiments 1 to 6, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer comprises not more than fifty identical crossflow mass transfer trays.
8. The thermal separation process according to any of embodiments 1 to 6, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer comprises not more than forty identical crossflow mass transfer trays.
9. The thermal separation process according to any of embodiments 1 to 6, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer comprises not more than thirty identical crossflow mass transfer trays.
10. The thermal separation process according to any of embodiments 1 to 9, wherein the crossflow mass transfer trays of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer are arranged equidistantly one above another.
11. The thermal separation process according to any of embodiments 1 to 10, wherein, within the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, the liquid flows on the lower crossflow mass transfer tray in each case from the at least one feed in a meandering manner to the at least one downcomer.
12. The thermal separation process according to any of embodiments 1 to 11, wherein the lower of two successive crossflow mass transfer trays in each case in the at least one sequence of identical crossflow mass transfer trays has, in the direction of crossflow from the at least one feed thereof to the at least one downcomer thereof, additionally at least one passage orifice for the at least one ascending gas beyond at least one downcomer.
13. The thermal separation process according to any of embodiments 1 to 12, wherein the separation column comprises at least one further separating internal from the group consisting of structured packings, unstructured packings, sequences of dual-flow trays, and random packings.
14. The thermal separation process according to any of embodiments 1 to 13, wherein the passage orifices of the crossflow mass transfer trays of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer are circular, or polygonal, or have the shape of a elongated hole.
15. The thermal separation process according to embodiment 14, wherein the passage orifices are triangular, or rectangular, or square.
16. The thermal separation process according to any of embodiments 1 to 15, wherein a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer has at least two downcomers.
17. The thermal separation process according to any of embodiments 1 to 15, wherein a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer has at least three downcomers.
18. The thermal separation process according to any of embodiments 1 to 15, wherein a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer has at least four downcomers.
19. The thermal separation process according to any of embodiments 1 to 15, wherein a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer has at least five downcomers.
20. The thermal separation process according to any of embodiments 1 to 15, wherein a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer has at least seven downcomers.
21. The thermal separation process according to any of embodiments 1 to 15, wherein a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer has at least nine downcomers.
22. The thermal separation process according to any of embodiments 1 to 21, wherein a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally has at least one passage orifice for the at least one ascending gas beyond at least one downcomer has not more than twenty downcomers.
23. The thermal separation process according to any of embodiments 1 to 21, wherein a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally has at least one passage orifice for the at least one ascending gas beyond at least one downcomer has not more than fifteen downcomers.
24. The thermal separation process according to any of embodiments 1 to 23, wherein the downflow orifices of the downcomers of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.
25. The thermal separation process according to any of embodiments 1 to 24, wherein the cross section of the downflow orifice of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is circular, or rectangular, or square, or that of an elongated hole.
26. The thermal separation process according to any of embodiments 1 to 25, wherein the cross-sectional area $F_A$ of the downflow orifice of the at least one downcomer of a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer is at least twice as large as the cross-sectional area $F_B$ of the largest passage orifice of the crossflow mass transfer tray.
27. The thermal separation process according to embodiment 26, wherein $F_A$ is more than $10^6 \times F_B$.
28. The thermal separation process according to embodiment 26, wherein $F_A$ is more than $1000 \times F_B$.
29. The thermal separation process according to embodiment 26, wherein $F_A$ is not more than $20 \times F_B$.
30. The thermal separation process according to any of embodiments 1 to 29, wherein the total area of the cross-sectional areas of the downflow orifices of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is not more than 20% of the cross-sectional area of the crossflow mass transfer tray.
31. The thermal separation process according to any of embodiments 1 to 29, wherein the total area of the cross-sectional areas of the downflow orifices of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is not more than 10% of the cross-sectional area of the crossflow mass transfer tray.
32. The thermal separation process according to any of embodiments 1 to 29, wherein the total area of the cross-sectional areas of the downflow orifices of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is not more than 5% of the cross-sectional area of the crossflow mass transfer tray.
33. The thermal separation process according to any of embodiments 1 to 32, wherein the total area of the cross-sectional areas of the downflow orifices of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is at least 0.2% of the cross-sectional area of the crossflow mass transfer tray.

34. The thermal separation process according to any of embodiments 1 to 32, wherein the total area of the cross-sectional areas of the downflow orifices of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is at least 0.5% of the cross-sectional area of the crossflow mass transfer tray.

35. The thermal separation process according to any of embodiments 1 to 34, wherein a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, in the direction of crossflow from the at least one feed thereof to the at least one downcomer thereof, additionally has at least one passage orifice for the at least one ascending gas beyond more than one downcomer.

36. The thermal separation process according to any of embodiments 1 to 34, wherein a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, in the direction of crossflow from the at least one feed thereof to the at least one downcomer thereof, additionally has at least one passage orifice for the at least one ascending gas beyond at least one third of all downcomers.

37. The thermal separation process according to any of embodiments 1 to 34, wherein a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, in the direction of crossflow from the at least one feed thereof to the at least one downcomer thereof, additionally has at least one passage orifice for the at least one ascending gas beyond at least half of all downcomers.

38. The thermal separation process according to any of embodiments 1 to 34, wherein a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, in the direction of crossflow from the at least one feed thereof to the at least one downcomer thereof, additionally has at least one passage orifice for the at least one ascending gas beyond every downcomer.

39. The thermal separation process according to any of embodiments 1 to 34, wherein the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is surrounded on all sides by passage orifices.

40. The thermal separation process according to any of embodiments 1 to 39, wherein a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer has a circular cross section.

41. The thermal separation process according to embodiment 40, wherein the at least one downcomer of a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer is within a circle segment of the crossflow mass transfer tray whose area is not more than five sixths of half of the circle area of the crossflow mass transfer tray.

42. The thermal separation process according to embodiment 40, wherein the at least one downcomer of a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer is within a circle segment of the crossflow mass transfer tray whose area is not more than four fifths of half of the circle area of the crossflow mass transfer tray.

43. The thermal separation process according to embodiment 40, wherein the at least one downcomer of a crossflow mass transfer tray of the at least one sequence of identical crossflow mass transfer trays within which the lower of two successive crossflow mass transfer trays in each case has, in the direction of crossflow from the at least one feed thereof to the at least one downcomer thereof, additionally at least one passage orifice for the at least one ascending gas beyond at least one downcomer is within a circle segment of the crossflow mass transfer tray whose area is not more than three quarters of half of the circle area of the crossflow mass transfer tray.

44. The thermal separation process according to embodiment 40, wherein the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is within a circle segment of the crossflow mass transfer tray, the area of which is not more than two thirds of half the circle area of the crossflow mass transfer tray.

45. The thermal separation process according to any of embodiments 40 to 44, wherein the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is within a circle segment of the crossflow mass transfer tray, the area of which is at least one fifth of half the circle area of the crossflow mass transfer tray.

46. The thermal separation process according to any of embodiments 40 to 44, wherein the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is within a circle segment of the crossflow mass transfer tray, the area of which is at least one quarter of half the circle area of the crossflow mass transfer tray.

47. The thermal separation process according to any of embodiments 41 to 46, wherein the downflow orifices of the at least one downcomer are arranged within the circle segment such that there is no further downflow orifice on that straight line which joins the center of a downflow orifice to the center of the feed area of the feed opposite.

48. The thermal separation process according to any of embodiments 41 to 47, wherein the downflow orifices of the at least one downcomer are arranged within the circle segment such that the shortest direct connecting line from the center of a downflow orifice to a point on the circumference line of the crossflow mass transfer tray is not longer than two thirds of the radius of the crossflow mass transfer tray.

49. The thermal separation process according to any of embodiments 41 to 47, wherein the downflow orifices of the at least one downcomer are arranged within the circle segment such that the shortest direct connecting line from the center of a downflow orifice to a point on the circumference line of the crossflow mass transfer tray is not longer than three fifths of the radius of the crossflow mass transfer tray.

50. The thermal separation process according to any of embodiments 41 to 47, wherein the downflow orifices of the at least one downcomer are arranged within the circle segment such that the shortest direct connecting line from the center of a downflow orifice to a point on the circumference line of the crossflow mass transfer tray is not longer than half of the radius of the crossflow mass transfer tray.

51. The thermal separation process according to any of embodiments 41 to 47, wherein the downflow orifices of the at least one downcomer are arranged within the circle segment such that the shortest direct connecting line from the center of a downflow orifice to a point on the circumference line of the crossflow mass transfer tray is not longer than two fifths of the radius of the crossflow mass transfer tray.

52. The thermal separation process according to any of embodiments 40 to 51, wherein the distance between the center of the downflow orifice of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer and the geometric center of the circular crossflow mass transfer tray is at least as long as one third of the radius of the crossflow mass transfer tray.

53. The thermal separation process according to any of embodiments 40 to 51, wherein the distance between the center of the downflow orifice of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer and the geometric center of the circular crossflow mass transfer tray is at least as long as two fifths of the radius of the crossflow mass transfer tray.

54. The thermal separation process according to any of embodiments 40 to 51, wherein the distance between the center of the downflow orifice of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer and the geometric center of the circular crossflow mass transfer tray is at least as long as half of the radius of the crossflow mass transfer tray.

55. The thermal separation process according to any of embodiments 40 to 51, wherein the distance between the center of the downflow orifice of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer and the geometric center of the circular crossflow mass transfer tray is at least as long as three fifths of the radius of the crossflow mass transfer tray.

56. The thermal separation process according to any of embodiments 1 to 55, wherein the at least one downcomer of the upper of two successive crossflow mass transfer trays in each case within the at least one sequence of identical crossflow mass transfer trays in which the lower of two successive crossflow mass transfer trays in each case, in the direction of crossflow from the at least one feed thereof to the at least one downcomer thereof, additionally has at least one passage orifice for the at least one ascending gas beyond at least one downcomer is extended downward as an upcomer for the lower crossflow mass transfer tray in each case to such an extent that it is immersed into the liquid flowing on the lower crossflow mass transfer tray.

57. The thermal separation process according to embodiment 56, wherein the liquid descending in the upcomer extended downward onto the lower crossflow mass transfer tray descends onto a feed area of the lower crossflow mass transfer tray which does not have any passage orifices.

58. The thermal separation process according to embodiment 57, wherein the lower crossflow mass transfer tray has at least one passage orifice both in front of the feed area in the direction of crossflow and beyond the feed area in the opposite direction to the crossflow.

59. The thermal separation process according to embodiment 58, wherein the feed area of the lower crossflow mass transfer tray is surrounded on all sides by passage orifices.

60. The thermal separation process according to any of embodiments 1 to 55, wherein the at least one downcomer of the upper of two successive crossflow mass transfer trays in each case within the at least one sequence of identical crossflow mass transfer trays in which the lower of two successive crossflow mass transfer trays in each case, in the direction of crossflow from the at least one feed thereof to the at least one downcomer thereof, additionally has at least one passage orifice for the at least one ascending gas beyond at least one downcomer is extended downward as an upcomer for the lower crossflow mass transfer tray in each case only to such an extent that it is not immersed into the liquid flowing on the lower crossflow mass transfer tray.

61. The thermal separation process according to embodiment 60, wherein the at least one downcomer has a static or dynamic liquid seal.

62. The thermal separation process according to embodiment 61, wherein the static liquid seal is accomplished with the aid of a collecting cup which is mounted below the outflow end of the downcomer and into which the outflow end projects.

63. The thermal separation process according to any of embodiments 60 to 62, wherein the liquid descending in the upcomer to the lower crossflow mass transfer tray descends onto a feed area of the lower crossflow mass transfer tray, said feed area having passage orifices.

64. The thermal separation process according to any of embodiments 1 to 63, wherein at least 20% of the passage orifices of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.

65. The thermal separation process according to any of embodiments 1 to 63, wherein at least 40% of the passage orifices of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.

66. The thermal separation process according to any of embodiments 1 to 63, wherein at least 50% of the passage orifices of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.

67. The thermal separation process according to any of embodiments 1 to 63, wherein at least 60% of the passage orifices of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.

68. The thermal separation process according to any of embodiments 1 to 63, wherein at least 70% of the passage orifices of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.

69. The thermal separation process according to any of embodiments 1 to 63, wherein at least 80% of the passage orifices of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.

70. The thermal separation process according to any of embodiments 1 to 69, wherein the passage orifices are bubble-cap passage orifices having forcing slots.

71. The thermal separation process according to embodiment 70, wherein the passage orifices have a rectangular cross section.

72. The thermal separation process according to any of embodiments 1 to 71, wherein the at least one (meth) acrylic monomer is one from the group consisting of acrolein, acrylic acid, esters of acrylic acid, methacrolein, methacrylic acid and esters of methacrylic acid.

73. The thermal separation process according to any of embodiments 1 to 72, wherein the at least one (meth) acrylic monomer is one selected from the group consisting of hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

74. The thermal separation process according to any of embodiments 1 to 73, which is a thermal separation process from the group consisting of fractional condensation, rectification, absorption, desorption and stripping.

75. The thermal separation process according to any of embodiments 1 to 73, which is a process for fractional condensation for removal of acrylic acid from a product gas mixture comprising acrylic acid from a heterogeneously catalyzed gas phase partial oxidation of a $C_3$ precursor compound of acrylic acid with molecular oxygen to give acrylic acid.

76. The thermal separation process according to embodiment 75, wherein the $C_3$ precursor compound is propene and/or propane.

77. The thermal separation process according to embodiment 75 or 76, wherein
the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is a sequence of crossflow mass transfer trays whose passage orifices are bubble-cap passage orifices having forcing slots, in the separation column, below this at least one sequence of identical crossflow mass transfer trays, at least one sequence of dual-flow trays is mounted, the product gas mixture comprising acrylic acid is supplied to the separation column below the lowermost dual-flow tray, and condensed acrylic acid is withdrawn from the at least one sequence of dual-flow trays.

78. The thermal separation process according to any of embodiments 75 to 77, wherein the product gas mixture, based on the total amount of constituents present (therein), has the following contents:
1 to 30% by weight of acrylic acid,
0.05 to 10% by weight of molecular oxygen,
1 to 30% by weight of water,
0 to 5% by weight of acetic acid,
0 to 3% by weight of propionic acid,
0 to 1% by weight of maleic acid and/or maleic anhydride,
0 to 2% by weight of acrolein,
0 to 1% by weight of formaldehyde,
0 to 1% by weight of furfural,
0 to 0.5% by weight of benzaldehyde,
0 to 1% by weight of propene, and
as the remainder, inert gases, for example nitrogen, carbon monoxide, carbon dioxide, methane and/or propane.

79. The thermal separation process according to any of embodiments 1 to 78, wherein a gaseous and/or liquid mixture comprising ≥2% by weight of at least one (meth)acrylic monomer is supplied to the separation column.

80. The thermal separation process according to any of embodiments 1 to 78, wherein a gaseous and/or liquid mixture comprising ≥10% by weight of at least one (meth)acrylic monomer is supplied to the separation column.

81. The thermal separation process according to any of embodiments 1 to 78, wherein a gaseous and/or liquid mixture comprising ≥20% by weight of at least one (meth)acrylic monomer is supplied to the separation column.

82. The thermal separation process according to any of embodiments 1 to 74, wherein a gaseous and/or liquid mixture comprising ≥60% by weight of at least one (meth)acrylic monomer is supplied to the separation column.

83. The thermal separation process according to any of embodiments 1 to 74, wherein a gaseous and/or liquid mixture comprising ≥80% by weight of at least one (meth)acrylic monomer is supplied to the separation column.

84. The thermal separation process according to any of embodiments 1 to 74, wherein a gaseous and/or liquid mixture comprising ≥95% by weight of at least one (meth)acrylic monomer is supplied to the separation column.

85. A circular mass transfer tray which has passage orifices and has at least one downcomer with a downflow orifice only in one half and does not have any feed area free of passage orifices in the half opposite this half, and wherein it has passage orifices for gas ascending in working operation, proceeding from the center of the downflow orifice of the at least one downcomer, not only in the tray area in front of the at least one downcomer in the direction of the opposite half, but also in the tray area beyond the at least one downcomer in the opposite direction.

86. A sequence, present in a separation column, of at least two identical crossflow mass transfer trays having at least one downcomer through which liquid can descend from the particular crossflow mass transfer tray, the crossflow mass transfer trays being arranged one on top of another within the sequence in the separation column such that two crossflow mass transfer trays in the separation column, one of which follows the other in the downward direction, are each mounted offset (turned) from one another by 180° about the longitudinal axis of the column, as a result of which their downcomers are on mutually opposite sides of the separation column, the at least one downcomer of the upper of two successive crossflow mass transfer trays constitutes at least one upcomer for the crossflow mass transfer tray below it, through which liquid can descend from the upper crossflow mass transfer tray as at least one feed to the crossflow mass transfer tray below it, a liquid descending through the at least one upcomer from the upper to the lower crossflow mass transfer tray, viewed over the (entire) lower crossflow mass transfer tray, will flow from the at least one feed to the lower crossflow mass transfer tray across the tray to the at least one downcomer of the lower crossflow mass transfer tray, and there are passage orifices between the at least one feed to the lower crossflow mass transfer tray and the at least one downcomer of the lower crossflow mass transfer tray, through which gas can ascend through the lower crossflow mass transfer tray, wherein within the sequence of identical crossflow mass transfer trays, the lower of two successive crossflow mass transfer trays in each case, in the direction of the crossflow from the at least one feed thereof to the at least one downcomer thereof, additionally has at least one passage orifice beyond at least one downcomer through which gas can ascend.

87. A sequence of at least two identical crossflow mass transfer trays present in a separation column according to embodiment 86, wherein the crossflow mass transfer trays have a circular cross section.

Example and comparative example (the details given below are based not just on analytical determinations but also on arithmetic elements from component balances, mass balances and energy (heat) balances)

EXAMPLE

A Steady State is Described

From a heterogeneously catalyzed gas phase partial oxidation of propylene of "polymer grade" purity executed in two stages (cf. WO 2004/009525 A1) in two series-connected two-zone reactors (as described and illustrated in documents WO 2004/0835369 A1, WO 2004/085367 A1, WO 2007/082827 A1, DE 102010048405 A1, DE 10313209 A1, and DE 10313208 A1; the propene loading of the fixed catalyst bed of the first reaction stage is 195 l (STP)/1-11 and the acrolein loading of the fixed catalyst bed of the second reaction stage is 175 l (STP) 1·h; the loading is as defined in the above documents), a product gas mixture which has a temperature of 260° C. and a pressure of 1.55 bar and is of the following composition is obtained (apart from the reaction gas mixture supplied, the analytically detected constituents are always listed hereinafter based on the total amount thereof; methylene glycol is included as a mixture of formaldehyde and water):
11.92% by wt. of acrylic acid,
0.25% by wt. of acetic acid,
4.569% by wt. of water, 0.0257% by wt. of formic acid,
0.1832% by wt. of formaldehyde,
0.0837% by wt. of acrolein,
0.0039% by wt. of propionic acid,
0.0032% by wt. of furfurals,
0.0015% by wt. of allyl acrylate,
0.0011% by wt. of allyl formate,
0.0026% by wt. of benzaldehyde,
0.0962% by wt. of maleic anhydride,
0.0137% by wt. of benzoic acid,
0.0052% by wt. of phthalic anhydride,
2.21% by wt. of $CO_2$,
0.632% by wt. of CO,
0.161% by wt. of propane,
0.258% by wt. of propylene,
3.21% by wt. of $O_2$, and
76.37% by wt. of $N_2$.

The reaction gas mixture to be supplied to one tandem reactor line is a mixture of cycle gas and polymer-grade propylene (propene), into which primary air is subsequently metered. The mixing is in each case accomplished by a static mixer.

Between the first- and second-stage reactors, secondary air (20856 kg/h) is also supplied.

The ratios are adjusted to the operating state of the reactor line and are, upstream of the first-stage reactor:
cycle gas=102641 kg/h,
polymer-grade propylene=19091 kg/h,
air=97781 kg/h.

The significant contents of the resulting reaction gas mixture stream are:
12.1% by wt. of $O_2$,
1.25% by wt. of $CO_2$,
0.351% by wt. of CO,
0.176% by wt. of propane,
8.75% by wt. of propylene (propene),
0.897% by wt. of $H_2O$, and
76.4% by wt. of $N_2$.

The product gas mixture (240369 kg/h) is cooled to a temperature of 109.4° C. by direct cooling in a spray cooler (quench 1) operated in cocurrent.

The liquid to be used for direct cooling of the product gas mixture (quench liquid 1) is a portion of the bottoms liquid which is withdrawn from the bottom of the condensation column described hereinafter.

Contents of this bottoms liquid (temperature=107.0° C.) are:

| | |
|---|---|
| 63.5% by wt. of | acrylic acid, |
| 0.388% by wt. of | acetic acid, |
| 0.992% by wt. of | water, |
| 0.0140% by wt. of | formic acid, |
| 0.0026% by wt. of | formaldehyde, |
| 0.0072% by wt. of | acrolein, |
| 0.0592% by wt. of | propionic acid, |
| 0.176% by wt. of | furfurals, |
| 0.0018% by wt. of | allyl acrylate, |
| 0.0011% by wt. of | allyl formate, |
| 0.144% by wt. of | benzaldehyde, |
| 5.87% by wt. of | maleic anhydride, |
| 0.877% by wt. of | benzoic acid, |
| 0.333% by wt. of | phthalic anhydride, |
| 18.72% by wt. of | diacrylic acid, } Michael adducts, |
| 8.0% by wt. of | polyacrylic acid, |
| 0.224% by wt. of | phenothiazine, |
| 0.690% by wt. of | MEHQ, and |
| 0.0001% by wt. of | oxygen. |

The spray cooler of the quench circuit 1 for direct cooling of the product gas mixture is supplied at the aforementioned temperature only with an amount of 434 m³/h of withdrawn bottoms liquid. 3750 kg/h of withdrawn bottoms liquid are supplied as feed to the second stripping column.

The mixture of product gas mixture cooled to 109.4° C. and unvaporized quench liquid 1 which results from the direct cooling is conducted as such into the bottom of the condensation column. The pressure in the bottoms space and in the quench 1 is 1.52 bar.

The internal diameter of the condensation column is a constant 7.4 m.

The second stripping column, which is supplied with 3750 kg/h of the bottoms liquid withdrawn from the bottom of the condensation column as feed, comprises 45 dual-flow trays as separating internals. Just like the condensation column, the second stripping column is thermally insulated from the environment (but the latter is not indispensible; in other words, the process is also performable without such thermal insulation). The internal diameter of the second stripping column over all dual-flow trays is a uniform 2.2 m. The 45 dual-flow trays are arranged equidistantly (400 mm) one on top of another in the second stripping column. The orifice ratio thereof is graduated from the bottom upward as follows: trays 1 to 8=14.2%; trays 9 to 16=15.7%; trays 17 to 44=17% and tray 45=15.5%. The hole diameter of all dual-flow trays is a uniform 14 mm (hole arrangement corresponding to strict triangular pitch).

The 3750 kg/h of bottoms liquid withdrawn from the condensation column are supplied at a temperature of 107.0° C. to the eighth dual-flow tray (from the bottom).

The energy is supplied to the second stripping column by means of an outside forced-circulation three-flow shell-and-tube flash evaporator (cf. Grundoperationen chemischer Verfahrenstechnik [Basic Operations in Chemical Engineering], 4th edition, Steinkopff Verlag Dresden, 1974, p. 434). This is supplied with 650000 kg/h of bottoms liquid which has been withdrawn from the bottom of the second stripping column with a temperature of 170° C. and a pressure of 1.68 bar, and has the following contents:

| | |
|---|---|
| 44.67% by wt. of | acrylic acid, |
| 0.807% by wt. of | acetic acid, |
| 0.168% by wt. of | water, |
| 0.0142% by wt. of | formic acid, |
| 0.0001% by wt. of | formaldehyde, |
| 0.0012% by wt. of | acrolein, |
| 0.0545% by wt. of | propionic acid, |
| 0.43% by wt. of | furfurals, |
| 0.0029% by wt. of | allyl formate, |
| 0.519% by wt. of | diethyl phthalate, |
| 0.342% by wt. of | benzaldehyde, |
| 12.9% by wt. of | maleic anhydride, |
| 1.84% by wt. of | benzoic acid, |
| 0.696% by wt. of | phthalic anhydride, |
| 15.5% by wt. of | diacrylic acid, } Michael adducts |
| 20% by wt. of | polyacrylic acid, |
| 0.505% by wt. of | phenothiazine, |
| 1.55% by wt. of | MEHQ, and |
| 0.0001% by wt. of | oxygen. |

The heat carrier conducted through the space surrounding the heat exchanger tubes is steam (pressure=16 bar) (in a meandering manner, conducted by corresponding deflecting plates). In the course of flow through the heat exchanger tubes, the bottoms liquid is heated and recycled into the bottom of the second stripping column at a temperature of 173.1° C. 1793 kg/h of bottoms liquid additionally withdrawn from the bottom of the second stripping column are branched off, degassed, diluted with methanol (67.5 kg/h, has liquefying action) and sent to residue incineration.

In addition, the bottom of the second stripping column is supplied at a temperature of 90.8° C. and a pressure of approx. 1.90 bar with 21866 kg/h of a gas mixture which fed of first laden gas conducted out of the first stripping column at the top thereof and of residual gas conducted out at the top of the condensation column (it is branched off beyond the cycle gas compressor; based on the weight of the gas mixture, the residual gas content is typically≤15% by weight), and which has the following contents:
- 4.46% by wt. of acrylic acid,
- 1.32% by wt. of acetic acid,
- 3.90% by wt. of water,
- 0.847% by wt. of formic acid,
- 0.0848% by wt. of formaldehyde,
- 0.0996% by wt. of acrolein,
- 0.0053% by wt. of propionic acid,
- 0.0003% by wt. of furfurals,
- 0.0320% by wt. of allyl formate,
- 0.0426% by wt. of diethyl phthalate,
- 3.48% by wt. of $O_2$,
- 2.40% by wt. of $CO_2$,
- 0.6834% by wt. of CO,
- 0.175% by wt. of propane,
- 0.280% by wt. of propylene, and
- 82.19% by wt. of $N_2$.

From the top of the second stripping column, second laden gas is conducted out at a rate of 31823 kg/h (temperature=94.8° C., pressure=1.56 bar) and recycled into the quench 1 (it is fed in together with the product gas mixture to be cooled).

The bottom space of the condensation column is, as already mentioned, at a column height (like all heights, calculated from the base (not including the bottom intake)) of 8.10 m, concluded by a first collecting tray (chimney tray having 16 roofed chimneys in approximately homogeneous distribution).

The aforementioned bottom space of the condensation column ends with an intake (internal diameter=2.0 in). The length of the bottom intake is 2.0 m (these are not included in the above 8.10 m).

The collecting tray has a double wall (the intermediate space is purged continuously with lean air at outside temperature (mixture of air and molecular nitrogen; the content of molecular oxygen in the mixture is 6% by volume)(typical flow rates are 5 to 301 (STP)/h); in this way, the intention is to provide a slightly elevated pressure in the intermediate space, which counteracts penetration of water vapor through unwanted orifices (for example cracks)) with a 1.5° gradient to the inside and with a central draw channel and draw stub. The free gas cross section is approx. 30%.

From this first collecting tray, 112215 kg/h of high boiler fraction are conducted into the bottom space below the first collecting tray.

The high boiler fraction has, at a temperature of 101.4° C. and a pressure of approx. 1.52 bar, the following contents:
- 93.9% by wt. of acrylic acid,
- 0.532% by wt. of acetic acid,
- 1.35% by wt. of water,
- 0.0177% by wt. of formic acid,
- 0.0033% by wt. of formaldehyde,
- 0.0057% by wt. of acrolein,
- 0.0875% by wt. of propionic acid,
- 0.210% by wt. of furfurals,
- 0.0027% by wt. of allyl acrylate,
- 0.0016% by wt. of allyl formate,
- 0.122% by wt. of benzaldehyde,
- 3.17% by wt. of maleic anhydride,
- 0.0128% by wt. of benzoic acid,
- 0.0033% by wt. of phthalic anhydride,
- 0.5343% by wt. of diacrylic acid,
- 0.0075% by wt. of phenothiazine,
- 0.0395% by wt. of MEHQ, and
- 0.0001% by wt. of $O_2$.

The bottom temperature is 107.0° C. and the bottom pressure (at the liquid level) is 1.52 bar.

1.5 m above the first collecting tray is the first dual-flow tray of a sequence of at first 15 dual-flow trays. These dual-flow trays (orifice ratio=a uniform 16%) are mounted equidistantly one above another with a (clear) tray separation of 400 mm. The passage orifices consist of circular orifices of uniform diameter 14 mm, with the punching burr pointing downward in the separation column. The arrangement of the centers of the passage circles follows a strict triangular pitch.

The fifteenth dual-flow tray functions as a distributor tray. For this purpose, the column wall comprises, between the second collecting tray and the fifteenth dual-flow tray, two inserted tubes (DN~150) with 45 outlet holes (diameter: 15 mm) per inserted tube.

Through the inserted tubes, crude acrylic acid and mother liquor are recycled into the condensation column.

The first series (sequence) of dual-flow trays is concluded with a second double-wall (the intermediate space is, in a corresponding manner to that already described, purged continuously with lean air (mixture of air and molecular nitrogen; the content of molecular oxygen in the mixture is 6% by volume)) collecting tray (chimney tray having 16 roofed chimneys in approximately homogeneous distribution; central draw channel with draw stub, free gas cross section of ~30%), which is mounted 1.50 m above the last dual-flow tray and has a gradient of 1.5° toward the draw channel.

From this second collecting tray, as the first side draw, a crude acrylic acid (228421 kg/h) with a temperature of 98.5° C. is withdrawn continuously at 1.49 bar, and has the following contents:
- 96.8% by wt. of acrylic acid,
- 0.78% by wt. of acetic acid,
- 1.70% by wt. of water,
- 0.0233% by wt. of formic acid,
- 0.0040% by wt. of formaldehyde,
- 0.0055% by wt. of acrolein,
- 0.103% by wt. of propionic acid,
- 0.0944% by wt. of furfurals,
- 0.0033% by wt. of allyl acrylate,
- 0.0019% by wt. of allyl formate,
- 0.0166% by wt. of benzaldehyde,
- 0.1723% by wt. of maleic anhydride,
- 0.271% by wt. of diacrylic acid,
- 0.0060% by wt. of phenothiazine,
- 0.0186% by wt. of MEHQ, and
- 0.0001% by wt. of oxygen.

77575 kg/h of the crude acrylic acid withdrawn from the second collecting tray are recycled directly into the condensation column in the space between this collecting tray and the lowermost dual-flow tray of a second sequence (series) of dual-flow trays arranged above it. Appropriately in application terms, the recycling is effected via nozzles mounted on a ring line (normally 7 to 10), distributed uniformly over the column cross section, by spraying. About half of the nozzles are directed downward and the rest of the nozzles are directed upward.

47517 kg/h of the crude acrylic acid withdrawn from the second collecting tray are recycled into the condensation column together with mother liquor obtained in the course of crystallizative further purification of crude acrylic acid withdrawn and heated to 93° C. in indirect heat exchange with crude acrylic acid withdrawn (103329 kg/h) (the overall mother liquor stream at 20° C. for this heat exchange=78080 kg/h; 70080 kg/h thereof are recycled into the condensation column; 8000 kg/h are conducted into the second stripping column at the top thereof) via the aforementioned inserted tubes immediately below the second collecting tray to the dual-flow tray which follows it in the downward direction.

The 103329 kg/h of crude acrylic acid which has been withdrawn from the second collecting tray and cooled to 43.2° C. in a heat-integrated system against the aforementioned mother liquor are cooled to a temperature of 20° C. by indirect heat exchange in two further series-connected exchange stages against cooling water and cold water as coolants and optionally intermediately buffered in a tank farm. Then the cooled crude acrylic acid is supplemented with a substream of 2494 kg/h of acid water which has been withdrawn from the second side draw of the condensation column at 61.2° C. and cooled to 20.7° C.

The acid water has the following contents:
9.46% by wt. of acrylic acid,
6.09% by wt. of acetic acid,
79.6% by wt. of water,
0.640% by wt. of formic acid,
4.1219% by wt. of formaldehyde,
0.0174% by wt. of acrolein,
0.0104% by wt. of propionic acid,
0.0006% by wt. of furfurals,
0.0586% by wt. of allyl formate,
0.0001% by wt. of MEHQ, and
0.0010% by wt. of oxygen.

The resulting mixture is cooled to 11 to 13° C. by another indirect heat exchange (against cooling fluid (water/glycol mixture; 25-35% by weight of glycol and 65-75% by weight of water)) and then divided and conducted into two to three cooling-disk crystallizers operated in parallel (cf. WO 2006/111565). Each of these comprises a trough in which 24 wiped circular cooling plates (with a cooling medium (mixture of water and glycol; glycol content=25 to 35% by weight) flowing through the interior of each) are arranged hanging in succession at an equidistant separation of 30±1 cm (plate diameter=3.3 m). The particular cooling medium is passed onward from cooling disk to next-but-one cooling disk through the particular crystallizer, in countercurrent to the crystallizing mixture. In other words, the particular cooling medium is divided and conducted in the form of two parallel streams through the cooling plates of the particular crystallizer. One stream leads through the even-numbered cooling plates, the other stream through the odd-numbered cooling plates (numbering of the cooling disks in flow direction beginning with 1). The particular amount of cooling medium per crystallizer is a total of 180-220 t/h (metric tons), i.e. 90-110 t/h per stream. The pressure drop per cooling disk is 60 to 100 mbar. The inlet temperature of the cooling medium (of the fluid) is +2.0 to +2.5° C. The outlet temperature is about 3.0° C. higher. The wall thickness of the cooling surfaces manufactured from stainless steel is 4 mm. The heat transfer coefficient on the fluid side is about 1500 to 2500 W/(m$^2$·K) The heat transfer coefficients are usually 350 to 500 W/(m$^2$·K) The specific cooling performance is 1.5 to 2.0 kW/m$^2$ of cooling surface area. The wiping of the cooling plates suppresses the formation of a crystal layer. The crude acrylic acid of increased water content is conducted continuously from the back forward through the particular crystallizer (pumped or under overflow control). At the same time, the monophasic crude acrylic acid of increased water content thickens (residence time 1.5 to 2.5 h) to a biphasic suspension comprising acrylic acid crystals as a solid phase having a temperature of 7 to 8.5° C. and a solids content at the outlet of about 25% by weight. The mass density of the suspension is typically 1110 to 1115 kg/m$^3$. The speed of the wipers is 5 to 6 revolutions per minute. The shaft which drives the wipers and passes through the centers of the cooling disks is sealed with water-washed stuffing box packings (packing threads of Teflon or graphite, wash rate=a few liters per hour up to several tens of 1/h per seal).

On the circumference of the cooling disks, where it is not possible to wipe, a hollow profile (e.g. a tube in the simplest embodiment) is mounted (for example welded on), and is heated by means of a second heat carrier (for example likewise water/glycol mixture) (to a temperature above the crystallization temperature; usually from the temperature range of 8 to 20° C., preferably 10 to 14° C.). These peripheral heaters are flowed through in parallel by the second heat carrier.

In addition, the wipers are preferably segmented in radial direction (4 segments). The specific pressing force of the wipers in the installed state, perpendicular to the cooling surface, is 3 to 5 N per cm of active wiper edge length. The wiper material used is high molecular weight polyethylene or ultra-high molecular weight polyethylene, for example Multilene® PE 1000. In addition to the wipers, the shaft drives paddles (there are appropriately two each in a symmetrical arrangement between two cooling disks and before the first and last cooling disk), which bring about improved mixing.

In the last section of the particular crystallizer in conveying direction of the suspension (preferably beyond the last cooling disk), the suspension is conducted over an overflow weir into a stirred collecting vessel from which hydraulic melt wash columns are charged, as described in EP-A 1 272 453, EP-A 1 448 283, WO 03/041833, EP-A 1 305 097, DE-A 101 56 016, DE-A 10 2005 018 702 and in DE-A 102 23 058, in order to remove the mother liquor from the suspension crystals. The wash column diameter is 1.4 m. The wash columns are charged with crystal suspension by means of a centrifugal pump (channel wheel type), the flow preferably being controlled by means of speed regulation of the pump. The control stream pump is likewise configured as a centrifugal pump with regulating valve. Typically, the control stream flow employed to regulate a wash column is 5 to 60 t/h, usually 8 to 30 t/h. In some cases, it is possible to operate the particular wash column without a control stream when the amount of liquid supplied with the suspension is already sufficient for the transport of the crystal bed. Typical ratios of effective transport pressure difference to effective wash pressure difference are 1.1 to 3, usually 1.2 to 1.8. The blade speed is usually at values of 5 to 10 per minute. The temperature in the melt circuit is normally 13 to 16° C. The monitoring of the filtration front is undertaken in accordance with DE-A 10 2005 018 702 by means of two pressure drop measurements over different bed lengths placed in a ratio relative to one another. The wash front is controlled by means of temperature measurement in the crystal bed.

For control reasons, the total height of the crystal bed is 250 to 1500 mm, usually 600 to 1100 mm. The wash front is typically 80 to 180 mm above the blade. Suitable melt circuit pumps are centrifugal pumps with product-side flushing of the shaft seal (slip-ring seal; double design). The circulation rate in the particular melt circuit is 10 to 15 m$^3$/h per tonne of purified crystals scraped off with the blade (the melt circuit can be stabilized according to the subsequent use in a column-specific manner with 200 to 300 ppm by weight of MEHQ, or with 40 to 70 ppm by weight of MEHQ, or with 100 to 300 ppm by weight of PTZ; in addition, air is introduced into the melt circuit, the excess of which (=proportion not dissolved in the wash melt) is removed by means of a gas separator before entry of the wash melt into the wash column. This establishes a content of dissolved oxygen of 5 to 40 ppm by weight in the molten pure product).

From the melt circuits, which are stabilized by the addition of a total of 210 kg/h of a solution (temperature=20.5° C., pressure=1.1 bar) of 2.1 kg/h of MEHQ in 207.9 kg/h of glacial acrylic acid withdrawn from the melt circuits (20° C.) and introduction of air, are withdrawn 27953 kg/h of glacial acrylic acid (temperature=15° C., pressure=2.5 bar) of the following contents, which are warmed to 20° C. by indirect heat exchange and decompressed to 1.5 bar:

99.74% by wt. of acrylic acid,
0.195% by wt. of acetic acid,
0.026% by wt. of water,
0.0305% by wt. of propionic acid,
0.0001% by wt. of furfurals,
≤0.0001% by wt. of benzaldehyde,
0.0001% by wt. of maleic anhydride,
0.0002% by wt. of diacrylic acid,
0.0070% by wt. of MEHQ and
0.001% by wt. of $O_2$.

It is outstandingly suitable for production of superabsorbents based on poly(sodium acrylate).

9 kg/h of PTZ are dissolved in 745 kg/h of the aforementioned heated glacial acrylic acid to produce 754 kg/h of an inhibitor solution 1 at 20° C.

2.1 kg/h of molten (80° C.) MEHQ are dissolved in 207.9 kg/h of the aforementioned heated glacial acrylic acid and used as described for stabilization of the melt circuits.

27000 kg/h of MEHQ-stabilized (70 ppm by weight) glacial acrylic acid (20° C., 1.5 bar) are supplied continuously to the storage tank.

The mother liquor removed in the wash columns is first conducted into a heatable collecting vessel and from there into a tank. From this tank, it is (as already mentioned, as a total flow rate of 78080 kg/h) heated to 93° C. in a heat-integrated system and recycled at a rate of 70080 kg/h, together with 47517 kg/h of crude acrylic acid withdrawn from the second collecting tray, to the fifteenth dual-flow tray of the condensation column (counted from the bottom). 8000 kg/h of the mother liquor heated in a heat-integrated system are, as already mentioned, supplied to the second stripping column at the top thereof (as reflux liquid). The addition at the top of the second stripping column is effected via a ring line with 8 spray nozzles downward and one spray nozzle directed upward, distributed uniformly over the cross section thereof. The composition of this recycled mother liquor is as follows:

93.0% by wt. of acrylic acid,
1.16% by wt. of acetic acid,
4.7437% by wt. of water,
0.0512% by wt. of formic acid,
0.138% by wt. of formaldehyde,
0.0079% by wt. of acrolein,
0.127% by wt. of propionic acid,
0.125% by wt. of furfurals,
0.0043% by wt. of allyl acrylate,
0.0044% by wt. of allyl formate,
0.0219% by wt. of benzaldehyde,
0.225% by wt. of maleic anhydride,
0.358% by wt. of diacrylic acid,
0.0078% by wt. of phenothiazine,
0.0248% by wt. of MEHQ, and
0.001% by wt. of oxygen.

3.0 m above the second collecting tray in the condensation column is the first of 24 further dual-flow trays of the type already described (hole diameter again a uniform 14 mm), which are again arranged equidistantly with a tray separation of 400 mm.

These are followed, as shown in FIGS. 21 and 22, successively with a clear separation of 500 mm in each case, by two dual-flow trays of segmented design which project into a manhole present in this section (hole diameter likewise a uniform 14 mm and orifice ratio=16%).

600 mm above the upper of the two aforementioned dual-flow trays is a hydraulically sealed hood tray configured as a distributor tray, as shown in top view in FIG. 17 of this document.

600 mm above the transition tray begins an equidistant (tray separation=600 mm) arrangement of 24 inventive crossflow hood trays, as detailed in FIGS. 5 and 6 of this document and described in this document in the context of these figures.

1.50 m above the uppermost inventive crossflow mass transfer tray (crossflow hood tray) is the third collecting tray (chimney tray with 16 approximately uniformly distributed roofed chimneys, central outlet channel, tray inclined 1.5° toward the outlet channel).

From the third collecting tray, as the second side draw, 828725 kg/h of acid water are withdrawn with a temperature of 61.2° C. and at a pressure of ~1.25 bar.

The acid water has, as already mentioned, the following contents:

9.46% by wt. of acrylic acid,
6.09% by wt. of acetic acid,
79.6% by wt. of water,
0.640% by wt. of formic acid,
4.1219% by wt. of formaldehyde,
0.0174% by wt. of acrolein,
0.0104% by wt. of propionic acid,
0.0006% by wt. of furfurals,
0.0586% by wt. of allyl formate,
0.0001% by wt. of MEHQ, and
0.0010% by wt. of oxygen.

35213 kg/h of the acid water withdrawn (61.2° C.) are recycled together with 65 kg/h of inhibitor solution 1 (20° C.) and 27.7 kg/h of molten MEHQ (80° C.) to the uppermost inventive crossflow mass transfer tray (crossflow hood tray).

689 kg/h of inhibitor solution 1 are (viewed from below) recycled to the 9th inventive crossflow hood tray (with a temperature of 20° C.).

460 m³/h of the acid water withdrawn are recycled at a temperature of 26.5° C. to the fifth of the valve trays to be described hereinafter (counted from the bottom) (the cooling is effected by multistage indirect heat exchange; the coolant used is air, cooling water and cold water).

326494 kg/h of the acid water withdrawn are cooled to a temperature of 20.7° C. (the cooling is effected together with the above flow rate of acid water by multistage indirect heat exchange; the last cooling stage from 26.5° C. to 20.7° C. is effected separately and in a heat-integrated system (liquid polymer-grade propylene is used as a coolant and evaporates in the process; the resulting gaseous propylene is subsequently used to configure the reaction gas mixture for the gas phase partial oxidation).

324000 kg/h of the acid water cooled to 20.7° C. are recycled at this temperature to the uppermost of the valve trays to be described hereinafter.

2494 kg/h of the acid water cooled to 20.7° C. are added at this temperature, as already described, to the crude acrylic acid to be purified further by crystallization.

11018 kg/h of the acid water withdrawn are supplied (at the temperature of 61.2° C.) to the extraction column for the purpose of the extraction which is still to be detailed hereinafter.

2.4 mm above the third collecting tray are mounted, in the condensation column, in equidistant arrangement (tray separation=600 mm), 10 conventional two-flow (cf. WO 2008/090190 A1) valve trays. The height of the outlet weir is 15 to 20 mm (the outlet weirs of the lower trays are higher like those of the upper trays). The orifice ratio (specific hole area) is 14.8% and the sum of the outlet areas of the downcomers of two successive valve trays is ~12% (12.7% in the case of a lateral shaft and 12.5% in the case of a central shaft) of the column cross-sectional area. The valves used are valves of the TH-7 type or equivalent valves.

The pressure at the top of the condensation column is 1.17 bar.

At the top of the column, 222463 kg/h of residual gas leave the separation column at a temperature of 22.3° C. and with the following contents:
0.0957% by wt. of acrylic acid,
0.0679% by wt. of acetic acid,
1.36% by wt. of water,
0.0037% by wt. of formic acid,
0.0994% by wt. of acrolein,
0.0001% by wt. of propionic acid,
0.0001% by wt. of furfurals,
0.0027% by wt. of allyl formate,
2.62% by wt. of $CO_2$,
0.7434% by wt. of CO,
0.191% by wt. of propane,
0.306% by wt. of propylene,
3.81% by wt. of $O_2$, and
90.7% by wt. of $N_2$.

In an indirect heat exchanger, the residual gas is warmed to 27° C. and then 122641 kg/h of this residual gas are compressed to a pressure of 3.3 bar by means of a cycle gas compressor, in the course of which the temperature rises to approx. 161° C. 102641 kg/h of the compressed residual gas are recycled into the gas phase partial oxidation as cycle gas. 17793 kg/h of the compressed residual gas are supplied to the first stripping column for the purpose of stripping the extract from the acid water extraction, and 2207 kg/h of the compressed residual gas are supplied directly to the second stripping column.

99822 kg/h of the residual gas leaving the condensation column at the top thereof are supplied to the incineration without additional compression.

The extraction column for the acid water extraction comprises, as separating internals, perforated structured stainless steel (material 1.4571) packings fitted flush to the edge (height of one packing element: 200 mm) of the Montz-Pak B1-350 type with an active total height of 14 m, which are arranged one above another.

The internal diameter of the extraction column over all structured packings is a uniform 1000 mm. The height thereof is 19 m. The extractant used is Palatinol® A. The diameter of the bottom and top vessels of the column has been extended to 1.4 m (bottom) and 1.6 m (top) in order to improve the phase separation in the bottom and to reduce the entrainment of extractant in the top of the column. Additionally introduced in the top of the column is a bed of random plastic packings (e.g. polyethylene or Teflon) as a coalescence aid.

11018 kg/h of acid water to be extracted (temperature=61.2° C.) are fed into the extraction column below the lowermost packing via pipe distributors having appropriate passage orifices (holes of diameter 10 mm). Above the uppermost packing of the extraction column, a mixture of approx. 29 kg/h of fresh Palatinol® A and 11425 kg/h of extractant which has been recycled from the first stripping column and has been stripped free therein beforehand (introduction temperature=50° C.) is introduced.

The recycled extractant has the following contents:
0.139% by wt. of acrylic acid,
0.048% by wt. of acetic acid,
0.0134% by wt. of water,
0.0002% by wt. of formic acid,
0.0014% by wt. of acrolein,
0.0009% by wt. of propionic acid,
0.0005% by wt. of furfurals,
0.0001% by wt. of allyl formate,
0.0214% by wt. of MEHQ,
0.0001% by wt. of oxygen, and
99.775% by wt. of Palatinol® A.

The specific mass of the acid water is 961.9 kg/m$^3$. The extractant is likewise introduced via pipe distributors having appropriate passage orifices (holes of diameter 5 mm).

The acid water forms the continuous phase and the extractant forms the phase dispersed in the form of droplets (droplet diameter within the range from 2 to 5 mm), which descends in the aqueous phase.

At the top of the extraction column, 9181 kg/h of raffinate (temperature ~55.3° C.) are withdrawn, which has the following contents:
0.938% by wt. of acrylic acid,
4.29% by wt. of acetic acid,
89.2% by wt. of water,
0.574% by wt. of formic acid,
4.78% by wt. of formaldehyde, and
0.218% by wt. of Palatinol® A.

It is sent to the incineration together with residual gas to be incinerated. 13292 kg/h of extract are withdrawn from the bottom of the extraction column which has the following contents (temperature ~60.9° C.):
7.31% by wt. of acrylic acid,
2.08% by wt. of acetic acid,
4.38% by wt. of water,
0.134% by wt. of formic acid,
0.130% by wt. of formaldehyde,
0.0156% by wt. of acrolein,
0.0094% by wt. of propionic acid,
0.0009% by wt. of furfurals,
0.0486% by wt. of allyl formate,
0.0185% by wt. of MEHQ, and
85.873% by wt. of Palatinol® A.

The entire amount of the extract is conducted to the top of the first stripping column. The extract is heated to 111° C. beforehand by indirect heat exchange in a heat exchanger. The heat carrier used is 11454 kg/h of mixture of 11425 kg/h of bottoms liquid withdrawn (178° C.) from the first stripping column and approx. 29 kg/h of added fresh (25° C.) Palatinol® A. This mixture cools down to 120° C. in the process. By subsequent further indirect heat exchange, the mixture temperature is reduced to 50° C. (=introduction temperature for the extraction column). The first stripping column comprises, as separating internals, 5 dual-flow trays and 15 conventional (one-flow (cf. WO 2008/090190 A1)) crossflow Thormann trays. Just like the extraction column, the first stripping column is thermally insulated from the environment. The internal diameter of the first stripping column over all trays is a uniform 1.7 m.

The height thereof is 15.4 m. The lowermost 5 trays are configured as dual-flow trays and are arranged equidistantly (separation=600 mm) in the first stripping column. The orifice ratio thereof is a uniform 20%. The hole diameter of the dual-flow trays is a uniform 14 mm (hole arrangement corresponding to strict triangular pitch). Above the uppermost dual-flow tray are 15 conventional one-flow crossflow Thormann trays arranged equidistantly (separation 500 mm). These Thormann trays are configured such that, through the arrangement of the forcing slots in the hoods of the Thormann trays, opposite flow directions of the liquid are generated in each case in successive channels in crossflow direction. The orifice ratio (gas passage area based on the cross section) is 14%.

Above the last tray there is also a bed (height 600 mm, metal pall rings, 25×25) as a droplet catcher.

Below the lowermost dual-flow tray, 6940 m³ (STP)/h of compressed residual gas (pressure ~3.3 bar, temperature ~160.9° C.) are conducted into the first stripping column, where it ascends in countercurrent to the extract descending in the first stripping column.

At the top of the first stripping column, 19659 kg/h of first laden gas are conducted out (temperature=85.5° C., pressure: 1.78 bar) and supplied to the second stripping column. The temperature in the bottom of the first stripping column is about 178° C. 111425 kg/h of bottoms liquid are withdrawn continuously from the bottom of the first stripping column. 11425 kg/h of the bottoms liquid withdrawn from the first stripping column, supplemented with approx. 29 kg/h of fresh (25° C.) Palatinol® A, are cooled to 50° C. by two-stage indirect heat exchange (the first stage in a plate heat exchanger in a heat-integrated system against extract) and recycled to the top of the extraction column. 105 m³/h of the bottoms liquid withdrawn from the first stripping column are heated to 188° C. in an external forced-circulation shell-and-tube flash evaporator and recycled into the bottom of the first stripping column.

After 70 days of uninterrupted operation of the process, no formation of unwanted polymer is detectable in the inventive sequence of crossflow hood trays used in the condensation column.

COMPARATIVE EXAMPLE

The procedure is as in the example, except that the inventive crossflow hood trays above the hydraulically scaled "distributor" hood tray mounted between the dual-flow trays and the inventive crossflow hood trays are replaced by a sequence of identical crossflow hood trays which differ from an inventive crossflow hood tray only in that the downcomers of the inventive crossflow hood tray are combined to a single downcomer with the same (total) cross-sectional area, and this downcomer is present in the opposite half of the crossflow mass transfer tray to the at least one feed, at the outer edge thereof, and all lines of passage orifices of the mass transfer tray are in front of the one downcomer in the opposite direction to crossflow direction (i.e. there is no passage orifice beyond the downcomer in crossflow direction).

After 70 days of uninterrupted operation of the process, clearly visible formation of unwanted polymer is found in the noninventive sequence of crossflow hood trays used in the condensation column. The purity of the crude acrylic acid withdrawn is essentially unchanged (difference<0.3 percentage points by weight).

U.S. Provisional Patent Application No. 61/613,024, filed Mar. 20, 2012, is incorporated into the present patent application by literature reference.

With regard to the abovementioned teachings, numerous changes and deviations from the present invention are possible. It can therefore be assumed that the invention, within the scope of the appended claims, can be performed differently than the way described specifically herein

The invention claimed is:

1. A thermal separation process, comprising passing at least one gas through a separation column comprising separating internals, such that the at least one gas ascends within the separation column and at least one liquid descends within the separation column, at least one of which comprises (meth) acrylic monomers,
wherein:
at least some of the separating internals comprise at least one sequence of at least two identical crossflow mass transfer trays having at least one downcomer through which liquid descends from a particular crossflow mass transfer tray, such that the crossflow mass transfer trays are arranged one on top of another within the at least one sequence in the separation column;
two crossflow mass transfer trays in the separation column, one of which follows the other in the downward direction, are each mounted offset from one another by 180° about the longitudinal axis of the column, as a result of which their downcomers are on mutually opposite sides of the separation column;
the at least one downcomer of an upper of two successive crossflow mass transfer trays constitutes at least one upcomer for the crossflow mass transfer tray below it, through which the liquid descends from the upper crossflow mass transfer tray as at least one feed to the crossflow mass transfer tray below it;
the liquid descending through the at least one upcomer from the upper to the lower crossflow mass transfer tray, viewed over the (entire) lower crossflow mass transfer tray, flows from the at least one feed to the lower crossflow mass transfer tray across the tray to the at least one downcomer of the lower crossflow mass transfer tray;
passage orifices are situated between the at least one feed to the lower crossflow mass transfer tray and the at least one downcomer of the lower crossflow mass transfer tray, through which the at least one gas ascends through the lower crossflow mass transfer tray; and
at least within one of the at least one sequence of identical crossflow mass transfer trays, the lower of two successive crossflow mass transfer trays in each case, in the direction of the crossflow from the at least one feed thereof to the at least one downcomer thereof, additionally has at least one passage orifice for the at least one ascending gas beyond at least one downcomer.

2. The thermal separation process according to claim 1, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is a sequence of crossflow sieve trays, or of crossflow bubble-cap trays, or of crossflow valve trays.

3. The thermal separation process according to claim 1, wherein the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer comprises not more than fifty identical crossflow mass transfer trays.

4. The thermal separation process according to claim 1, wherein the crossflow mass transfer trays of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer are arranged equidistantly one above another.

5. The thermal separation process according to claim 1, wherein, within the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, the liquid flows on the lower crossflow mass transfer tray in each case from the at least one feed in a meandering manner to the at least one downcomer.

6. The thermal separation process according to claim 1, wherein the separation column comprises at least one further separating internal selected from the group consist dual-flow trays, and a random packing.

7. The thermal separation process according to claim 1, wherein a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer has not more than twenty downcomers.

8. The thermal separation process according to claim 1, wherein the downflow orifices of the downcomers of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.

9. The thermal separation process according to claim 1, wherein the cross section of the downflow orifice of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is circular, or rectangular, or square, or that of an elongated hole.

10. The thermal separation process according to claim 1, wherein a total area of the cross-sectional areas of the downflow orifices of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, is not more than 20% of the cross-sectional area of the crossflow mass transfer tray.

11. The thermal separation process according to claim 1 wherein a total area of the cross-sectional areas of the downflow orifices of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, is at least 0.2% of the cross-sectional area of the crossflow mass transfer tray.

12. The thermal separation process according to claim 1, wherein a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, in the direction of crossflow from the at least one feed thereof to the at least one downcomer thereof, additionally has at least one passage orifice for the at least one ascending gas beyond at least half of all downcomers.

13. The thermal separation process according to claim 1, wherein the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is surrounded on all sides by passage orifices.

14. The thermal separation process according to claim 1, wherein a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer has a circular cross section.

15. The thermal separation process according to claim 14, wherein the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is within a circle segment of the crossflow mass transfer tray, the area of which is not more than two thirds of half the circle area of the crossflow mass transfer tray.

16. The thermal separation process according to claim 14, wherein the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is within a circle segment of the crossflow mass transfer tray, the area of which is at least one fifth of half the circle area of the crossflow mass transfer tray.

17. The thermal separation process according to claim 15, wherein the downflow orifices of the at least one downcomer are arranged within the circle segment such that there is no further downflow orifice on that straight line which joins the center of a downflow orifice to the center of the feed area of the feed opposite.

18. The thermal separation process according to claim 15, wherein the downflow orifices of the at least one downcomer are arranged within the circle segment such that the shortest direct connecting line from the center of a downflow orifice to a point on the circumference line of the crossflow mass transfer tray is not longer than two thirds of the radius of the crossflow mass transfer tray.

19. The thermal separation process according to claim 14, wherein the distance between the center of the downflow orifice of the at least one downcomer of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer, and the geometric center of the circular crossflow mass transfer tray is at least as long as one third of the radius of the crossflow mass transfer tray.

20. The thermal separation process according to claim 1, wherein the at least one downcomer of the upper of two successive crossflow mass transfer trays in each case within the at least one sequence of identical crossflow mass transfer trays in which the lower of two successive crossflow mass transfer trays in each case, in the direction of crossflow from the at least one feed thereof to the at least one downcomer thereof, additionally has at least one passage orifice for the at least one ascending gas beyond at least one downcomer, is extended downward as an upcomer for the lower crossflow mass transfer tray in each case to such an extent that it is immersed into the liquid flowing on the lower crossflow mass transfer tray.

21. The thermal separation process according to claim 1, wherein the at least one downcomer of the upper of two successive crossflow mass transfer trays in each case within the at least one sequence of identical crossflow mass transfer trays in which the lower of two successive crossflow mass transfer trays in each case, in the direction of crossflow from the at least one feed thereof to the at least one downcomer thereof, additionally has at least one passage orifice for the at least one ascending gas beyond at least one downcomer, is extended downward as an upcomer for the lower crossflow mass transfer tray in each case only to such an extent that it is not immersed into the liquid flowing on the lower crossflow mass transfer tray.

22. The thermal separation process according to claim 21, wherein the liquid descending in the upcomer to the lower crossflow mass transfer tray descends onto a feed area of the lower crossflow mass transfer tray, said feed area having passage orifices.

23. The thermal separation process according to claim 1, wherein at least 20% of the passage orifices of a crossflow mass transfer tray of the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer have a uniform cross section.

24. The thermal separation process according to claim 1, wherein the at least one (meth)acrylic monomer is selected from the group consisting of acrolein, acrylic acid, an ester of acrylic acid, methacrolein, methacrylic acid and an ester of methacrylic acid.

25. The thermal separation process according to claim 1, which is a process for fractional condensation for removal of acrylic acid from a product gas mixture comprising acrylic acid from a heterogeneously catalyzed gas phase partial oxidation of a C3 precursor compound of acrylic acid with molecular oxygen to give acrylic acid.

26. The thermal separation process according to claim 25, wherein:
the at least one sequence of identical crossflow mass transfer trays within which the lower of two successive crossflow mass transfer trays in each case, in the direction of crossflow from the at least one feed thereof to the at least one downcomer thereof, additionally has at least one passage orifice for the at least one ascending gas beyond at least one downcomer is a sequence of crossflow mass transfer trays whose passage orifices are bubble-cap passage orifices having forcing slots;
in the separation column, below the at least one sequence of identical crossflow mass transfer trays, at least one sequence of dual-flow trays is mounted;
the product gas mixture comprising acrylic acid is supplied to the separation column below the lowermost dual-flow tray; and
condensed acrylic acid is withdrawn from the at least one sequence of dual-flow trays.

27. The thermal separation process according to claim 1, wherein a gaseous and/or liquid mixture comprising ≥2% by weight of at least one (meth)acrylic monomer is supplied to the separation column.

* * * * *